US012611230B2

(12) United States Patent
Patel et al.

(10) Patent No.: US 12,611,230 B2
(45) Date of Patent: Apr. 28, 2026

(54) METHODS AND SYSTEMS RELATED TO JOINT REPAIR

(71) Applicants:Smith & Nephew, Inc., Memphis, TN (US); Smith & Nephew Orthopaedics AG, Zug (CH); Smith & Nephew Asia Pacific Pte. Limited

(72) Inventors: Nehal Patel, Boston, MA (US); Mark Housman, North Attleboro, MA (US); Marc Balboa, Hopkinton, MA (US); Benjamin Hall, Roslindale, MA (US); Jon-Paul Rogers, North Smithfield, RI (US); Matthew Koski, Westford, MA (US); Pascal Boileau, Nice (FR)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 231 days.

(21) Appl. No.: 18/279,799

(22) PCT Filed: Mar. 4, 2022

(86) PCT No.: PCT/US2022/018897
§ 371 (c)(1),
(2) Date: Aug. 31, 2023

(87) PCT Pub. No.: WO2022/187614
PCT Pub. Date: Sep. 9, 2022

(65) Prior Publication Data
US 2024/0148413 A1 May 9, 2024

Related U.S. Application Data

(60) Provisional application No. 63/238,658, filed on Aug. 30, 2021, provisional application No. 63/196,538, (Continued)

(51) Int. Cl.
| | |
|---|---|
| A61B 17/04 | (2006.01) |
| A61B 17/68 | (2006.01) |
| A61B 17/00 | (2006.01) |

(52) U.S. Cl.
CPC ........ A61B 17/683 (2013.01); A61B 17/0401 (2013.01); *A61B 2017/00526* (2013.01);
(Continued)

(58) Field of Classification Search
CPC ............ A61F 2/0811; A61F 2002/0852; A61F 2002/0882; A61F 2002/0817;
(Continued)

(56) References Cited

U.S. PATENT DOCUMENTS

| | | | |
|---|---|---|---|
| 2012/0310279 A1 | 12/2012 | Sikora | |
| 2015/0173739 A1* | 6/2015 | Rodriguez | A61B 17/0401 606/232 |

(Continued)

FOREIGN PATENT DOCUMENTS

| | | | |
|---|---|---|---|
| WO | WO-2012125905 A1 * | 9/2012 | A61B 17/0401 |
| WO | 2020257432 | 12/2020 | |

OTHER PUBLICATIONS

PCT ISR for PCT/US2022/018897 (Year: 2023).*

*Primary Examiner* — Katherine M Shi
(74) *Attorney, Agent, or Firm* — Kate Ryland Tetzlaff; Norman F. Hainer, Jr.

(57) ABSTRACT

Various embodiments and methods for improved joint repair are disclosed. At least some of the embodiments may include an adjustable loop construct with at least one anchor. At least some of the embodiments may include an all-suture anchor. At least some of the embodiments may include an adjustable loop construct with a locking passage. Embodiments may implement a method that reduces or avoids material removal (Continued)

from the bones of the joint. Embodiments may include means to reduce elongation of the repair over time.

16 Claims, 39 Drawing Sheets

Related U.S. Application Data filed on Jun. 3, 2021, provisional application No. 63/180,775, filed on Apr. 28, 2021, provisional application No. 63/156,431, filed on Mar. 4, 2021.

(52) U.S. Cl.
CPC ................ *A61B 2017/0404* (2013.01); *A61B 2017/0409* (2013.01); *A61B 2017/0414* (2013.01)

(58) Field of Classification Search
CPC ......... A61F 2220/0075; A61B 17/0401; A61B 2017/0404; A61B 2017/0406; A61B 2017/0409; A61B 17/683; A61B 2017/0414; A61B 17/8061; A61B 17/80; A61B 2017/0464; A61B 17/1778; A61B 2017/0459; A61B 17/56
See application file for complete search history.

(56) References Cited

U.S. PATENT DOCUMENTS

| | | | |
|---|---|---|---|
| 2019/0038276 A1 | 2/2019 | Jackson | |
| 2019/0053834 A1 | 2/2019 | Bonutti | |
| 2020/0155299 A1 | 5/2020 | Lund | |
| 2021/0106321 A1* | 4/2021 | Solitro | A61F 2/0811 |
| 2021/0186488 A1* | 6/2021 | Grunden | A61B 17/0487 |

* cited by examiner

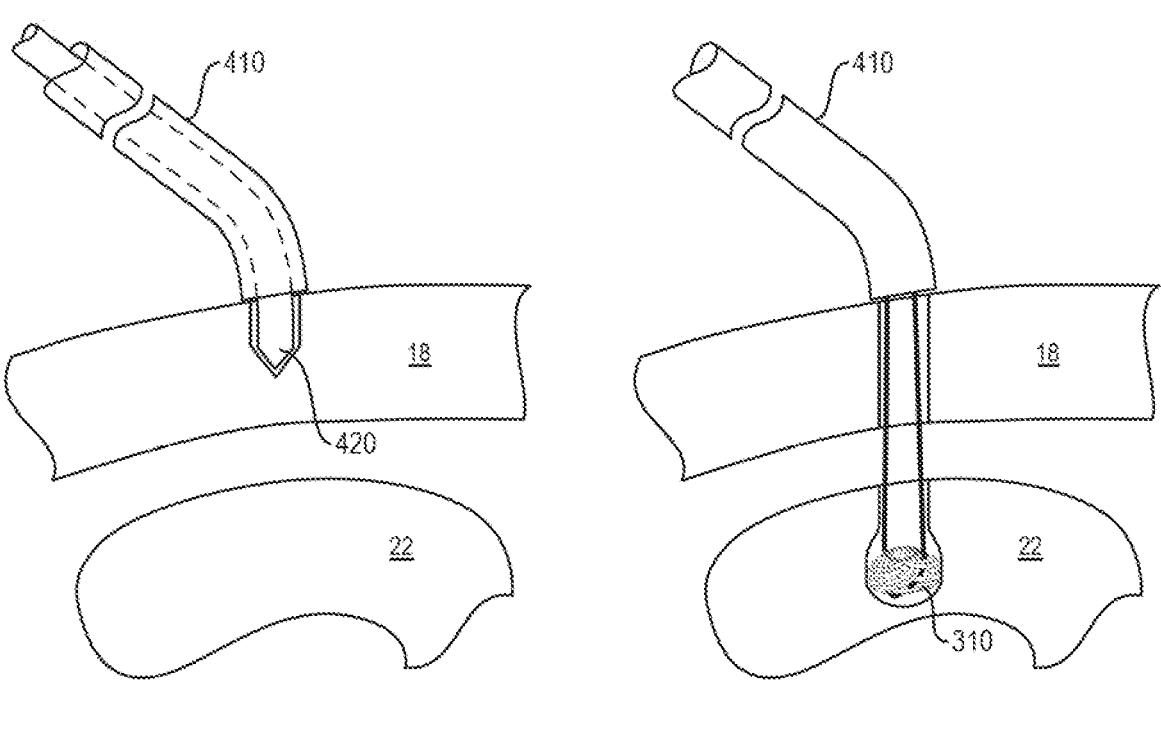
FIG. 9A
FIG. 9B
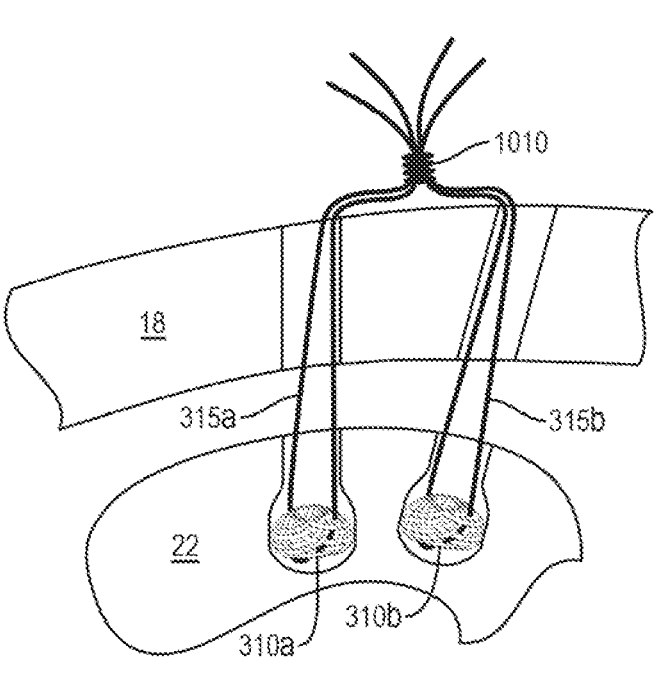
FIG. 10

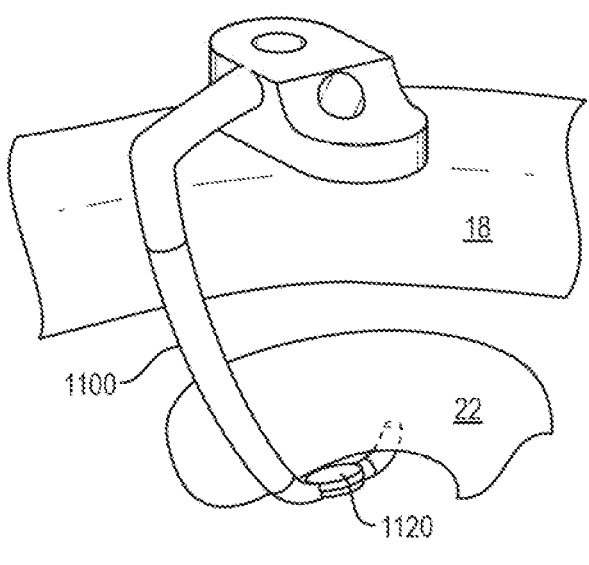
FIG. 11A
FIG. 11B
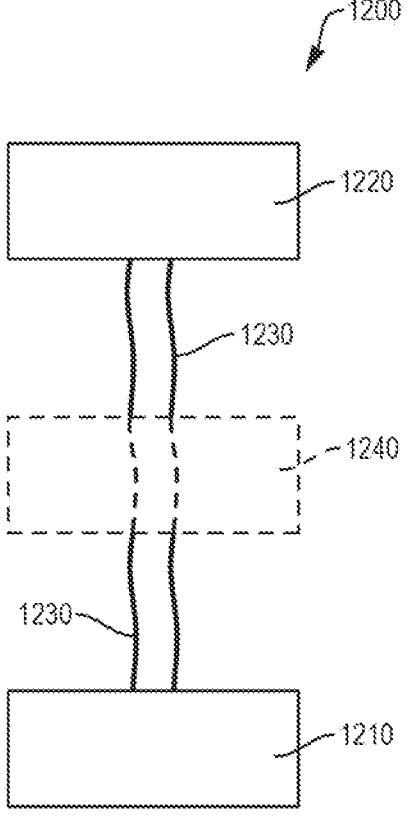
FIG. 12
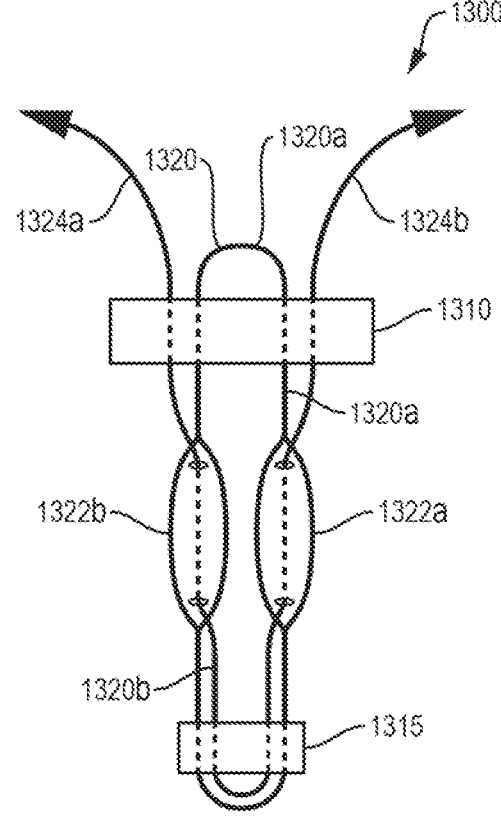
FIG. 13

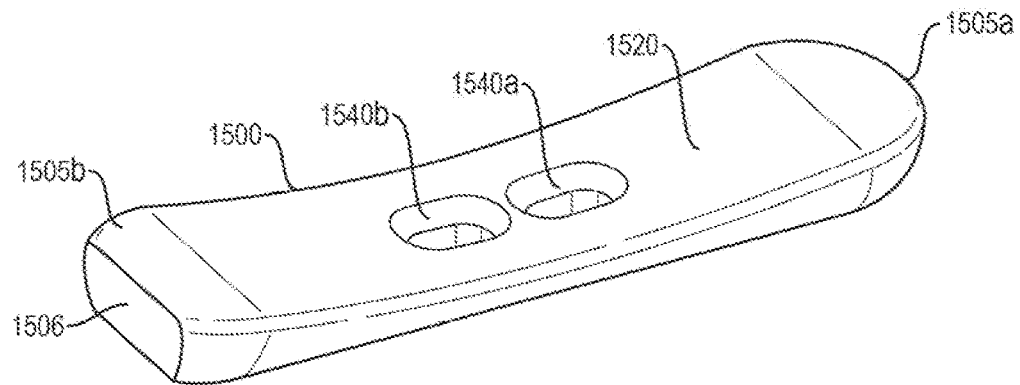
FIG. 15A
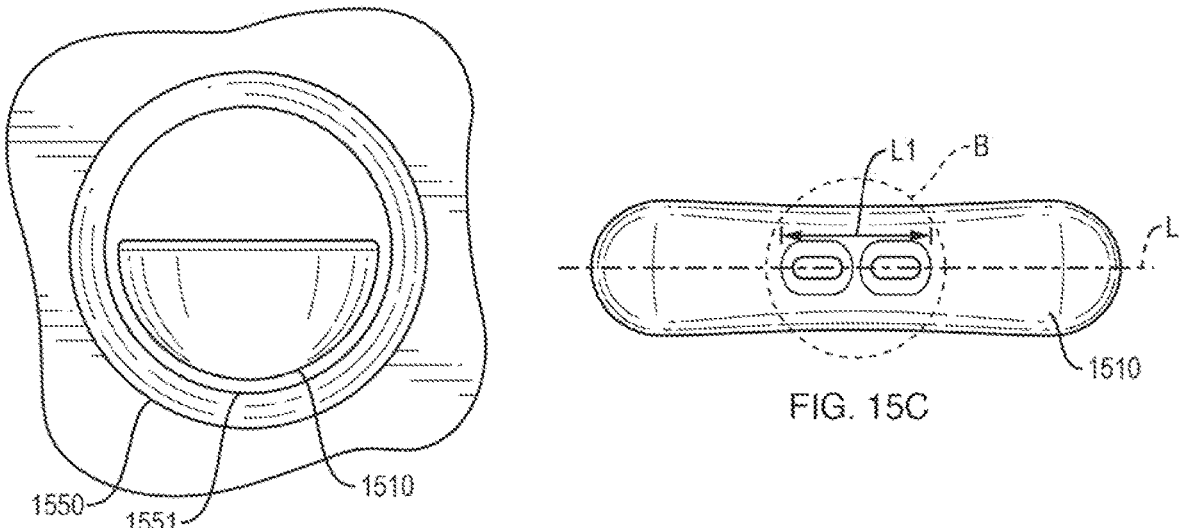
FIG. 15C
FIG. 15B
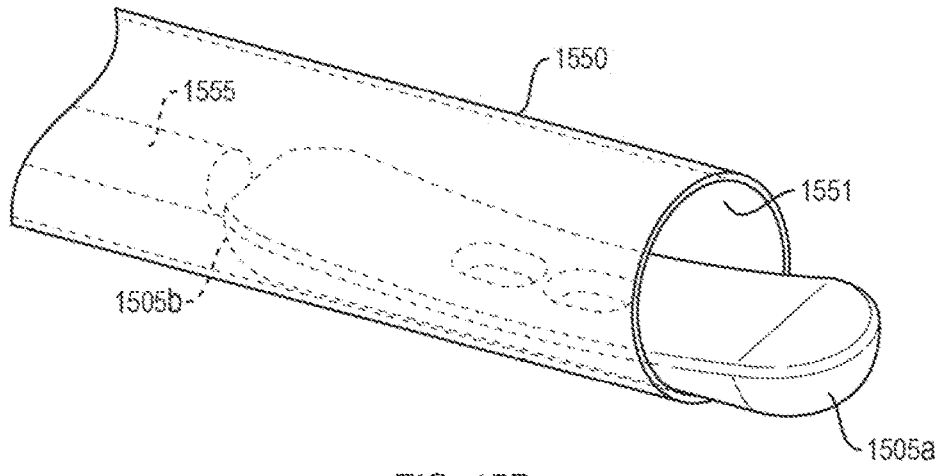
FIG. 15D

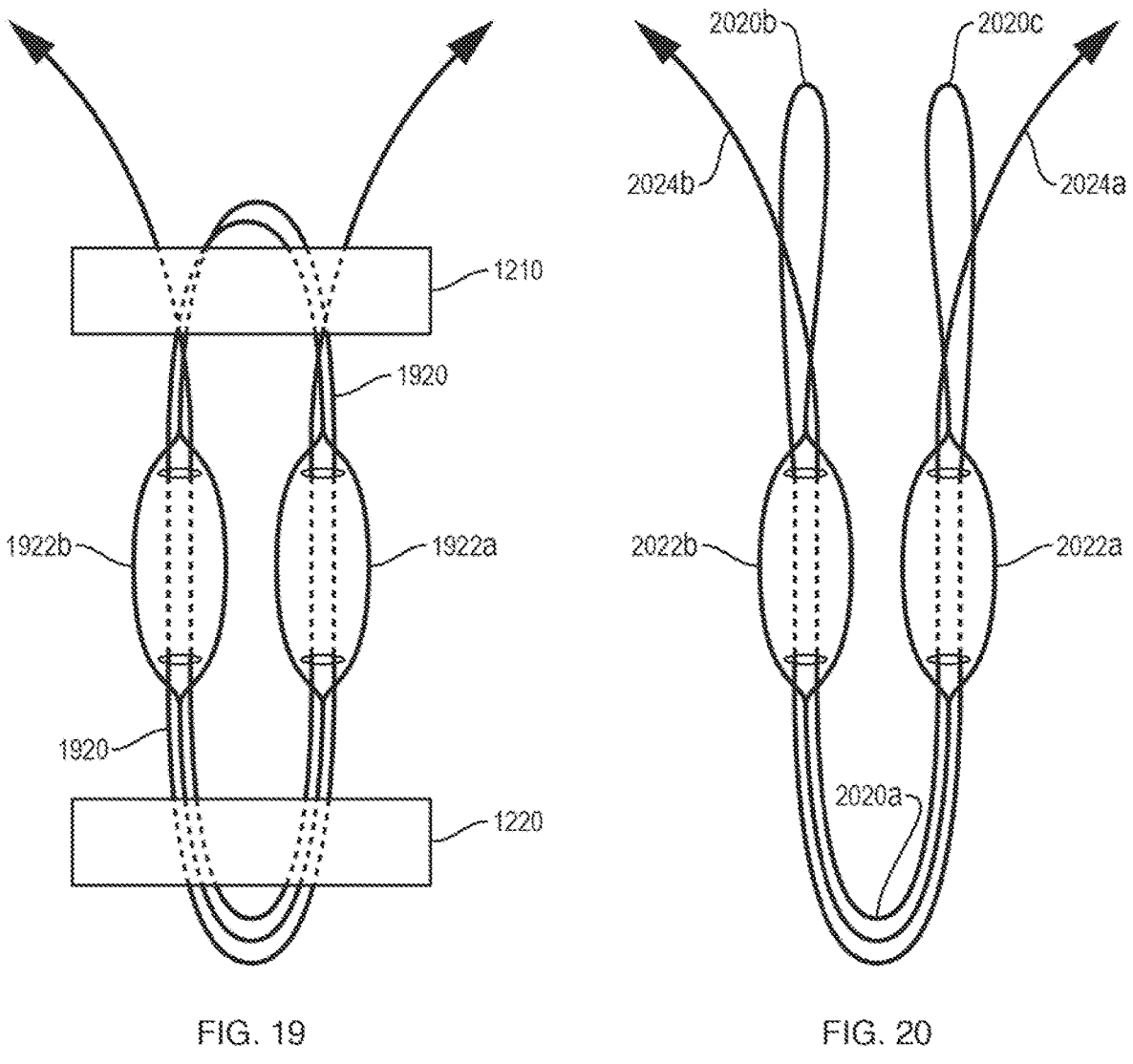
FIG. 19                  FIG. 20

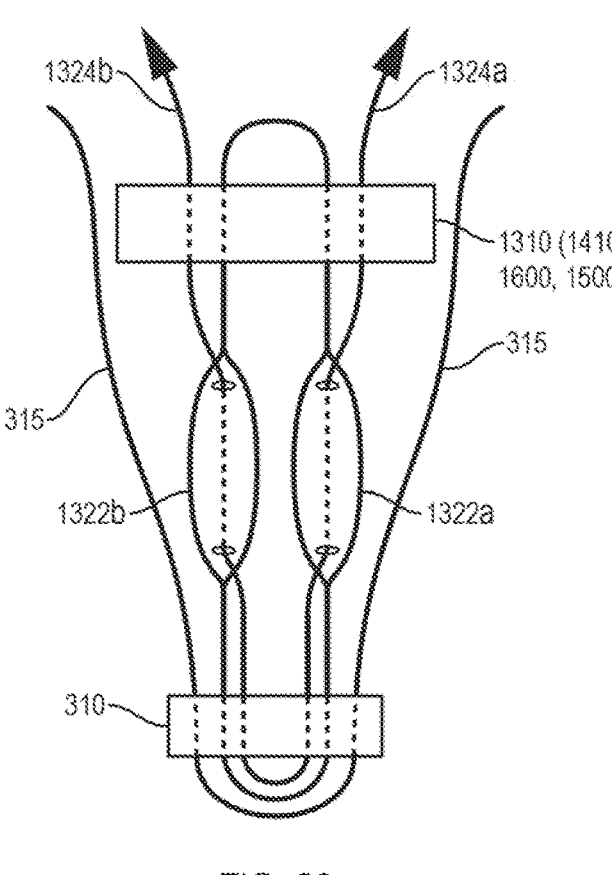
FIG. 22
FIG. 23
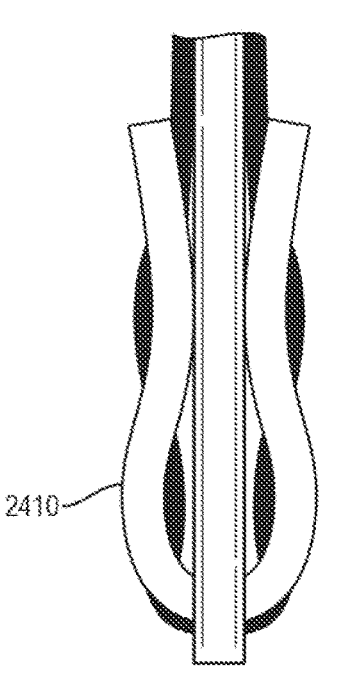
FIG. 24A
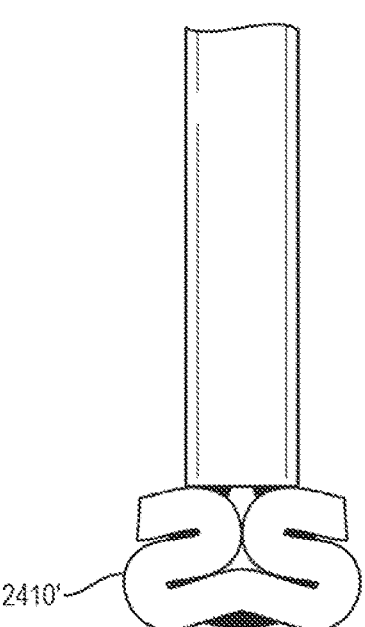
FIG. 24B

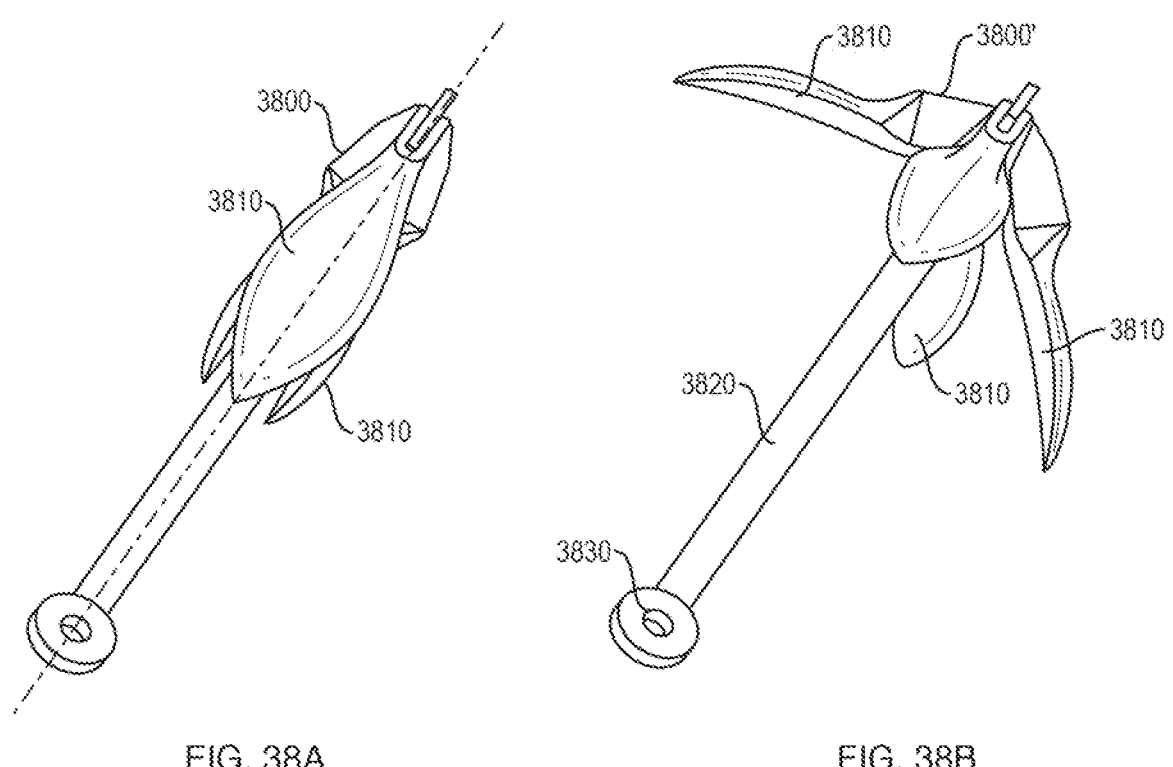
FIG. 38A
FIG. 38B
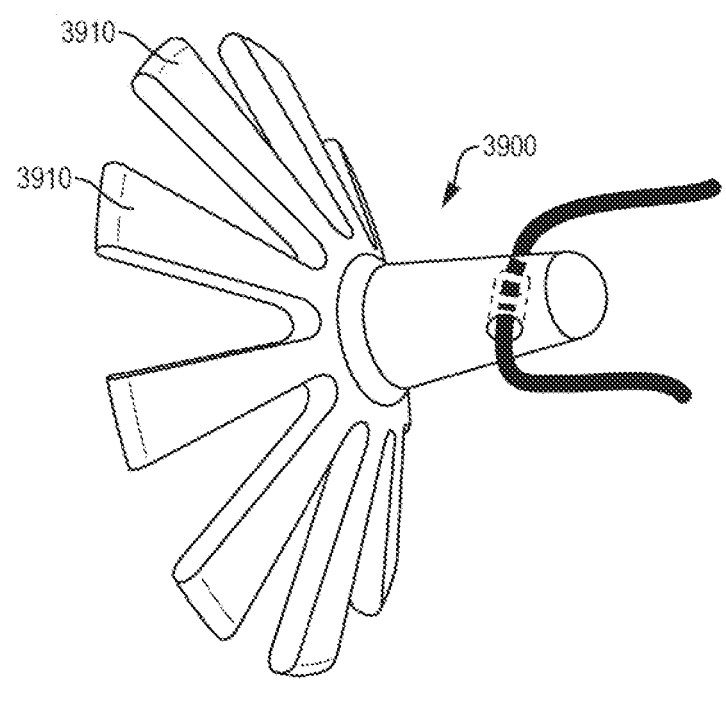
FIG. 39

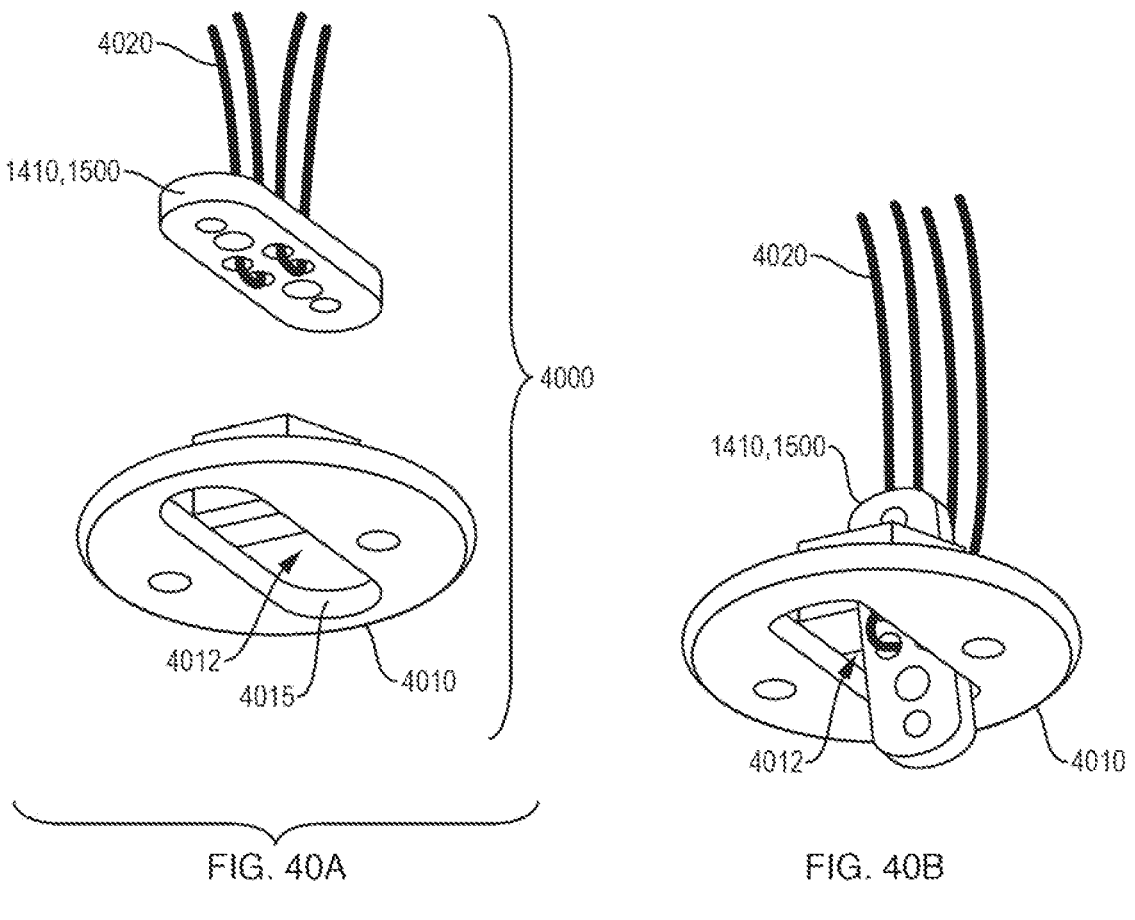
FIG. 40A
FIG. 40B
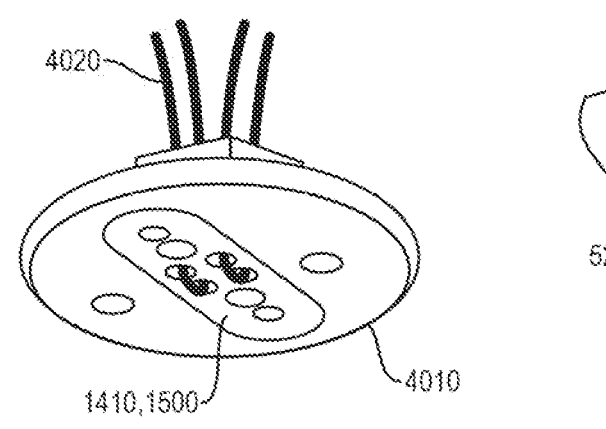
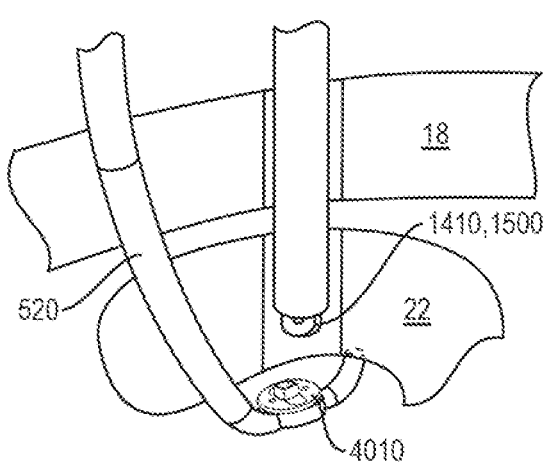
FIG. 40C
FIG. 40D

METHODS AND SYSTEMS RELATED TO JOINT REPAIR

CROSS-REFERENCE TO RELATED APPLICATIONS

This application is the U.S. national phase entry under 35 U.S.C. § 371 of International Application No. PCT/US2022/018897, filed Mar. 4, 2022, entitled "METHODS AND SYSTEMS RELATED TO JOINT REPAIR," which claims benefit and priority to Provisional Patent Application No. 63/156,431 filed Mar. 4, 2021, titled "METHODS AND SYSTEMS RELATED TO JOINT REPAIR", Provisional Patent Application No. 63/180,775 filed Apr. 28, 2021, titled "METHODS AND SYSTEMS RELATED TO JOINT REPAIR", Provisional Patent Application No. 63/196,538 filed Jun. 3, 2021, titled "METHODS AND SYSTEMS RELATED TO JOINT REPAIR" and to Provisional Patent Application No. 63/238,658 filed Aug. 30, 2021, titled "METHODS AND SYSTEMS RELATED TO JOINT REPAIR" and herein incorporated by reference in its entirety.

FIELD

The present disclosure relates to methods, kits and systems for repairing a joint within the body.

BACKGROUND

Damage to a joint can include tearing or disruption of one or more ligaments. Repair of damaged joints may include restoration of the physical connection between the bones of the joint, the restoration preferably placing the bones of the joint in a repaired arrangement that may be an anatomically correct relative positioning (anatomical repair). In some example repaired arrangements, portions of the joint may be close to the skin, making it easy to palpate or see fixation construct. Improved systems and methods of repair include fixation constructs that avoid being palpable or visible by the patient. Improved systems and associated methods may place bulky components or knots of fixation constructs in less palpable locations or alternatively avoid or minimize them altogether. In some systems and associated methods, fixation constructs may result in incisions and scarring in more conspicuous areas. It would be advantageous to provide a system and associated method that either moves the incisions to less conspicuous areas or reduces the size of incisions. In some example repairs, at least one of the preferred bones may be small or fragile. Furthermore, fixation to these smaller and more fragile bones may include removing bone tissue therefrom, to place fixation constructs therein or therethrough, exacerbating the problem. Improved systems and associated methods may therefore provide for a repair that minimizes or avoids removal of bone tissue from the more fragile or smaller bones. In some repairs, the joint undergoes significant physiological loading that may stretch the repair constructs used over time. Improved systems and associated methods may repair the joint with a fixation construct that provides the required flexibility for the joint to operate, while withstanding physiological loading.

As way of an example, in the Acromioclavicular (AC) joint, ligaments that may be torn or damaged may include the Coracoacromial ligament 11, Conoid ligament 16 and Trapezoid ligament 14, shown in FIG. 1. Severe cases may result in a superior migration of the clavicle 18 and/or the inferior migration of the scapula 20. Restoration of this joint requires restoring the physical connection between the clavicle 22 and some aspect of the scapula 20, in addition to holding these bones in a repaired arrangement (or anatomical repair). Repair of the AC joint today may place knots or bulky anchors on the superior aspect of the clavicle 22; a location palpable by the patient. Improved systems and associated methods of repair may therefore include fixation constructs that avoid knots or bulky anchors adjacent the superior aspect of the clavicle. In some systems and associated methods, fixation constructs may result in incisions or portals through the skin near the clavicle, which may create scarring in a conspicuous area. It would be advantageous therefore to provide a system and associated method that either moves the incisions to less conspicuous areas or reduces the incision size. AC joint repair may include fixation within or through the coracoid process, a smaller and fragile bone. Improved systems and associated methods may therefore provide for a repair that minimizes or avoids removal of tissue from the coracoid 18. The AC joint undergoes significant physiological loading that has been found to stretch or damage repair constructs over time. Improved systems and associated methods preferably connect the coracoid 22 to the clavicle 18 with a repair construct that provides the required flexibility for the AC joint to operate, while withstanding the physiological loading.

SUMMARY

Described herein are various improved methods, devices and kits for joint repair that couple at least bones. These bones may have become dislocated and migrated away from each other. These and other features and advantages will be apparent from a reading of the following detailed description and a review of the associated drawings. It is to be understood that both the foregoing general description and the following detailed description are explanatory only and are not restrictive of aspects as claimed.

Disclosed herein is a tissue repair construct that includes an adjustable loop construct formed of a flexible member. The adjustable loop construct includes a first loop end and a second loop end opposite the first loop end, a first locking passage and a second locking passage. Each passage defines a first passage end and a second passage end. First passage ends are closer to the first loop end than the second loop end. The two adjustable loops extend from both passage first ends and defines the first loop end. The adjustable loop construct also includes a saddle length, extending directly from both passage second ends and defining the adjustable loop second end. The saddle length is fixed in length. The adjustable loop construct also includes a first reduction end of the flexible member that extends from the second passage end of the first locking passage and a second reduction end of the flexible member that extends from the second passage end of the second locking passage. Both first and second reduction ends extend towards the second loop end. The tissue repair construct also includes a bone anchor slidingly coupled to the first loop end.

In some example tissue repair constructs, the bone anchor may be a cortical button anchor which may include a plurality of apertures therethrough, and each of the plurality of apertures may receive the two adjustable loops therethrough. In some example tissue repair constructs, the bone anchor may be a cortical button anchor with a concave bone engaging surface. In some example tissue repair constructs, the cortical anchor may have a cross section that is semi-circular. The cortical anchor cross section may match a contour of an inner bore surface of an insertion instrument shaft. The cortical anchor cross section may fill a circumferential half of a bore cross section of an insertion instrument shaft, leaving a remaining circumferential half free of the cortical anchor for housing the adjustable loop construct. The saddle length may operatively couple to a cortical anchor. Tension on the first and second reduction ends may reduce the two adjustable loops.

Another example tissue repair construct is disclosed including a first cortical button with a plurality of apertures therethrough. The construct also includes an adjustable loop construct formed with a flexible member. The adjustable loop construct includes two adjustable loops coupled to the first cortical button via the plurality of apertures. It also includes a first and a second locking passage separated from each other along the flexible member by a saddle length of the flexible member, the saddle length fixed in length. A first of the two adjustable loops are formed by threading a first end of the flexible member that extends from the first locking passage through two of the plurality of apertures and then through the second locking passage, the second of the two adjustable loops formed by threading a second end of the flexible member that extends from the second locking passage through two of the plurality of apertures and then through the first locking passage. A second cortical button maybe couples to the saddle length.

In some example tissue repair constructs, the plurality of apertures may include two apertures that each receive both of the two adjustable loops therethrough. The first cortical button may include a concave bone engaging surface. The first cortical button may have a cross section that is semi-circular, configured to fill a first half of a shaft bore of an insertion instrument, leaving a remaining half vacant to house the adjustable loop construct. The saddle length may define a single length of the flexible member, free of suture locking passages. The first end of the flexible member may extend directly from the first cortical button, through the second locking passage and emerge to define a first reducing end and the second end of the flexible member may extend through the first locking passage and emerge therefrom to define a second reducing end, the first and second reducing ends extending away from the first cortical button. The first cortical button may define an oblong footprint, and the second cortical button may define a circular footprint. The second cortical button may define a non-passing button with a single slot configured to receive the saddle length therein.

A method of forming a tissue repair construct is also disclosed, the tissue repair construct including a cortical button with a plurality of apertures therethrough, and a length of flexible member with a first and second end and a lumen therealong. The method includes drawing the first end through two of the plurality of apertures and then introducing the first end into the lumen at a first location along the length of the flexible member and then out of the lumen at a second location, defining a first adjustable loop coupled to the cortical button with the first end extending away from the cortical button. The method also includes drawing the second end through two of the plurality of apertures and then introducing the second end into the lumen at a third location along the length of the flexible member and then out of the lumen at a fourth location, defining a second adjustable loop coupled to the cortical button and the second end extending away from the cortical button. The second and fourth locations are spaced away from each other a fixed distance, defining a saddle length. The first and third locations are spaced away from each other an adjustable distance.

In some examples, the method may include looping the saddle length through a slot of another cortical button. The second and fourth locations may be spaced away from each other by less than 10 mm, measured along a longitudinal axis of the flexible member. The cortical button may be an oblong shape with a concave bone-engaging surface and a semi-circular cross section that fills a first half of an internal bore of an insertion instrument shaft.

A repair construct is disclosed herein, that holds two bones of a joint in a repaired configuration. The repair construct includes a flexible member construct with a first end and a second end defining a flexible member axial length of the repair. The repair construct also includes a first anchor that couples the flexible member to a first bone of the two bones, the first anchor having a first end and a second end, and a first anchor flexible member pulley disposed through the first end. The first anchor pulley couples to the flexible member first end. The repair construct also includes a second anchor that couples the flexible member to a second bone of the two bones, the second anchor having a first end and a second end, and a flexible member pulley disposed through the second anchor second end. The pulley of the second anchor is coupled to the second end of the flexible member construct. The repair construct defines a total axial length, and when in the repaired configuration, the first and second anchor flexible member pulleys are positioned axially adjacent each other, configured to limit the axial length of the flexible member, and thereby limiting elongation of the repair construct during physiological loading on the repair construct.

In some example tissue repair constructs, the first anchor and second anchor both are rigid and therefore have a higher resistance to elongation than that of the flexible member construct. The total axial length may include an axial length of the first anchor, an axial length of the second anchor and the flexible member construct axial length disposed therebetween, and wherein in the repaired configuration, the first and second anchor pulleys are axially adjacent each other along the axis of the repair construct, with the first and second anchor axial lengths extending away from the flexible member construct along the axis. The first anchor may be an all-suture anchor with a rigid pin extending therethrough, the rigid pin including the first anchor pulley. The first anchor may be inserted into and through a first external surface of the first bone to position the first anchor pulley adjacent the first external surface of the first bone. The second anchor may be a cortical button anchor with a flanged portion that engages a first external surface of the second bone, the second anchor having a post extending distally from the flanged portion and along a passage through the second bone and the second anchor pulley may place the flexible member construct second end adjacent a second external surface of the second bone. The flexible member construct may define an adjustable loop construct. The flexible member construct may define an adjustable loop construct that includes a locking passage. The first anchor may couple to the first bone while placing the pulley adjacent an external surface of the first bone and the second anchor may couple to the second bone while placing the pulley adjacent an external surface of the second bone, both external surfaces facing each other.

Another repair construct is disclosed for placing a flexible member construct between two bones of a joint. The repair construct includes a first bone anchor having a flexible member pulley at a first end of the first bone anchor to couple to a first end of the flexible linking construct. The repair construct also includes a second bone anchor defining a pulley at a first end of the second bone anchor, that couples to a second, opposing end of the flexible linking construct.

The first and second bone anchors engage, one each with a first and second bone of the two bones respectively, and place the flexible linking construct between facing surfaces of the two bones with the pulleys of each bone anchor body directly adjacent the facing surfaces. This defines a limited length of the flexible member construct, the limited length having a lower limit to provide sufficient flexibility to the joint upon repair, and an upper limit configured to limit elongation of the repair construct due to physiological loading on the joint over time.

In some example tissue repair constructs, the first and second bone anchor both are more rigid and therefore have a higher resistance to elongation than that of the flexible linking construct. The first bone anchor may be inserted into a first facing surface of the facing surfaces and position the first bone anchor pulley adjacent the first facing surface of the first bone. The second bone anchor may be a cortical button anchor with a flanged portion that engages a first external surface of the second bone, and post extending distally from the flanged portion along a passage through the second bone and wherein the second bone anchor pulley extends transversely through the post and adjacent the second facing surface of the facing surfaces. The flexible linking construct may be an adjustable suture loop construct. The flexible linking construct may be an adjustable loop construct that includes a locking passage.

In addition, a method of placing a first and a second bone of a joint in a repaired configuration with a repair construct is disclosed, the repair construct including a flexible member construct. The method includes fixing a first loop end of the flexible member construct with the first bone, the first loop end disposed within a passage through the first bone and terminating directly adjacent an external surface of the first bone. The method also includes fixing a second loop end of the flexible member construct with the second bone so as to place the second loop end within a passage through the second bone and with the second loop end terminating directly adjacent an external surface of the first bone. Both external surfaces of each bone are facing each other.

The repair construct may include a first anchor operatively coupled to the first loop end of the flexible member construct at a first end of the first anchor, and wherein fixing comprises inserting the first anchor along the passage through the first bone, the inserting placing the first end of the first anchor adjacent the external surface of the first bone. The repair construct may include a second anchor operatively coupled to the second loop end of the flexible member construct at a first end of the second anchor, and fixing may include inserting the second anchor along the passage through the second bone, the inserting placing the second end of the second anchor adjacent the external surface of the second bone. The method may include tensioning at least one limb of the flexible member construct to reduce a loop length of the flexible member construct. The method may include locking the flexible member construct to fix the distance between the first and second bone. Locking may include tying a knot in the flexible member construct and recessing the knot. The repair construct may include a first anchor operatively coupled to the first loop end of the flexible member construct, and fixing may include inserting the first anchor through the passage through the second bone and then along the passage through the first bone. The repair construct may include a second anchor operatively coupled to the second loop end of the flexible member construct, and fixing may include inserting the second anchor first through the second bone passage towards the external surface of the second bone.

Another repair construct for holding two bones of a joint in a repaired arrangement is disclosed, the repair construct anchoring with a first of the two bones at a first anchoring end of the repair construct and anchoring with a second of the two bones at a second anchoring end of the repair construct. The repair construct includes a flexible member coupled to a first and second bone anchor at the first anchoring end of the repair construct, the flexible member configured to operatively couple to a third bone anchor at the second anchoring end. The first and second bone anchors are configured to anchor the first anchoring end of the repair construct at a single passage exit of a passage through the first bone.

In some example repair constructs, the flexible member may include a first adjustable loop coupled to the first bone anchor and a second adjustable loop coupled to the second bone anchor. The first and second bone anchors may be sized to pass sequentially through the passage through the first bone. Both the first and second bone anchors may each define a width, limited to fit through the passage, and wherein each width defines a corresponding footprint width of each of the first and second bone anchor in a deployed configuration, and wherein both footprint widths in combination are configured to provide sufficient anchoring at with the second bone. The first and second bone anchors may be housed in an axially aligned arrangement within an insertion instrument distal end. The flexible member may be formed as an adjustable loop construct, such that tension on at least one limb of the flexible member is configured to reduce a distance between the first and second anchoring ends. The flexible member may form a first adjustable loop extending through the first bone anchor, and also a second adjustable loop extending through the second bone anchor and wherein each adjustable loop may be sequentially reduced.

Another repair system for repairing two bones of a joint is disclosed, including a repair construct including a flexible member with a first anchoring end for anchoring with a first of the two bones and a second anchoring end for anchoring with a second of the two bones. The system also includes a first and second anchor coupled to the first anchoring end and a third anchor that may couple the second anchoring end to the first of the two bones. The system also includes an insertion instrument with a handle and a shaft extending distally therefrom. The shaft has a distal end that houses the first and the second anchor therein and the handle may retain the first anchoring end.

In some example repair systems, the flexible member includes a first loop coupled to the first anchor, and a first locking passage extending from the first loop. The flexible member may also include a second loop coupled to the second anchor, the second loop extending from a second locking passage. The system may be used to pass the two anchors, sequentially through the passage of the second bone. The insertion instrument may deploy both the first and second anchors at a single passage exit of the first bone. The first and second anchors may be housed in an axially aligned arrangement within an insertion instrument distal end. The flexible member may form an adjustable loop construct, and tension on the flexible member reduces a distance between the first and second anchoring end.

A method of repairing a joint is also disclosed, the repairing with a system including a first anchor and a second anchor coupled to a flexible member. The method includes placing the first and second anchors through a passage through a first bone of the joint and deploying both the first and second anchor at a single exit opening of the first bone passage and thereby coupling the repair construct to the first bone.

The method may also include inserting an insertion instrument, housing the first and second bone anchors through a second bone and then through the first bone. The first and second anchors may deploy sequentially at the single exit opening. The first anchor alone may define an anchor stress concentration on the first bone, the second anchor configured to combine with the first anchor and reduce an overall anchor stress concentration to a value below a maximum allowable stress concentration limit of the first bone. The method may also include coupling a third bone anchor to the flexible member and anchoring the third bone anchor with a second bone of the joint. Tension may be applied to the flexible member to reduce a first loop of the flexible member operatively coupled to the first anchor and also to reduce a second loop of the flexible member operatively coupled to the second anchor, and thereby reduce a length of the repair construct. Tensioning the flexible member may lock a first locking passage formed by the flexible member and may also lock a second locking passage formed by the flexible member, and thereby knotlessly locking the repair construct. The system may include an insertion instrument that houses the first and second anchor at an insertion instrument distal end and retains a portion of the flexible member at a handle end of the insertion instrument. After deploying the first and second anchor, the method may include releasing the portion of the flexible member from the handle end, coupling a third anchor to the portion, and anchoring the third anchor to a second bone of the joint.

A method of holding a clavicle and a coracoid of an AC joint in a repaired configuration with a repair construct is also disclosed, the repair construct including an adjustable suture loop having a first loop end preassembled to a cortical anchor and also a second loop end, free of the cortical bone anchor. The method includes placing the second loop end through a clavicle passage, around an inferior surface of the coracoid and then through the clavicle passage again. The method also includes placing the second loop end through a first and a second slot of the cortical anchor and thereby assembling the second loop end to the cortical anchor with the second loop end wrapped around the coracoid. With the second loop assembled the method continues to include reducing the adjustable loop to hold the clavicle and coracoid in the repaired configuration.

The method may include passing at least one locking passage of the adjustable suture loop through the clavicle. Placing the second loop end through the clavicle passage may also pass a locking passage through the clavicle and under the coracoid. While reducing, the locking passage may remain stationary and engaged with the coracoid inferior surface. The method may also include knotlessly locking a locking passage of the adjustable suture loop after reducing the adjustable suture loop. Reducing may include tensioning two limbs of the suture. Placing the second loop end through a clavicle passage may dispose the first loop into and along the clavicle passage. The adjustable suture loop may include a locking passage with two lengths of the suture extending therethrough and reducing the adjustable suture loop may slides both lengths of the suture through the locking passages, in opposing directions.

Another example method of holding a clavicle and a coracoid of an AC joint in a repaired configuration with a repair construct is disclosed. The repair construct includes an adjustable suture loop construct with a first adjustable loop preassembled to a cortical anchor, a second adjustable loop preassembled to a cortical anchor, a second adjustable loop, free of the cortical bone anchor, and a locking passage between the two adjustable loops. The method includes passing the second adjustable loop and the locking passage through a clavicle passage and around an inferior surface of the coracoid and then through the clavicle passage a second time. The method also includes coupling the second adjustable loop end to the cortical anchor after passing the second loop a second time, and, with the second loop coupled, reducing the adjustable suture loop construct to reduce both the first and second adjustable loops.

Some example methods may include placing the locking passage on the coracoid inferior surface. While reducing, the locking passage may engage the coracoid inferior surface. The method may include knotlessly locking the locking passage after reducing the adjustable suture loop construct. Reducing may include tensioning two limbs of the suture. Placing the second adjustable loop end through a clavicle passage may place the first adjustable loop into the clavicle passage. The locking passage may include two lengths of the suture extending therethrough and reducing the adjustable suture loop construct may slide both lengths of the suture through the locking passage, in opposing directions.

Another method of holding a clavicle and a coracoid of an AC joint in a repaired configuration with a repair construct is disclosed, the repair construct including an adjustable suture loop construct with a first adjustable loop preassembled to a cortical anchor, a second adjustable loop, free of the cortical bone anchor, and a locking passage between the two loop end. The method includes passing the second adjustable loop and the locking passage through a clavicle passage, around an inferior surface of the coracoid and through another passage through the clavicle. The second adjustable loop may then be coupled to the cortical anchor after passing the second adjustable loop through the other passage. With the second adjustable loop coupled, the adjustable suture loop construct is reduced to draw the cortical anchor to engage a superior clavicle surface.

The method may include placing the locking passage on the coracoid inferior surface. While reducing, the locking passage may remain engaged with the inferior surface of the coracoid. The method may include knotlessly locking the locking passage after reducing the adjustable suture loop construct. Reducing may engage the cortical anchor with the superior clavicle surface between the clavicle passage and the other clavicle passage.

BRIEF DESCRIPTION OF THE DRAWINGS

The disclosure will be more fully understood by reference to the detailed description, in conjunction with the following figures, wherein:

FIGS. 9A-9B illustrate a method of placing an anchor through the clavicle and within the coracoid, in accordance with this disclosure;

FIG. 10 illustrates a repair construct assembled to an AC joint, in accordance with this disclosure;

FIG. 11A illustrates a guide tool for forming at least two tunnels at a target location and trajectory within a bone, in accordance with this disclosure;

FIG. 11B illustrates a close up of guide tool illustrated in FIG. 11A, in accordance with this disclosure;

FIG. 12 illustrates a repair construct, in accordance with this disclosure;

FIG. 13 illustrates an adjustable repair construct, in accordance with this disclosure;

FIG. 15A illustrates a perspective view of a cortical button embodiment, in accordance with this disclosure;

FIG. 15B illustrates an end view of the cortical button embodiment shown in FIG. 15A within a shaft bore of an insertion instrument, in accordance with this disclosure;

FIG. 15C illustrates a bottom view of the cortical button embodiment shown in FIG. 15A, in accordance with this disclosure;

FIG. 15D illustrates a view of the cortical button embodiment shown in FIG. 15A, within a shaft bore of an insertion instrument in accordance with this disclosure;

FIG. 19 illustrates an adjustable repair construct, in accordance with this disclosure;

FIG. 20 illustrates an adjustable repair construct, in accordance with this disclosure;

FIG. 22 illustrates an adjustable repair construct, in accordance with this disclosure;

FIG. 23 illustrates an adjustable repair construct, in accordance with this disclosure;

FIGS. 24A-24B illustrates an alternative all-suture anchor in an elongate and deployed configuration respectively;

FIG. 38A illustrates an expanding anchor in a folded configuration, in accordance with this disclosure;

FIG. 38B illustrates an expanding anchor in an expanded configuration, in accordance with this disclosure;

FIG. 39 illustrates another expanding anchor in an expanded configuration, in accordance with this disclosure;

FIGS. 40A-40D illustrates a two-piece button anchor and associated method, in accordance with this disclosure;

DETAILED DESCRIPTION

Figure 1:
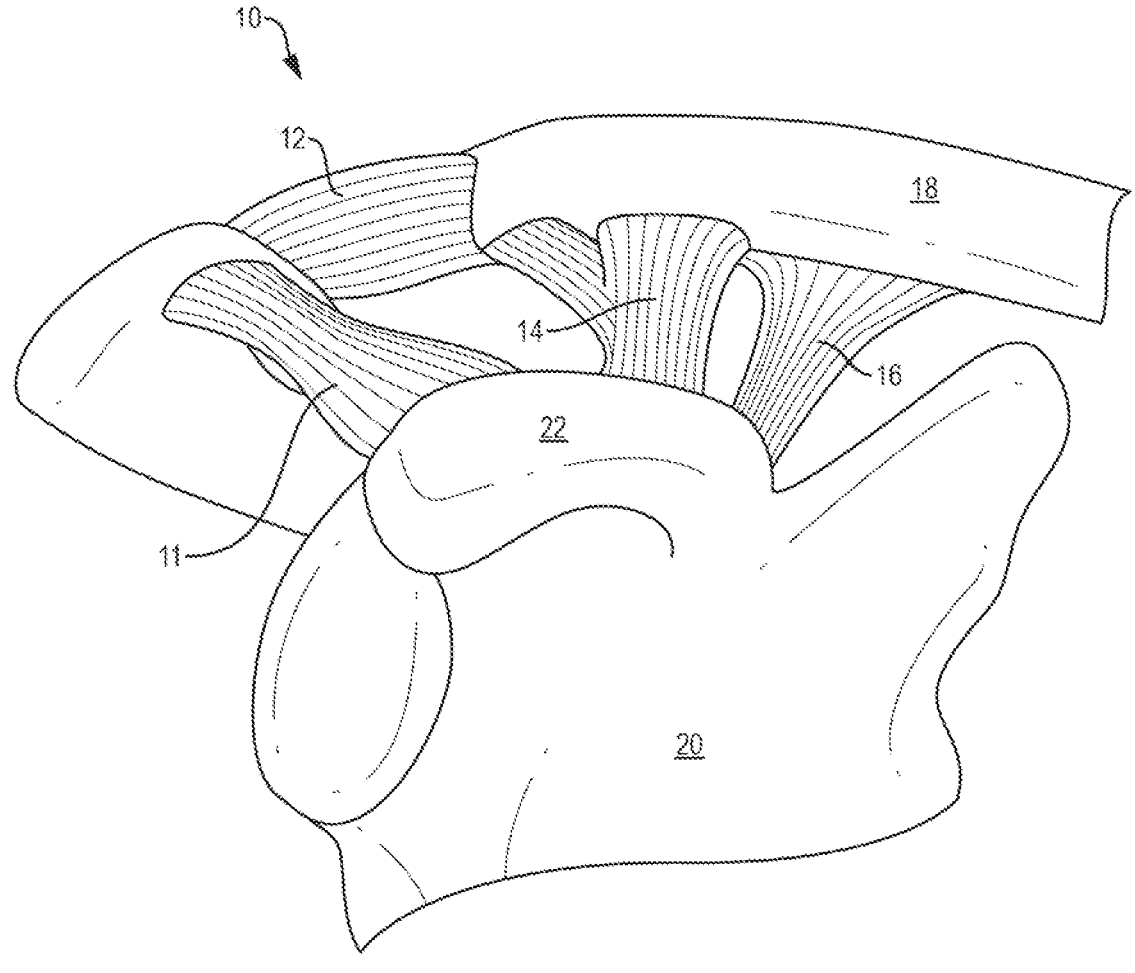
FIG. 1 illustrates the anatomy of the shoulder for reference purposes.

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts. Use of the terms "upper," "lower," "upwards," and the like is intended only to help in the clear description of the present disclosure and are not intended to limit the structure, positioning and/or operation of the disclosure in any manner.

Some of the constructs disclosed herein incorporate "locking passages". These may sometimes be referred to in the art as splices, eyesplices, cradles, suture locking regions, suture locking regions, cinches, finger cinches, finger traps, longitudinal passages or dilated regions. They are defined by a length of a braided flexible member with a hollow core that may receive an elongate member therethrough. The elongate member may be a different portion of the flexible member, or another flexible member and may extend along a path that extends from outside the braided flexible member (and outside the locking passage) then between the braids to enter the hollow core (lumen) and then exit through the braided wall a distance along the flexible member later. Multiple lengths of flexible members may extend along and through the hollow core at spaced apart locations, thereby defining multiple locking passages. Multiple lengths of elongate member or flexible members may extend along and through the hollow core at the same location. The braided flexible member may be dilated first to form a dilated or laterally extended length before receiving the elongate member therein. The elongate member inserted may be rigid member such as a metal wire or tube. The locking passage is configured such that tension on the braided hollow flexible member contracts the radius of the braided hollow flexible member and thereby locks or cinches around the elongate member extending therein, locking it in place. This defines a "locking passage". The flexible member or strand may be a suture, suture tape, ribbon, flexible wire or cable.

FIG. 1 illustrates the anatomy of the shoulder joint 10, for reference purposes. Included are the AC ligament 12, trapezoid ligament 14 and conoid ligament 16, all of which may be damaged or torn. During AC joint repair, the clavicle 18 may be reattached to the coracoid process (hereinafter "coracoid") 22 of the scapula 20. During the repair, the clavicle 18 may be relocated relative to the coracoid 22. This is oftentimes referred to as reducing the joint.

Disclosed herein are a plurality of repair constructs that may hold two bones of a joint in a preferred location relative to each other, or a repaired arrangement. The two bones may be two different bones, or in some cases, two portions of the same bone. During the repair, the two bones may first be moved or reduced to be in a target repaired arrangement relative to each other before assembling the repair construct thereto. For example, during AC joint repair, the repair may include moving and fixing the coracoid 22 relative to the clavicle 18. Repair constructs disclosed herein may be applicable to other repairs, such as ACL repair, ankle syndesmosis or shoulder repair such as the Latarjet procedure. Illustrated in FIG. 12 is an example repair construct 1200. In general, the repair construct 1200 may include a first anchoring means 1210 and a second anchoring means 1220 with a coupling member 1230 disposed therebetween. Coupling member 1230 is operatively coupled to the first and second anchoring means 1210, 1220. Coupling member 1230 may be flexible and may form a plurality of loops. Coupling member 1230 may be formed from a flexible member such as but not limited to suture, suture tape, wire, ribbon, or cable. Optionally a locking means 1240 be associated with the coupling member 1230 and may be disposed between the two anchoring means 1220, 1230. Locking means 1240 may include a pre-tied knot. Locking means 1240 may include plugs or inserts that are drawn into the anchors (1210, 1220) or into the flexible member 1230 to restrict relative axial motion of the two anchoring means 1210, 1220. Locking means 1240 may include a locking passage, as defined herein.

The first and second anchoring means 1210, 1220 may each include at least one bone anchor, such as a cortical button, interference screw, rigid anchor or a soft flexible (all-suture) anchor. For example, the first anchoring means 1210 may include one soft anchor and one interference screw, coupled to different locations along a first bone. The second anchoring means 1220 may include a cortical button, interference screw, rigid anchor, or a soft flexible (all-suture) anchor. First and second anchoring means 1210, 1220 may be the same as each other, or different in quantity, material, shape, or deployment methods. Anchoring means 1210, 1220 may remain external to a target anchoring bone, or may be disposed at least partially within the target anchoring bone. A first anchoring means 1210 may include a soft anchor that may deploy outside the target bone and therefore engage an external cortical surface thereof; or soft anchor may engage tissue within a tunnel through the target bone. For example, the soft anchor may engage an inferior external surface of a coracoid. A second anchoring means 1220 may include another soft anchor that may be disposed within or on an external surface of a second target anchoring bone. The second anchoring means 1220 may include two anchors. More specific example embodiments of construct 1200 are disclosed herein.

Figure 2:
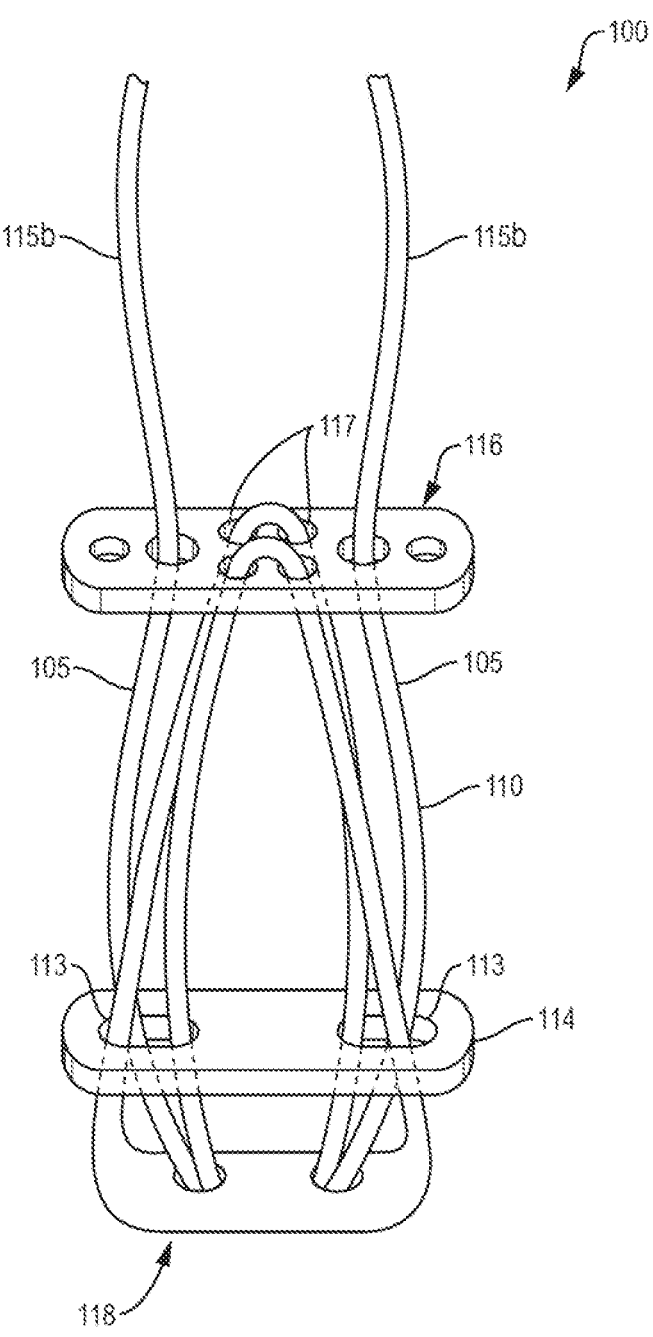
FIG. 2 illustrates an embodiment of a double button adjustable loop construct, in accordance with this disclosure.

An example repair construct 1200 is shown in FIG. 2, illustrating an adjustable repair construct 100 that may reduce and hold the coracoid 22 of the scapula 20 relative to the clavicle 18 in a repaired arrangement. Repaired arrangement may be synonymous with a reduced arrangement or anatomical reconstruction. FIG. 2 is an adjustable loop repair construct, wherein the repair construct includes a flexible member 105 forming two adjustable loops 110, adjustable to reduce the distance between a first anchor 114 and second anchor 116. More specifically tension on flexible member ends 115a and 115b may reduce the loops 110 and draw anchors (114, 116) towards each other. In this example construct 100, first and second anchors 114, 116 may be cortical button style anchors. First and second anchors 114, 116 may be contoured to match the corresponding outer bone surface that they are configured to engage (similar to anchor 1500 for example). For example, each anchor (114, 116) may define a surface that has a concave surface. Concave surface of anchor 114 may be different from concave surface of anchor 116. The two concave surfaces may face each other. Each concave surface may define a different inner curve radius or profile, configured to match an outer contour of a corresponding bone. By way of an example, anchor 114 may have a concave surface with a first radius of curvature, configured to match an outer profile of an outer radial surface of the superior clavicle bone. Anchor 116 may have a concave surface with a second radius of curvature, different than the first radius if curvature, configured to match an outer profile of an outer radial surface of the smaller coracoid inferior bone surface.

Each anchor 114, 116 may include a plurality of apertures for passage of at least one length or strand of flexible member 105 therethrough. Anchor 114 is shown with a single pair of apertures 113, with three strands of the flexible member 105 therethrough. In other embodiments, slots or apertures 113 may each receive a single strand, which may reduce binding of the flexible member strands as they move relative to each other. Anchor 116 may include a plurality of smaller apertures 117. The loops 110 may also include a locking passage 118, as defined herein. Locking passage 118 may include two strands of flexible member 105 extending therethrough, in opposite directions. Tension on the ends 115a and 115b may operate in a manner similar to a finger cinch and reduce the diameter of the construct 118 and thereby lock the repair construct 100 in place without the need to tie a knot. Flexible member loops 110 may be formed by a hollow length of flexible member 105. The adjustable loops 110 are arranged in a manner disclosed in more detail in U.S. Pat. No. 10,383,617, herein incorporated by reference in its entirety.

Figure 3A:
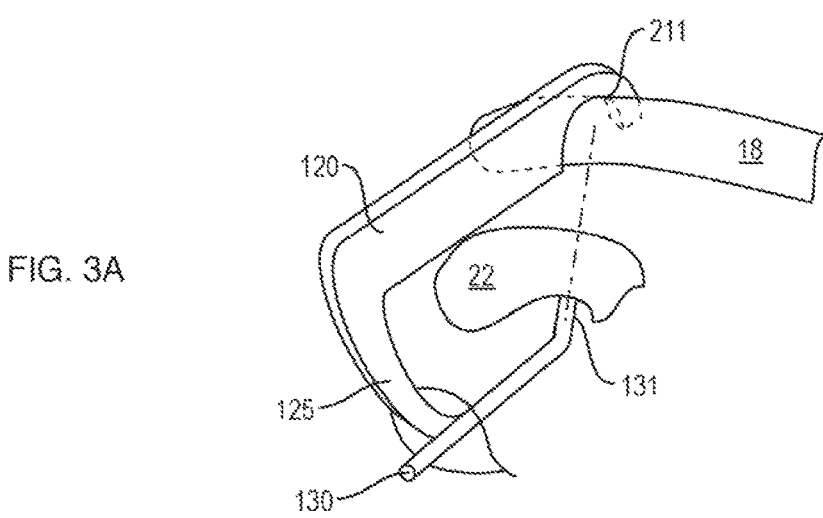
FIGS. 3A-3C illustrates a method and system for AC joint repair, in accordance with this disclosure.
Figure 3B:
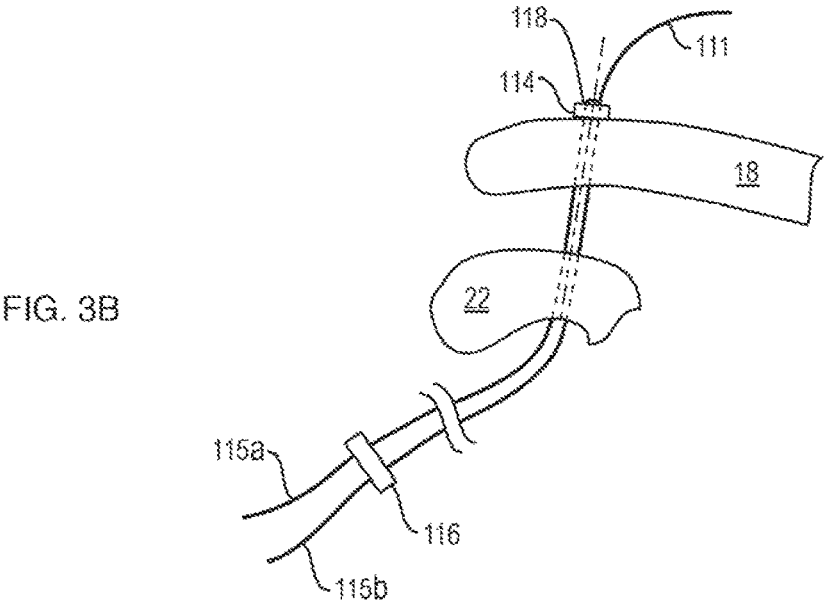
Figure 3C:
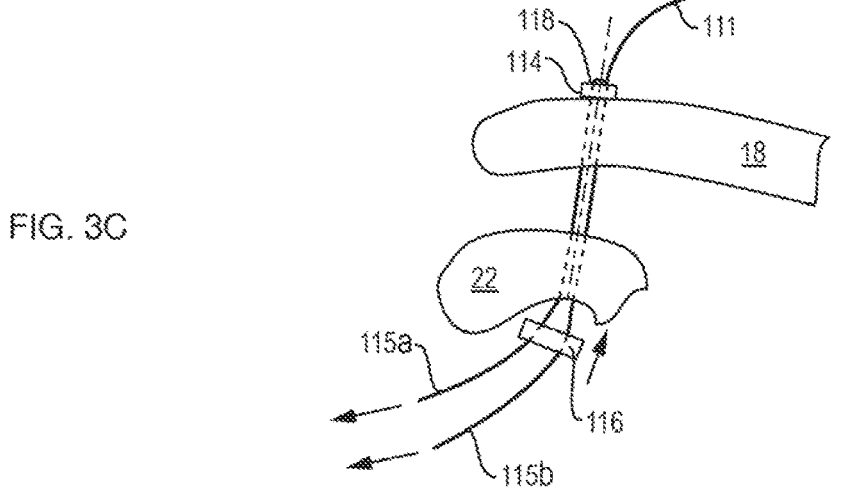

A method of repairing an AC joint with adjustable repair construct 100 is illustrated in FIGS. 3A-3C. Advantageously this method may include installing construct 100 from an anterior/inferior side of the joint, avoiding or reducing a superior incision near the clavicle. This method may reduce the profile of material standing proud of the superior clavicle surface and thereby reduce palpability of the construct 100. This method may insert the clavicle anchor 114 from the anterior portal, through the coracoid 22 first and then through the clavicle 18 to place anchor 114 on the superior surface of the clavicle 18.

Starting with FIG. 3A, the method may include placing a stabilizing clamp or arm 120 of a guide system 125 on a superior outer surface of skin of the patient, and on top of the clavicle 18 (skin not shown). The clavicle stabilizer arm 120 may reduce the clavicle 18 to the correct anatomic position or stated another way, hold the clavicle 22 in the correct physical relationship (repaired arrangement) to the coracoid 22. The clavicle stabilizer arm 120 may stabilize the clavicle 18 in the anterior-posterior direction. Guide system 125 may also include a curved drill guide 130 configured to operably couple to the guide 125. The curved drill guide 130 may be inserted through a standard anterior portal and placed on the inferior surface of the coracoid 22. Curved drill guide 130 may include an angular offset end 131 that engages an inferior surface of the coracoid 22. The angular offset end 131 is configured to orient a drill (not shown) inserted within the drill guide 130 through the coracoid 22 and towards the stabilizer arm 120. More specifically stabilizing arm 120 may include a cavity 121 configured to receive a drill therethrough. Angular offset end 131 is offset to direct the drill path (shown as a dashed line) towards the target cavity 121. Drill may then form a tunnel through both the coracoid 22 and clavicle 18 that is axially aligned. The drill may puncture the patient's skin to enter the cavity 121.

Turning now to FIG. 3B, guide 125 and arm 120 may be removed and a suture passer (not shown) may be shuttled though the formed bone tunnels (through both the clavicle 18 and coracoid 22). This may then capture and draw the adjustable construct 100 superiorly, through the bone tunnels Button 114 may be drawn through the coracoid 22 first, followed by the clavicle 18. At least one flexible member 111, which may be a suture (two shown) may be coupled to anchor 114, engaged by the suture passer to draw the construct 100 through the tunnels. The at least one flexible member 111 may be preferably separately formed from the flexible member 105. Rocking tension on the at least one flexible member 111 may manipulate the first anchor 114 in place and then flip or deploy it to engage the superior surface of the clavicle 18. Flexible member 111 may be removed after deployment of anchor 114. In FIG. 3B, first anchor 114 is shown deployed, with suture locking passage 118 on a superior side of anchor 114. Anchor 114 may include a recess (not shown) on the anchor superior surface to nest the suture locking passage 118 within the anchor 114 and reduce palpability. FIG. 3B shows second anchor 116 and reduction suture ends 115a, 115b yet to be engaged.

Drawing on ends 115a, 115b may then reduce the adjustable loops 110 and draw the second anchor 116 towards the inferior coracoid outer surface, shown in FIG. 3C. Further tension may draw the two bones towards each other, and lock the suture locking passage 118, as disclosed herein. A knot (not shown) may then be tied to supplement locking of the repair construct 100, the knot being disposed adjacent the second anchor 116. Having the suture locking passage 118 reduces the need for a knot on top of the clavicle superior surface and reduces overall palpability of the repair construct 100. This method also reduces a skin incision, superior to the clavicle 18.

A kit for repairing an AC joint may include a guide 125 having a stabilizer arm 120, curved drill guide 130, a suture passer and an adjustable repair construct 100 having at least one suture locking passage 118 for knotlessly locking the adjustable repair construct 100. The adjustable repair construct 100 includes two anchors 114, 118 that may be provided pre-assembled. The stabilizer arm 120 may be configured to engage and hold the clavicle 18 in a reduced position. The curved drill guide 130 may inserted through a passage of the stabilizer arm 120. The curved drill guide 130 may be configured to guide a curved drill first through the coracoid 22 and then through the clavicle 18. The curved drill guide 130 may be configured to guide a drill from an anterior and inferior side of the repair, and therefore forms the coracoid tunnel first. The kit may advantageously reduce an incision size on the superior clavicle side of the patient's skin.

The specification now turns to example repair constructs that may include at least one all-suture anchor. Advantageously these repair constructs may keep a larger portion of coracoid bone intact, by reducing the coracoid tunnel in both diameter and length. When passing a button-style anchoring device through a bone tunnel, there is still a minimum tunnel diameter requirement to pass the button therethrough (discussed in more detail later). Anchoring devices such as the all-suture anchor 310 shown in FIG. 4A may be inserted into a bone hole that is considerably smaller than rigid anchors for a similar anchoring strength. For example, this all-suture anchor 310 may anchor within a hole that is 2.8 mm in diameter and may have similar anchoring strength (able to withstand similar loading) as a button style anchor that has a minimum dimension approximately 3.5 mm and therefore requires a bone tunnel diameter that is 3.5 mm. In addition, an all-suture anchor may embed within a blind hole, thereby extending only partially through the target anchoring bone, and therefore leaving more coracoid tissue remaining than a complete through-passage. With smaller bones, such as the coracoid 22, saving bone material may be crucial to repair success.

Figure 4B:
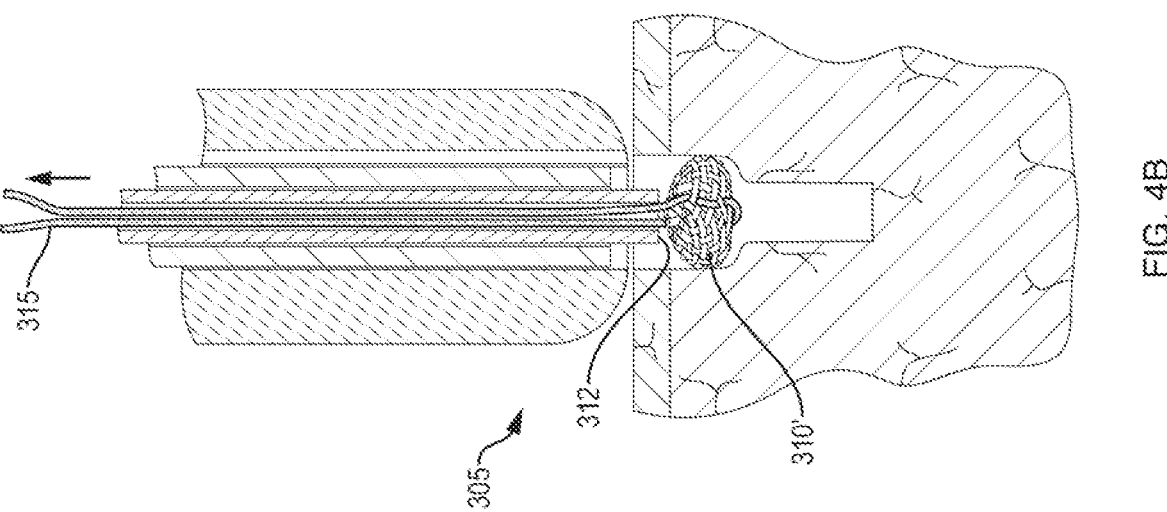
FIG. 4B illustrates the all-suture anchor system with a deployed anchor, for reference purposes.
Figure 4A:
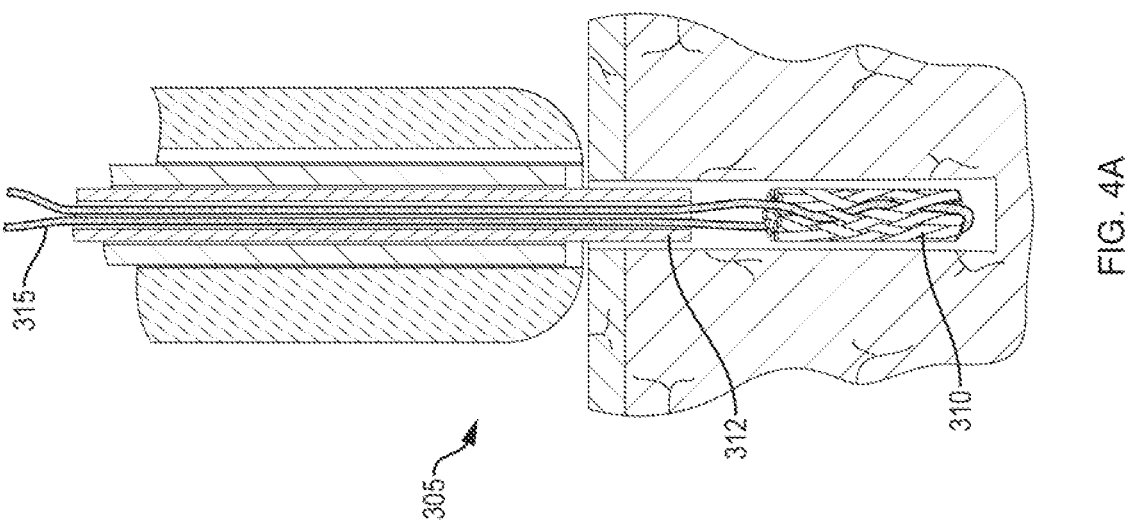
FIG. 4A illustrates an all-suture anchor system for reference purposes.

FIGS. 4A and 4B illustrate operation of an example all-suture anchor system 305. FIG. 4A shows the system 305 in an elongate configuration for inserting into bone; FIG. 4B in a deployed configuration. In the deployed configuration, the anchor 310 may be embedded within the target bone such as the coracoid bone 22. In other methods, anchor 310 may be inserted all the way through the target bone and deployed on the far side of the bone (described later). While AC joint repair with an all-suture is not tied to this particular configuration of all-suture anchor 310, this anchor configuration offers a high anchoring strength for a small anchor size and is therefore particularly advantageous for the smaller more fragile coracoid 22. This is due to both the anchor configuration and also the active deployment of this anchor 310, as disclosed in at least U.S. Pat. No. 9,962,149, commonly owned and herein incorporated in its entirety. The anchor 310 deploys into a tight bundle, bunched up into itself from all directions to form an ovoid shape, although this depends at least partially on the hardness of the target bone. Deployment of the anchor 310 is configured to eliminate most of or all of any resident void volume within the deployed anchor bundle, resulting in a tightly bunch up volume of anchoring material. A deploying suture 315 (or equivalent flexible member) is threaded through and around the anchor 310, and during deployment this suture 315 acts similar to a drawstring, to bunch up and deploy the anchor 310'. Active deployment tensions the suture to a target tension, that may be 140 Newtons. Active deployment also utilizes a backstop tube 312 that maintains a location of the anchor 310 within or external to the bone hole as tension is applied to the deploying sutures 315. A controlled, consistent, and relatively high level of tension may then be applied to the deploying sutures 315, as the backstop prevents the anchor 310 from inadvertently moving. This bundles the anchor 310 up against the backstop 312 into a more rigid oval, bundle shape that may sturdily embed with the target bone. This high tension also takes up some elongation (strain) on the deploying sutures 315, which may provide stronger chronic repair. As explained later herein, during physiological loading of the shoulder postoperatively, the repair construct including sutures 315 may undergo cycling (with shoulder movement) which can tend to elongate flexible members/coupling members extending between the two anchoring positions and thereby loosen the repair construct over time. By taking up some of this flexible member elongation in the suture 315, via higher tensions during active deployment, this loosening may be avoided or reduced. Suture 315 may alternatively be a wire or suture tape that better resists elongation. All-suture anchor 310 and active deployment are disclosed more detail in at least U.S. Pat. No. 9,962,149, commonly owned and herein incorporated in its entirety.

FIG. 5A-5K illustrates a system 500 that may be used to place an anchor such as all-suture anchor 310 through a first bone and embed the anchor 310 within a second bone tissue at a controlled depth. Typically, when placing anchors 310 within a target bone, the external surface directly adjacent the anchor's entrance into the target bone is relied upon as a reference, into which a depth of insertion is measured from. For example, typically a cannula or bullet distal edge may engage an outer surface at a target entrance to the target bone and the anchor is placed a target depth into the bone therefrom. In some repairs however, access to the target bone may be restricted, overly intrusive or not reasonably available. As a more specific example, when placing an anchor within the coracoid 22 during an AC joint repair, the option of placing a cannula or bullet distal edge on the coracoid 22 may require removal of excessive material from the clavicle 18, or excessive dissection around the coracoid 22. Therefore, a system that repairs the AC joint while avoiding removing excessive material is advantageous. These systems and associated methods may avoid gaining access to the inferior coracoid 22, which may require dissection of the muscle and fascia that must be subsequently repaired as part of the overall repair. These methods may be generally less invasive, and may potentially reduce internal scarring and healing time, external incision scars and procedure time. As another example, when placing an anchor within the tibia or fibula during an ankle syndesmosis repair, the option of placing a cannula or bullet distal edge on either the tibial or fibula may require removal of excessive material around the two bones, or excessive dissection around the tibia or fibula. System 500 advantageously relies on reference surface(s) other than the entrance or external surface of a target bone, to reliably place an anchor within the target bone. System 500 may advantageously limit diameters of passages or holes formed through bones of the joint or excessive dissection overall. System 500 also advantageously holds the two bones in the target repaired relationship while the repair construct is assembled to the two bones. System 500 also forms a passage and may place a flexible member from the anchor through the first bone, for later coupling to another anchor for joint repair.

Figure 5A:
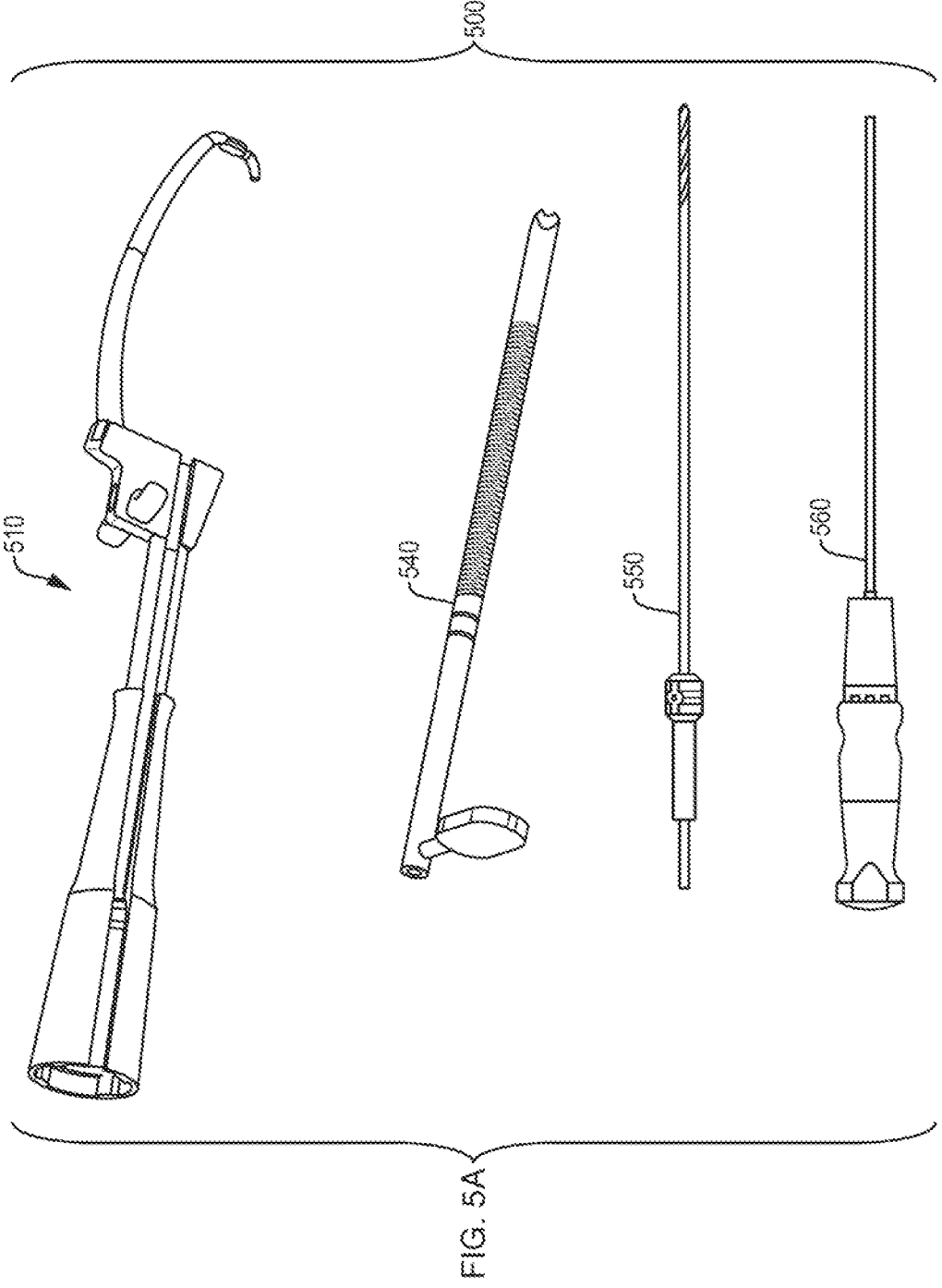
FIG. 5A illustrates a system for placing an anchor through a first bone and within a second bone during a joint repair, in accordance with this disclosure.

System 500 provides anatomy reduction as well as trajectory control, depth control and actuation assistance for placing an anchor through a first bone and within a second bone, with efficient (reduced) bone tissue removal. Components of system 500 are shown in FIG. 5A, and may include a director guide 510, a bullet 540, a drill 550 and an anchor insertor 560. This system 500 may be configured to accurately place an anchor within the coracoid 22, leaving an inferior portion of the coracoid 22 preferably intact, thereby removing a minimal amount of the coracoid 22.

Figures 5B, 5C:
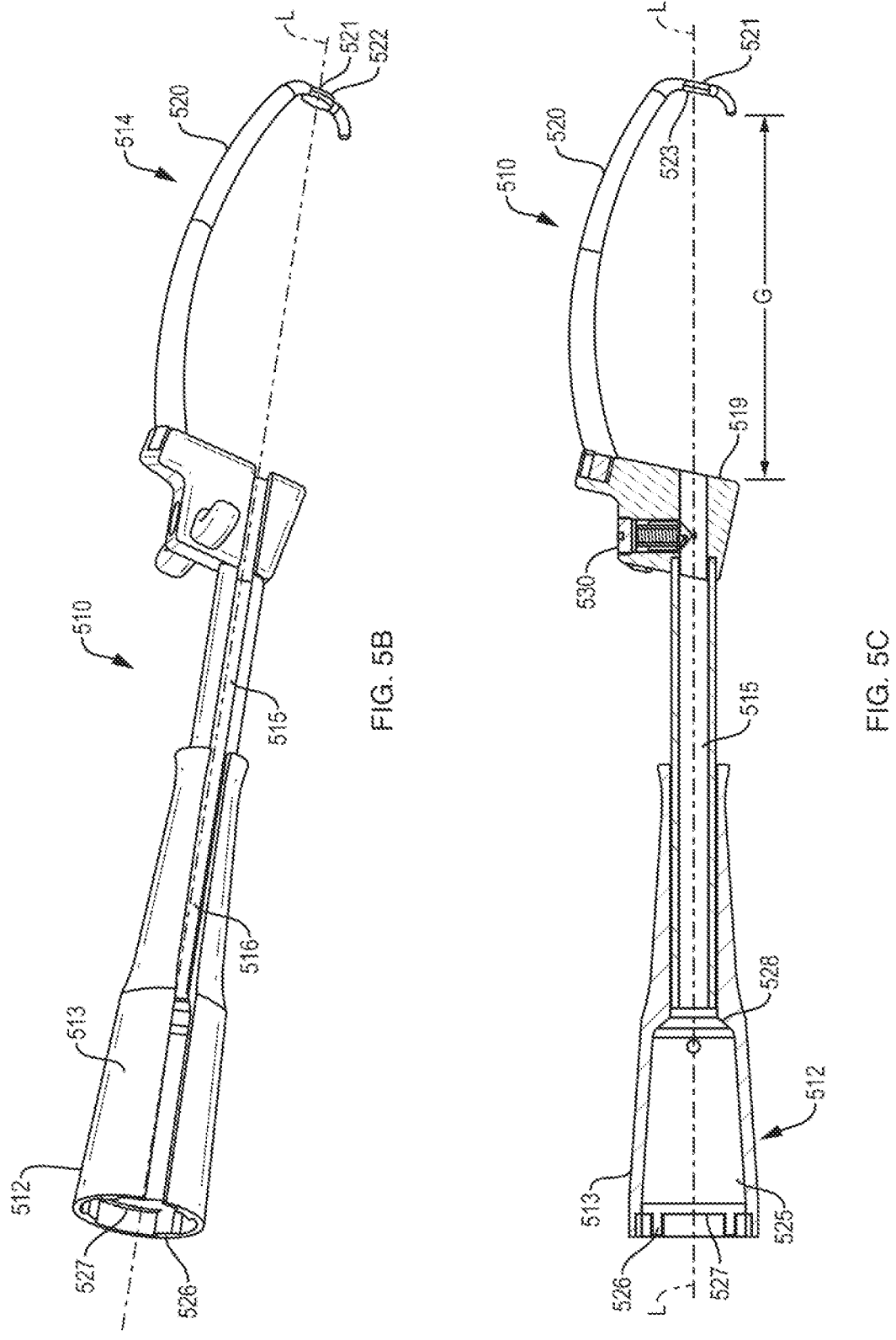
FIG. 5B is a perspective view of a guide of the system, in accordance with this disclosure.
FIG. 5C is a cross section view of the system guide, in accordance with this disclosure.
Figures 6, 7A, 7B:
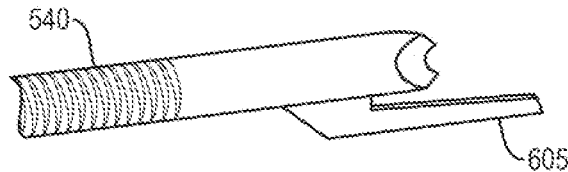
FIG. 6 illustrates an optional distal end of the bullet of the system shown in FIG. 5A, in accordance with this disclosure.
FIGS. 7A-7D illustrates a method of repairing an AC joint with system illustrated in FIG. 5A, including placing an anchor through a first bone and within a second bone, in accordance with this disclosure.

Turning now to FIGS. 58 and 5C, director guide 510 defines a proximal end 512 and distal end 514, distal end 514 including a director or aimer arm 520. Director guide 510 includes a cannulated shaft 515 to receive a bullet 540, drill 550 and anchor insertor 560 therethough. Cannulated shaft 515 may extend from proximal end 512. Cannulated shaft 515 may define an open lateral side 516. Director arm 520 is configured to encircle around an external surface of at least the two bones of the repair, to place an aimer tip 521 on a far side of the bones. This is shown in FIG. 7A. Director arm 520 is configured to encircle and span the anatomy that is being repaired/reduced. Distal tip 521 of director arm 520 preferably aligns with or intersects with a longitudinal axis L-L of cannulated shaft 515. In this example, aimer tip 521 includes a circular pad 522 with a center that is coincident with longitudinal axis L-L. Pad 522 defines reference surface 523. Pad 522 may be concave to engage and nest an inferior surface of the second bone. The distal tip 521 serves as an index feature that sets the axially limit of the drill 550 and anchor (310). In the example of an AC joint, the aimer tip 521 and more specifically the reference surface 523 may be placed on an inferior surface of the coracoid 22. In the example of an ankle syndesmosis repair, the reference surface 523 may be placed on a lateral surface of the fibula or the medial surface of the tibia. A tunnel through a portion of the coracoid 22 may be formed with the drill 550, the tunnel having a bottom surface at a predetermined distance, short of (axially spaced away from) the reference surface 523. This forms a cavity within the coracoid 22, having a bottom surface axially spaced superiorly from the coracoid inferior surface, saving valuable coracoid tissue.

FIG. 5C illustrates a cross-section of the guide 510. Proximal end 512 generally defines a handle 513 that includes a proximal cavity 525. Cavity 525 may be coaxial with longitudinal axis of guide 510 and may include slots and keys surfaces 526 that positively engage portions of inserter 560. Cavity 525 may be sized to receive a portion of an anchor inserter handle therein and these slots or keys 526 may limit the axial travel and/or rotational movement of the inserter 560 relative to the guide 510. Cavity 525 may also include a stop surface 528 that may engage a drill stop to control the axially extent or translation of drilling through the bones. This limits penetration of a drill 550 into the tissues. Cavity 525 therefore is also sized to receive a portion of the drill therein. Director arm 520 may define an axial gap "G" sized to preferably place tip surface 523 on or adjacent a first side of a second bone with guide surface 519 external to the patient, on or adjacent the patient skin.

Figures 5D, 5E:
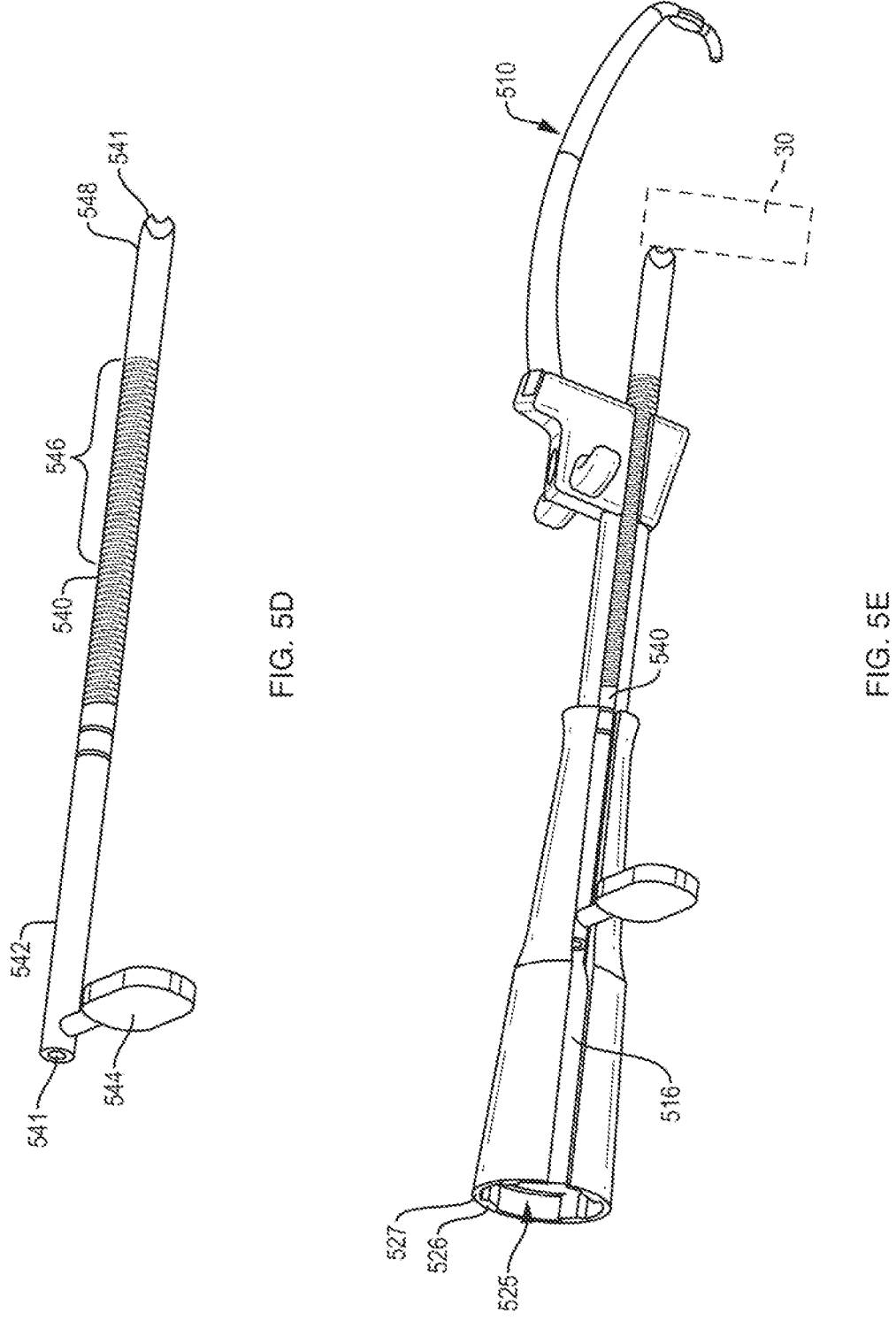
FIG. 5D is a perspective view of a bullet of the system, in accordance with this disclosure.
FIG. 5E is a perspective view of the bullet assembled to the system guide, in accordance with this disclosure.

Turning now to FIG. 5D, details of bullet 540 is shown. Bullet 540 defines an elongate cannulated shaft, the cannulation 541 extending through the bullet 540, providing passage of surgical tools therethrough. Bullet 540 is configured for insertion into and along guide cannulated shaft 515. Bullet 540 may define a proximal end 542 that may include a handle 544 for translating the bullet 540 along the cannulated shaft 515. Handle 544 may extend transverse a longitudinal axis of bullet shaft and may extend through open lateral side 516 to be disposed external to the guide 510. Bullet distal end 548 may define engaging means for gripping an external surface of a bone or tissue. The distal aspect of the bullet may impinge on the proximal aspect of the first bone tissue, such as the superior aspect of the clavicle 18. In other joints, the distal aspect of the bullet 540 may impinge on the medial aspect of the tibia or the lateral aspect of the fibula.

Bullet 540 may include a plurality of circumferential ridges or teeth 546, defining a rack feature for interacting with a sprung ratchet 530 of guide 510. This may fix a position of bullet end 548 on the bone surface and resist axial sliding of the bullet 430. Bullet end 548 may be translated to extend into and along gap "G" in use (FIG. 5E), to engage a surface of a first bone. An example first bone tissue 30 is shown as illustration. Bullet 540 is entirely distally disposed relative to cavity 525 when engaging the bone surface, which may preferably avoid inadvertent bullet interaction with the stop surfaces (526, 527, 528) within cavity 525.

Figures 5F, 5G, 5H:
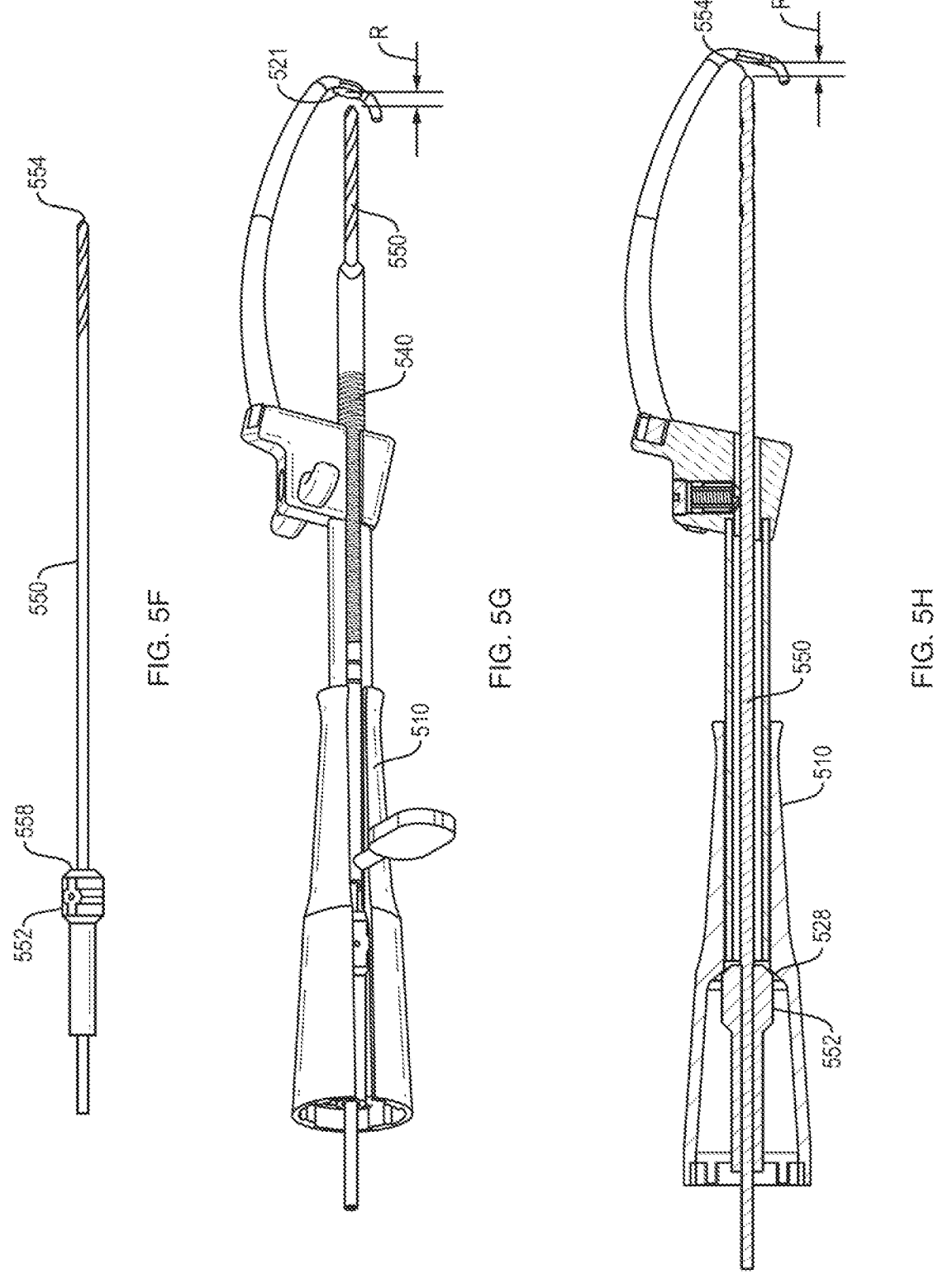
FIG. 5F is a view of a drill of the system, in accordance with this disclosure.
FIG. 5G is a view of the drill and the bullet assembled to the system guide, in accordance with this disclosure.
FIG. 5H is a cross section view of the drill and the bullet assembled to the system guide, in accordance with this disclosure.

With the bullet 540 in position, engaging a bone surface, a drill 550 may be introduced into the system 500 and inserted into and long the bullet cannulation 541. FIG. 5F illustrates drill 550 and FIG. 5G illustrates the drill 550 inserted into bullet 540 and guide 510. Drill 550 includes hub 552 configured to limit axial travel of drill tip 554. Drill proximal end is configured to operatively couple to a drive configured to actuate drill and form a passage through the bones, similar to drives known in the art. System 500 preferably aims drill tip 554 through a first bone and towards reference surface 523 of guide tip 521, while limiting axial travel such that drill tip 554 may stop before penetrating the entire thickness of the second bone. In this example, drill hub 552 includes a distal facing stop surface 558 configured to limit axially translation. Stop surface 558 may abut cavity surface 528 for example. An axial distance between the cavity stop surface 528 and reference surface 523 is preferably longer than a corresponding axial distance between a distal surface 558 of hub 552 and distal most edge of drill tip 554, defining bone saving length "R". FIG. 5H illustrates a cross section view of drill 550 relative to guide 510, showing hub 552 engaging surface 528, configured to stop drill tip 554 short by distance "R" from reference surface 523. Bullet 540 is removed from FIG. 5H for simplicity purposes only.

Figures 5I, 5J, 5K:
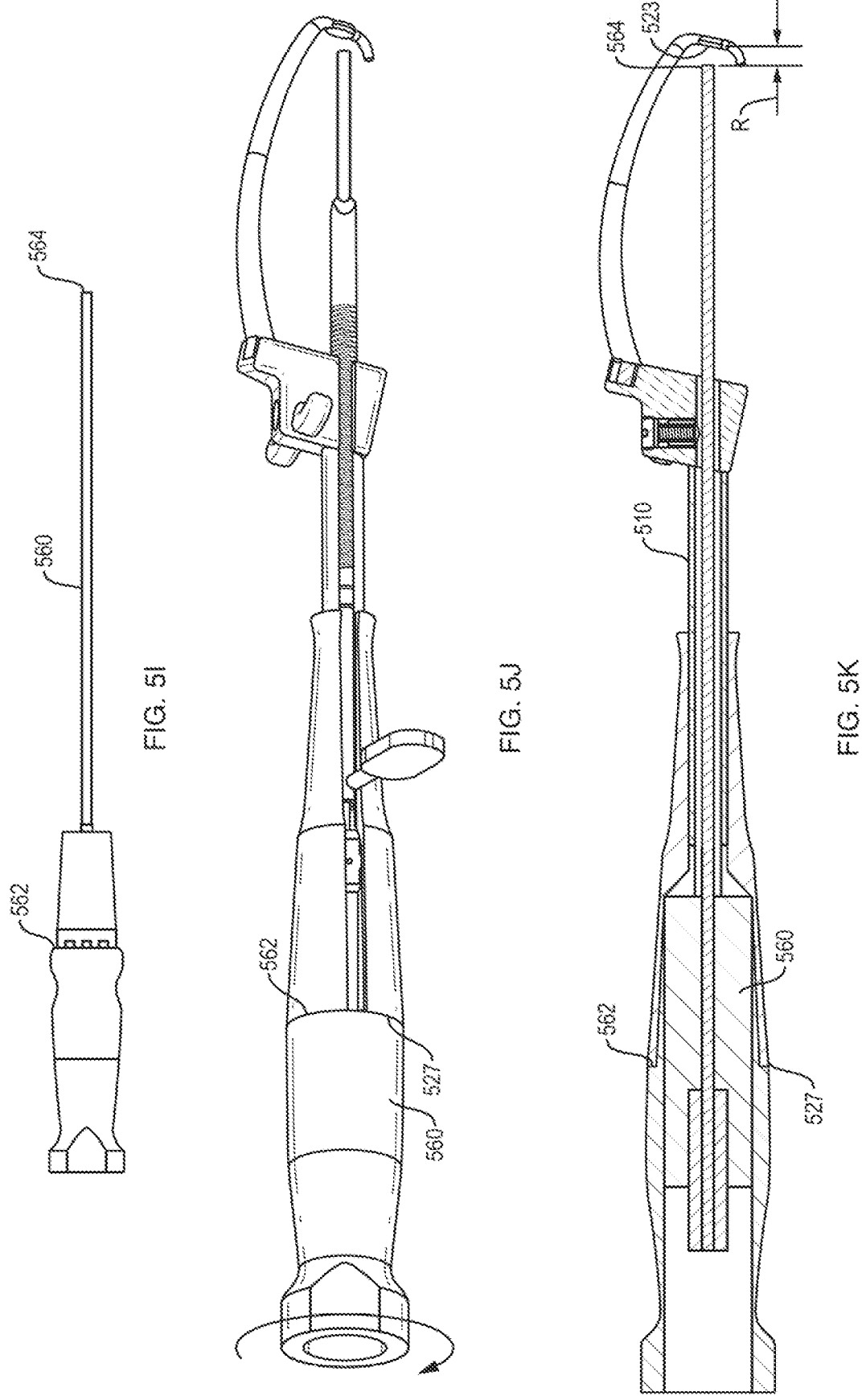
FIG. 5I is a view of an anchor inserter that may part of the system in FIG. 5A, in accordance with this disclosure.
FIG. 5J is an assembled view of the anchor inserter assembled to the bullet and system guide, in accordance with this disclosure.
FIG. 5K is a cross section view of the anchor inserter assembled to the bullet and system guide, in accordance with this disclosure.

Once the tunnel through the first bone and partially through the second bone is formed, the drill 550 may be removed, leaving the guide 510 and bullet 540 in place and engaging the anatomy. This aids in maintaining the two bones in an anatomically reconstructed relationship to each other. An anchor insertor 560 may then be inserted through the guide 510 and bullet 540, the bullet end 546 engaging an external surface of the first bone. The anchor inserter 560 may be inserted through the first bone and into the partial tunnel in the second bone. Example inserter 560 is shown in FIG. 5I, that may be assembled with a soft anchor such as anchor 310. Example inserter may be an all-suture anchor inserter, similar to the Q-fix system, offered for sale by Smith and Nephew. All-suture 310 may be a part of a repair construct including a flexible member, as disclosed later herein.

Guide handle cavity 525 may receive a portion of the inserter 560 therein and may include keys 526 or features that serve as a counter rotation feature that facilitates the actuation and deployment of the anchor 310. During deployment of anchor 310, activation may include rotating the inserter handle, these keys 526 inhibiting spinning of the insertor handle within guide 510. Insertor handle may also include an annular rim 562 that engages a circumferential proximal edge surface 527 and limits axial translation of the inserter 560. This limits axial translation of the anchor into the dead-end hole within the second bone. An axial distance between the annular rim 562 and a distal edge surface 564 of the inserter shaft plus the gap distance "R" may be equal to an axial distance between edge surface 527 and reference surface 523 (illustrated in FIG. 5K). The system 500 is configured to control the axial travel of the inserter 560, thereby defining the axial location of the inserted anchor with respect to the distal aspect of the second bone.

Other anchors may be inserted with this system 500, such as rigid anchors, or interference screws. The director guide 510 may include a plurality of cannulations or means of accepting multiple drills or multiple inserters at different locations and trajectories. The distal portion of the bullet 540 may contain a finger 605 to help position the bullet, relative to the clavicle 22, illustrated in FIG. 6. Finger 605 is configured to engage a posterior or anterior surface of the first bone (such as the clavicle) and preferably place the bullet distal edge in a targeted location relative to the posterior or anterior surface. Finger 605 may define an elongate body that extends further, distally, than bullet distal edge. Finger 605 is axially offset from the bullet longitudinal axis. This axial offset is configured to preferably place the bullet in a target location on the bone that is engages.

An example method of AC joint repair using system 500 to place an anchor of a repair construct is illustrated in FIG. 7A-7D. This method places an anchor within a second bone, accessing the second bone via a passage through a first bone of the joint. This system 500 and associated method may place an all-suture anchor 310 through the clavicle 18 and within the coracoid 22. Starting with FIG. 7A, guide 510 is first placed though a superior portal 50 onto an inferior surface of the coracoid 22. This places a reference surface 523 on the inferior surface of the coracoid 22 inferior to and axially aligned with a target insertion location for an anchor within the coracoid 22. The reference surface 523 ensures proper targeting of a drill tunnel through the bones. Guide handle 513 may remain external to the patient and may be superior to clavicle 18. System 500 may include a bullet 540 that may be cannulated. Bullet 540 may be inserted into a cannulated shaft 515 to engage superior surface 19 of clavicle 18 to stabilize clavicle 18. Bullet end 519 engages superior surface 19. Guide 510 may reduce the two bones and hold the two bones in a target relationship relative to each other which may be an anatomical repaired relationship. Bullet 540 is cannulated 541 to receive a drill 550 and anchor inserter 560 sequentially therethrough. Drill 550 may extend through the cannulated bullet 540, through the entire clavicle 18 and only partially through the coracoid 22. Drill 550 may be inserted through bullet cannulation 541 up until a stop surface 558 abuts a surface 528 within cavity of guide handle 513. Stop surface 558 may be a distal facing circumferential surface. This places the drill through the first bone (clavicle 18) and part way through the second bone (coracoid 22). The surfaces (558, 528) stop the drill tip 554 at a location within the second bone a distance R from reference surface 523, thus minimizing removal of bone tissue from the second bone. The surfaces (558, 528) stop the drill tip 554 at a location within the second bone sufficiently deep within the second bone to provide sufficient anchoring length with an anchor embedded therein.

Figures 7C, 7D:
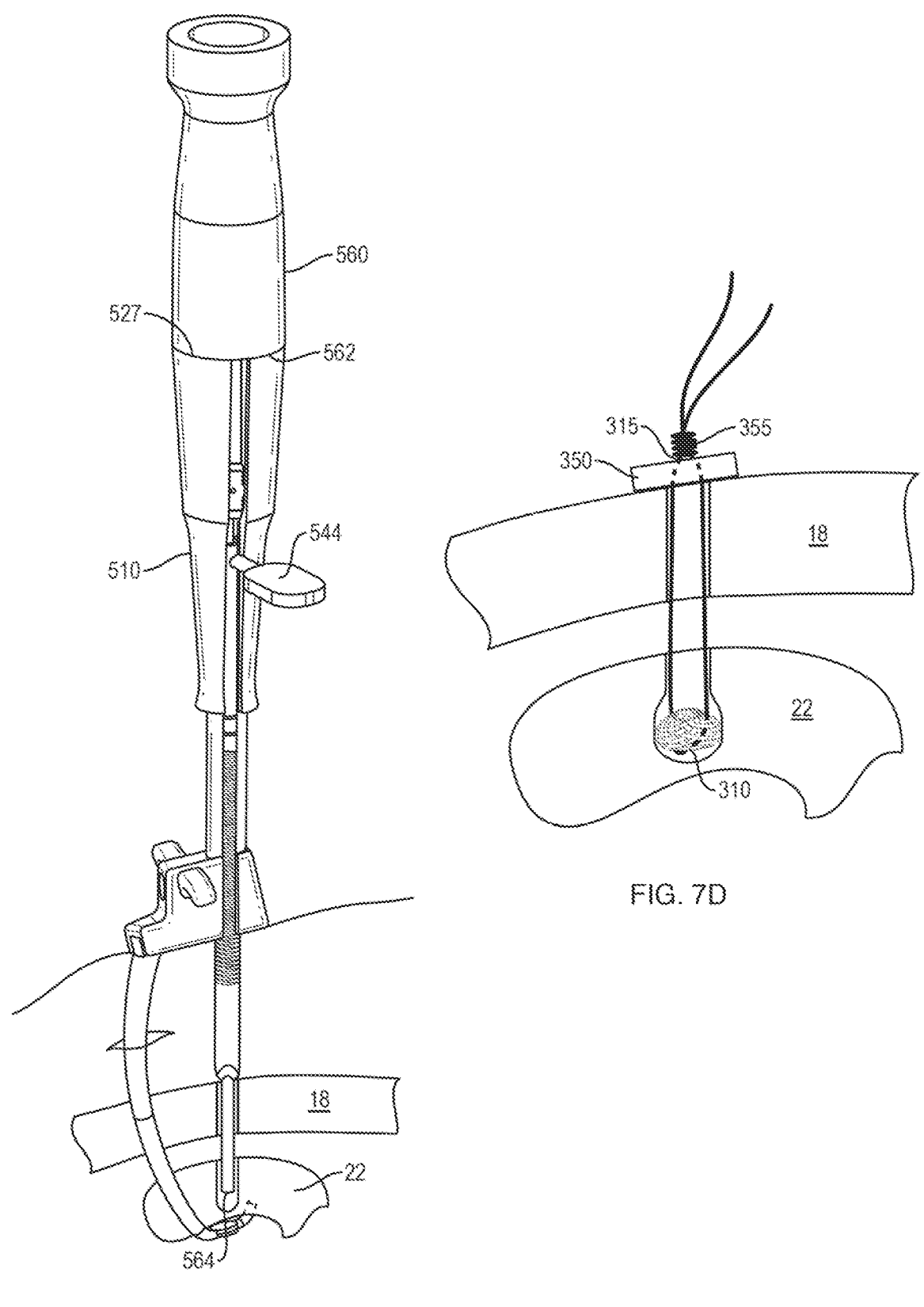

Once a tunnel has been formed through clavicle 18 and partially into the coracoid 22, drill 550 may be removed, and an anchor inserter (560) inserted through the handle cavity 525 and bullet cannulation 541. This may place the anchor, which may be an all-suture anchor 310, as shown in FIGS. 7C and 7D. The inferior portion of coracoid 22 may preferably still be intact. Inserter 560 may be inserted up until an annular rim 562 of the inserter 560 engages a circumferential proximal edge 527 of the guide handle 513. Slots/keys 526 of guide handle 513 may engage mating keys on the inserter 560 to counter any rotation of the inserter 560. Controlled active deployment of the all-suture anchor 310, may require rotation of an inserter actuator, and keys 526 may prevent rotation of inserter within guide 510 during anchor deployment. Deployment may include rotating actuator to place tension on a flexible member 315 operatively coupled to anchor 310. After deployment, inserter 560 may be removed leaving the flexible member 315 extending from deployed anchor 310' and through both bones.

FIG. 7D illustrates anchor 310 embedded within coracoid 22, with suture 315 operably coupled to a second anchor 350. Anchor 350 may be a button style anchor and may engage a superior surface 19 of clavicle 18. A knot 355 may be tied to lock the two bones (18, 22) in place. More than one suture 315 may be employed, or alternative flexible member such as tape or wire may extend through the anchor 310. A kit to repair an AC joint may include a system 500 and a second anchor 350 configured to engage the superior surface 19 of the clavicle 18. This guide may alternatively place rigid anchor with the coracoid.

FIGS. 8A-8D illustrate another embodiment of a system 800 that may be used to insert an anchor through a first bone and into a second bone. Similar to system 500, system 800 may provide trajectory control and actuation assistance for an anchor-based repair construct, that may reduce and hold two bones relative to one another. The anchor may be rigid or a soft anchor, such as all-suture anchor 310. In this example embodiment, the system 800 may include a guide 810 and bullet 840 for use with a drill and anchor inserter, such as drill 550 and inserter 560. Like components have been given the same reference numerals. Similar to the previously disclosed embodiment, bullet 840 may include a ratchet rack feature 846 that engages with the pawl 812 contained in the guide 810. In this embodiment, bullet 840 includes a handle 845 that functions similarly to guide handle 513. For example, handle 845 may sequentially receive and interface with both the drill 550 and the inserter 560, to limit their trajectory and axial translation.

Figures 8A, 8B:
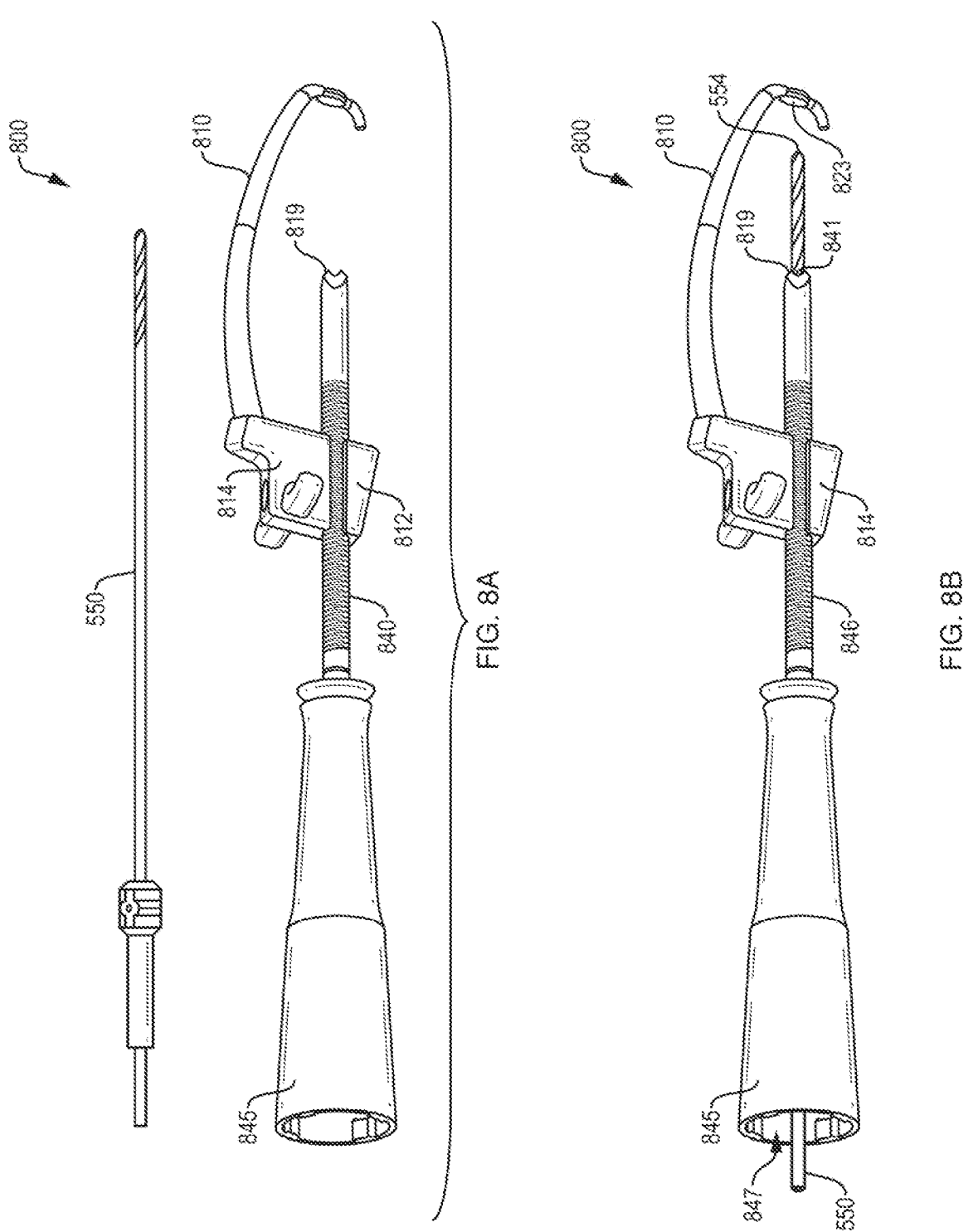
FIG. 8A illustrates another system for placing an anchor through a first bone and within a second bone during a joint repair, in accordance with this disclosure.
FIG. 8B illustrates a drill and bullet assembled to the system guide, in accordance with this disclosure.
Figures 8C, 8D, 8E:
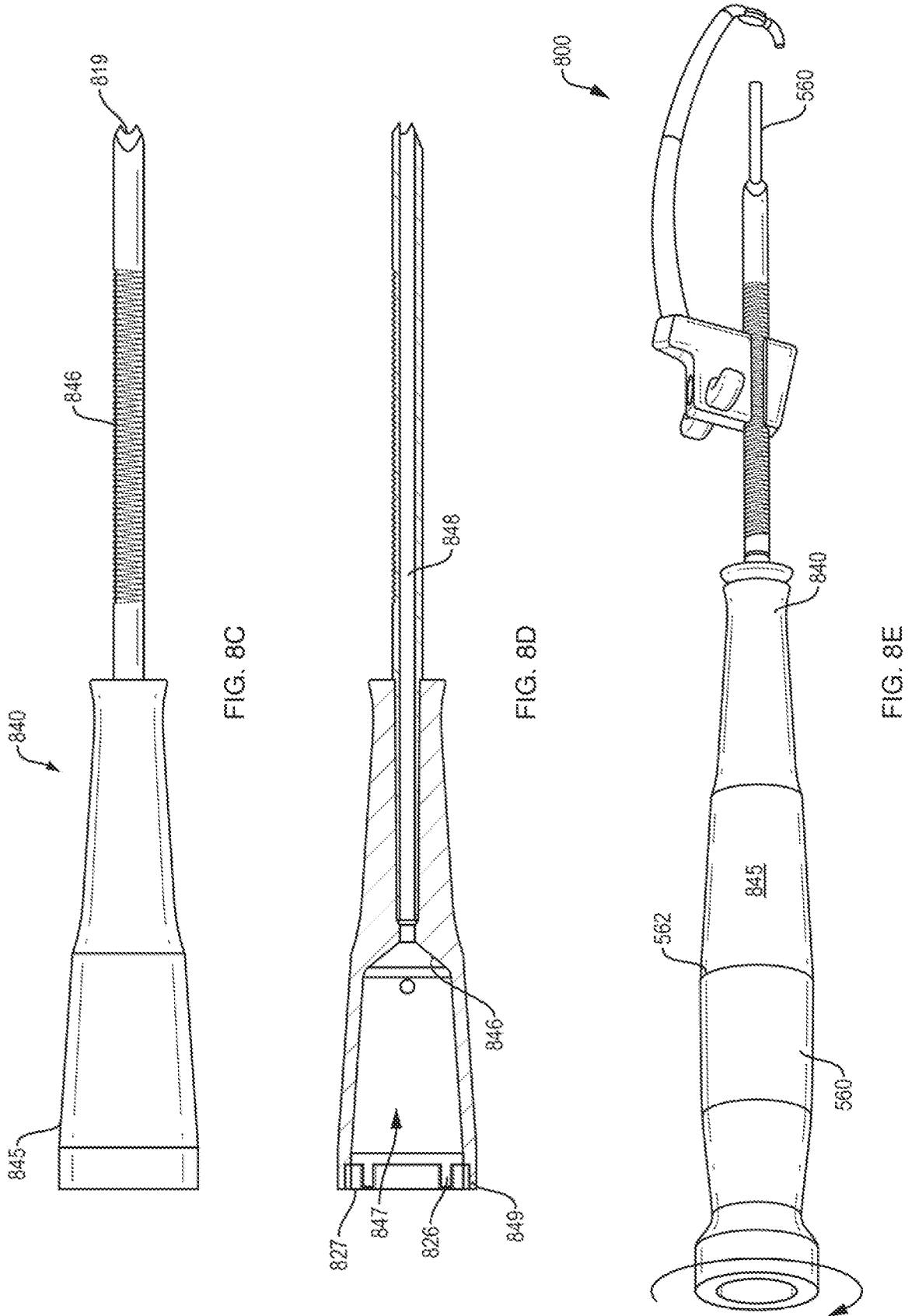
FIG. 8C illustrates a bullet of the system, in accordance with this disclosure.
FIG. 8D illustrates a cross section of the bullet, in accordance with this disclosure.
FIG. 8E illustrates an assembled view of the anchor inserter assembled to the bullet and system guide, in accordance with this disclosure.
Figure 14A:
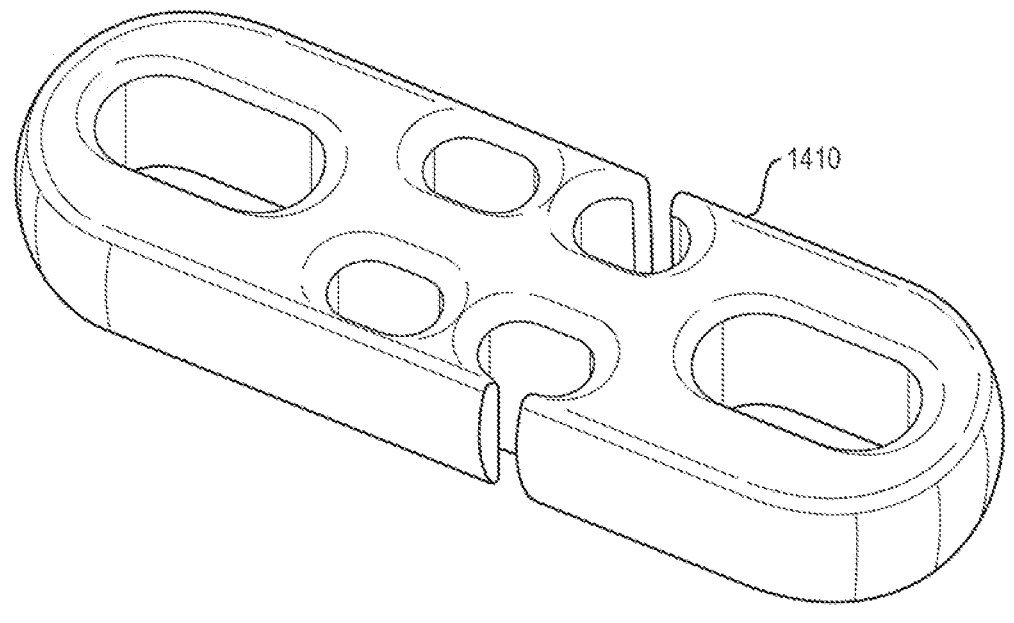
FIGS. 14A-14B illustrate example cortical button embodiments, in accordance with this disclosure.
Figure 14B:
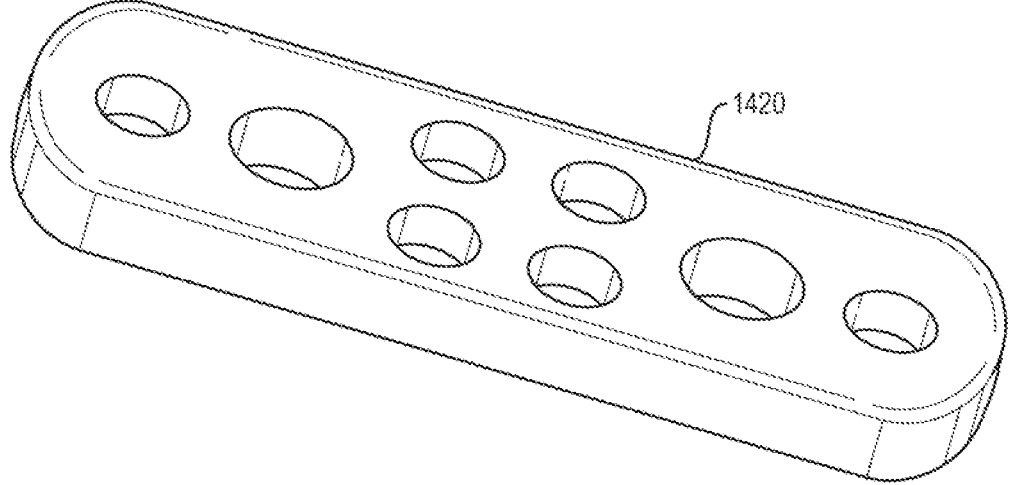
Figure 16A:
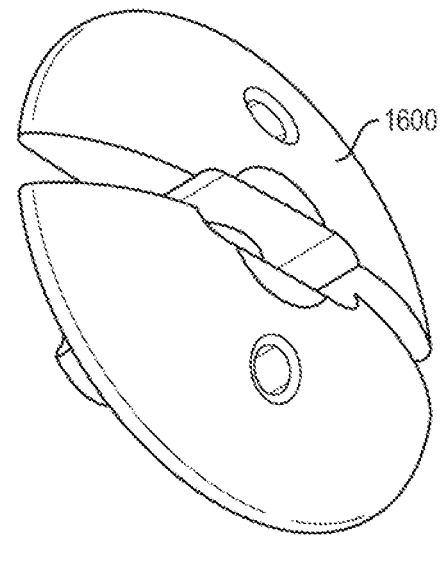
FIGS. 16A-16D illustrates various views of another cortical button embodiment, in accordance with this disclosure.
Figure 16B:
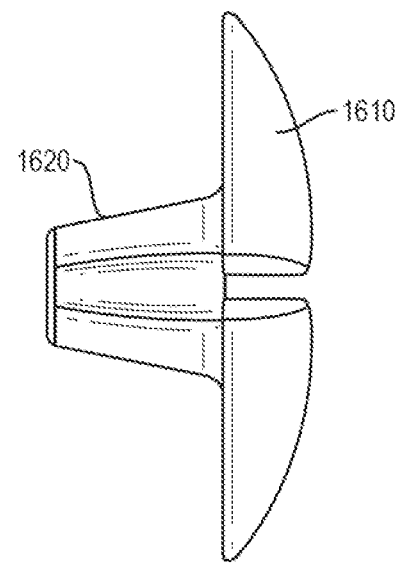
Figure 16C:
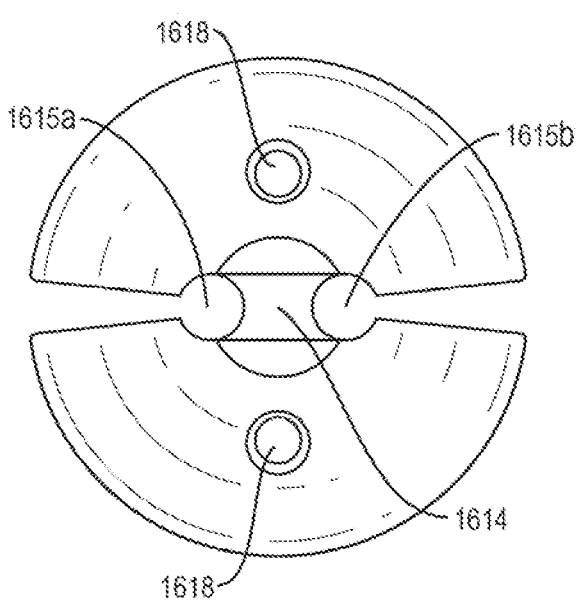
Figure 16D:
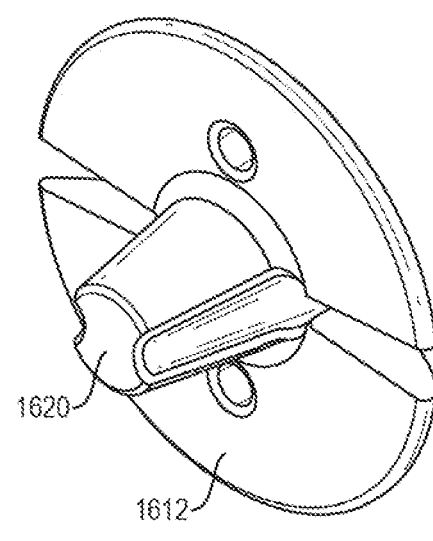

FIG. 8B illustrates the system 800 with the drill 550 inserted into and along a handle cavity 847 and cannulation 848 of bullet 840. Seen best in FIGS. 8B and 8D, bullet handle 845 defines a proximal cavity 847 for receiving the drill 550 and inserter 560 therein. Cavity 847 is continuous with a bullet cannulation 848. Cavity 847 includes a stop surface 846 and an inserter interface portion 849. Stop surface 846 is configured to limit axial translation of drill 550 into the second bone. Drill 550 may then be removed from system and an inserter 560 placed through bullet cannulation 848 and in engagement with inserter interface 849. Inserter interface 849 may both help to hold the inserter 560 and apply a counter torque to the inserter, similar to system 500. Inserter interface 849 may include keys/slots 826 example. During deployment of anchor, activation may include rotating the insertor handle, these keys 826 inhibiting spinning of the insertor handle. FIG. 8E illustrates inserter 560 inserted through bullet cannulation 848. Insertor handle may also include an annular rim 562 that engages a circumferential proximal edge surface 827 of bullet handle 845 and limits axial translation of the inserter 560. This limits axial translation of the anchor into the dead-end hole within the second bone. The system 800 is configured to control the axial travel of the inserter 560, thereby defining the axial location of the inserted anchor with respect to the distal aspect of the second tissue, which may be the inferior aspect of the coracoid.

An example method of using system 800 to place an anchor may include placing guide 810 though a superior portal and a tip of the guide arm onto an inferior surface of the coracoid 22. This places a reference surface 823 on the inferior surface of the coracoid 22 inferior to a target insertion location for an anchor within the coracoid 22. The reference surface 823 ensures proper targeting of a drilled tunnel through the bones. Guide housing 814 and bullet handle 845 may remain external to the patient and may be superior to clavicle 18. Bullet 840 may be slid along housing 814 to engage superior surface of clavicle 18 to stabilize clavicle 18. Bullet end 819 engages superior surface 19. Guide 810 and bullet 840 may reduce the two bones and hold the two bones in a target relationship relative to each other which may be an anatomical repaired relationship. Bullet 840 is cannulated 841 to receive a drill 550 and anchor inserter 560 sequentially therethrough. Bullet 840 may be configured to limit a drill depth, such that the drill 550 may extend through the cannulated bullet 840, through the entire clavicle 18 and only partially through the coracoid 22. Bullet 840 may have a length "L" with a stop that cooperates with the drill 550 and anchor insertion instrument 560 to limit drill depth and all-suture anchor insertion depth.

Bullet handle 845 may include a cavity 847 with stop surface 846 that limits axial translation of the drill tip 554. Drill 550 may be inserted through bullet cannulation 841 up until a stop surface 552 abuts a surface 846. This places the drill through the first bone and part way through the second bone. The surfaces (552, 528) stop the drill tip 554 at a location within the second bone a distance "R" from reference surface 823, thus minimizing removal of bone tissue from the second bone.

Once a tunnel has been formed through clavicle 18 and partially into the coracoid 22, drill 550 may be removed, and an anchor inserter inserted through the bullet handle cavity 845 and bullet cannulation 841. This may place the anchor, which may be an all-suture anchor 310, as shown in 7D. The inferior portion of coracoid 22 may preferably still be intact. Inserter 560 may be inserted up until an annular rim 562 of the inserter 560 engages a circumferential proximal edge 827 of the bullet handle 845. Slots/keys 826 of bullet handle 845 may engage mating keys on the inserter 560 to counter any rotation of the inserter 560. Controlled active deployment of the all-suture anchor 310, may require rotation of an actuator, and keys 526 may prevent rotation of inserter during anchor deployment.

The method may then continue by operatively coupling suture 315 to a second anchor 350 (reference FIG. 7D). Anchor 350 may be a button style anchor. A knot 355 may be tied to lock the two bones (18, 22) in place. More than one suture or alternative flexible member such as tape or wire may extend through the anchor 310. Anchor 310 may be a rigid anchor. A kit to repair an AC joint may therefore include a system 800 and a second anchor 350 configured to engage the superior surface 19 of the clavicle 18.

An example method of repairing a disrupted AC joint is disclosed including first forming a passage through the clavicle 18 and then a partial passage through the coracoid 22, leaving an inferior portion of the coracoid 22 continuous. An anchor (310) is inserted through the clavicle passage and then into the partial passage and deployed so as to anchor the anchor within the coracoid partial passage. A flexible member may be provided coupled to the anchor. Inserting may place the flexible member along both passages. The anchor may be an all-suture anchor and deploying may include applying tension to the flexible member. A second anchor may be coupled to the flexible member adjacent the clavicle to complete the repair.

The passages may be formed with a guide (510, 810) that together with a corresponding bullet (540, 840) engages and clamps the clavicle and coracoid in anatomically correct positions. Guide (510, 810) includes an arm that extends around the coracoid 22 and clavicle 18 and is configured to engage an inferior surface of the coracoid 22, defining a reference surface (523, 823). Guide (510, 810) and corresponding bullet (540, 840) guide a trajectory and limit an axial extent of a drill to form the passage through the clavicle 18 and the partial passage through the coracoid 22. Guide (510, 810) and/or bullet (540, 840) includes a surface that limits axial motion of drill 550 to stop drill short of reference surface (523, 823) and thereby avoid interruption of coracoid inferior surface. Guide (510, 810) and/or bullet (540, 840) includes a surface that abuts a hub surface of the drill 550 to limit axial motion of the drill 550. The two passages are axially aligned. A guide wire (not shown) may first be used before using a sleeved drill to over-drill the guide wire and form the two passages. In this case both the guide wire and drill 550 may include a means of limiting axial motion through an inferior surface of the coracoid. The drill 550 (and guide wire) may then be removed.

An inserter such as inserter 560 may be inserted along the prepared passages. Inserter 560 may insert an anchor coupled to a flexible member within the partial passage. Inserter 560 may insert an all-suture anchor for example such as anchor 310. Inserter 560 may interact with the guide (510, 810) and bullet (540, 840) to place the anchor through the clavicle passage within the partial passage of the coracoid 22, sufficiently within the coracoid for strong anchoring. Anchors such as all-suture anchors preferably anchor underneath the cortical layer and embed into the softer cancellous bone tissue. Inserter 560 may interact with the guide (510, 810) and bullet (540, 840) to place the anchor inferior to the superior cortical layer of the coracoid 22, but also superior to the inferior cortical layer. The partial passage, formed by the drill 550 therefore forms a passage length that does not interrupt the inferior coracoid bone surface, but sufficiently long to receive the un-deployed anchor and place the all-suture anchor 310 under the superior cortical layer of the coracoid. For example, for a coracoid thickness of 13 mm, a partial passage may be formed that preferably extends no longer than 10 mm into the coracoid 22, as measured from the superior surface of the coracoid 22. An anchor that is preferably less than 8 mm in length may be inserted and still be positioned under the superior cortical layer. If anchor is an all-suture anchor the deployed length shortens to about 4 mm. A stop surface of the drill 550, guide (510, 810) or bullet (540, 840) may be moveable to alter the depth of the coracoid passage, based on information from pre-surgical imaging, or based on the anchor choice and their associated dimensions. For example, for a thinner smaller coracoid, the surgeon may wish to use smaller anchor and drill a shorter passage into the coracoid.

Deploying the anchor may include rotating an actuator of the inserter 560, and guide (510, 810) and/or bullet (540, 840) may include counter rotation means to stabilize the inserter 560 during deployment. After deployment, the inserter 560 may be removed leaving the anchor in place and at least one flexible or linking construct (315) extending through the two passages. The guide (510, 810) and/or bullet (540, 840) may also be removed, and a second anchor may then be coupled to the flexible member 315. The joint may need to be manually reduced through application of external pressure on the patient's shoulder to reduce the distance between the patient's coracoid and clavicle to re-approximate or maintain the bones, tendons, and ligaments back in their anatomical locations. Tension on the flexible member may reduce the distance between the two anchors and thereby the two bones, such that the distance between the two anchors conforms to the reduction in the joint, with the first anchor 310 within the coracoid and the second anchor engaging the superior surface of the clavicle. After the two bones are reduced to the preferred distance, a surgical knot may be tied along the flexible member to lock the two anchors at the target distance.

In some alternative methods, a guide may be avoided. Shown in FIGS. 9A and 9B, the anchoring implant such as anchor 310 may be inserted freehand. This may avoid having to resect soft tissue to gain access to the inferior side of the coracoid 22 with the guide arm. A curved drill guide 410 may be placed on a superior surface 19 of clavicle 18. A removable obturator 420 may be used to gain access to the clavicle 18. A drill may then form a tunnel through the clavicle 18 and partially through the coracoid 18 similar to the previously method disclosed in FIG. 7A-7C. An anchor 310 may be inserted and deployed through the drill guide 410.

A method of fixation may include placing two anchors 310*a* and 310*b*, illustrated in FIG. 10. Two links between the coracoid 22 and clavicle 18 may better simulate or mimic the stiffness vectors of the original trapezoidal and conoid ligaments (CC ligaments). Multiple links between the two bones may improve surgical outcomes. A first anchor 310*a* may be placed to link the coracoid 22 to the clavicle 18 at a location approximately adjacent the trapezoid ligament 14 and a second anchor 310*b* may be placed to link the coracoid 22 to the clavicle 18 at a location approximately adjacent the conoid ligament 16. System 500 or system 800 may be used, sequentially to place anchors 310*a*, 310*b*. Anchors 310*a*, 310*b* may be inserted and deployed as described herein, and both ends of deploying/repair sutures 315*a* and 315*b* may be coupled, for example with a knot 1010 to form a bone bridge over the clavicle 18.

Two tunnels may be formed using a double guide 1100 shown in FIG. 11A and FIG. 11B. Superior portion of guide 1100 may include a surface 1105 contoured to match the clavicle superior external surface and may include two cannulations 1110*a* and 1110*b* configured to direct tunnel formation through the clavicle 18. Surface 1105 may be contoured to place the cannulations 1110*a*, 1110*b* in a targeted position on the clavicle 18. For example, a first cannulation 1110*a* may be configured to receive a drill therethrough to form a tunnel through at least the portion of the clavicle 18 that aligns with the orientation of the trapezoid ligament 14 or extends through the insertion zone of the trapezoid ligament 14 through the clavicle 18. A second cannulation 1110*b* may be configured to receive a drill therethrough for form a tunnel through at least a portion of the clavicle 18 that aligns with the orientation of the conoid ligament 16 or extends through the insertion zone of the conoid ligament 16 in the clavicle 18 and coracoid 22. The first and second cannulations 1110*a* and 1110*b* may be non-parallel to each other. The first cannulation 1110*a* may be angled such that the tunnel may be about 45 angular degrees medial to the sagittal plane and 45 angular degrees inferior to the transverse plane. The second cannulation 1110*b* may be perpendicular to the superior surface of the clavicle directly engaged by the boundary of the cannulation 1110*b* tunnel. This guide 1100 may be part of a kit that may include at least two anchors 310*a* and 310*b*. Guide 1100 may include an aimer tip 1120 that may engage the inferior portion of the coracoid 22, similar to guide 510 disclosed herein. The tunnels formed through the clavicle 18 may converge at a designated target area, such as in-between the coracoid 22 and clavicle 18, or inferior to the coracoid 22. There may be more than two cannulations through the guide.

Another example of a repair construct is shown in FIG. 13. FIG. 13 illustrates an adjustable knotlessly-locking repair construct 1300 wherein the coupling member between the two anchors forms a loop that is adjustable and includes locking passage as defined herein. FIG. 13 illustrates an adjustable construct 1300 including a first and second anchor 1310 and 1315, that may both be cortical buttons. Adjustable construct 1300 also includes at least one flexible coupling member 1320 that may operatively couple to the cortical buttons 1310 and 1315, via apertures or slots (shown later). Flexible member 1320 may define at least two discrete suture-locking passages 1322*a*, 1322*b* that may extend between the two buttons 1310, 1315. The two discrete suture locking passages 1322*a*, 1322*b* define two individual dilated suture regions, along separated portions of the flexible member 1320, each suture-locking passage receiving a single length or strand of flexible member 1320 therethrough. Flexible member 1320 may be a length of braided suture, having a hollow core. Portions of this braided suture may be dilated to receive a length of suture therethrough. Tension on this braided suture may cinch the dilated portion (suture-locking passage) around the length of suture threaded therethrough under tension similar to suture locking passages 118.

Flexible member may form a single loop 1320*a* that couples to both buttons 1310, 1315, with suture-locking passages 1322*a*, 1322*b* therebetween. Flexible member 1320 may loop over, around or through buttons 1310, 1315. Button 1310 may be configured to engage a superior surface of the clavicle 18. The suture locking passages 1322*a*, 1322*b* are spaced a fixed distance from each other along the flexible member 1320, defining saddle portion 1320*a*. Saddle portion 1320*a* defines a non-adjustable length and is preferably a short length, ensuring the two locking passages 1322*a*, 1322*b* lie predominately along the passage within the clavicle 18. Saddle portion 1320*a* is sufficiently long to operatively couple to the button 1310. Saddle portion 1320*a* may preferable be less than 10 mm and may be 5 mm in length. Suture-locking passages 1322*a*, 1322*b* may each be approximately 10 mm in length, sufficiently long to provide adequate locking strength. Withdrawing reduction limbs 1324*a*, 1324*b* together or separately may reduce the loop portion 3120*b* and draw button 1315 towards button 1310, as the construct 1300 is reduced. This construct 1300 may span the gap between the coracoid 22 and the clavicle 18 to reduce and provide fixation at the desired spacing. In some embodiments, suture locking passages 1322*a*, 1322*b* may wrap around the bones such as the clavicle 18 and or coracoid 22, avoiding tunnels through at least one of these bones.

Construct 1300 may include cortical buttons (1310, 1315), of varying shapes, having a varying number and size of slots or apertures, some examples of which are illustrated in at least FIGS. 14A-B, 15A-15D and 16A-16D. Buttons (1310, 1315) may be contoured to match the targeted outer bone surface. Options include passing and non-passing buttons, passing buttons configured to fit through a bone tunnel, such as example buttons 1410. Non-passing buttons may be more circular, examples of which are shown in at least FIG. 16A-16D. Repair constructs such as construct 1200, 1300 may be provided with at least one button pre-assembled to the flexible member 1230, 1320, similar to button 1420, illustrated in FIG. 14B. Repair constructs 1200, 1300 may be provided with at least one button partially assembled, or separated from the remains of construct 1200, 1300 and may include slots or open pathways, similar to button 1600, to optionally allow for later attachment by the end user during the procedure. Each limb of the flexible member (1230, 1320) may extend through its own opening through the corresponding button, requiring more openings therethrough, similar to buttons 1410 and 1420. In other embodiments, buttons may have less openings and multiple flexible member limbs share each opening. Further details of buttons that provided partially assembled or separate from the construct can be found in at least commonly owned PCT patent application US2020/038401, herein incorporated by reference in its entirety.

FIGS. 15A-15D illustrates various views of another example cortical button anchor 1500 that may be provided coupled to a flexible member of a repair construct such as, but not limited to construct 1200 or 1300. Anchor 1500 may be generally oblong in shape, having a length greater than a width. Anchor 1500 may define a first side surface 1510 that is curved. First side surface 1510 may define a semi-circular curved surface 1510, configured to mate with a cannula or circular bore of a shaft as shown in FIGS. 15B and 15D. Anchor 1500 may be symmetrical along its length and width, and at both ends 1505a, 1505b may be approximately semi-circular in cross section. First side surface 1510 may define an outer surface that faces away from the bone that the anchor 1500 engages with. Anchor 1500 opposing side surface 1520 may be concave. Side surface 1520 may define a curved surface, configured to mate with the target bone surface. For example, surface 1520 may define a curve that mates with the outer curvature of a coracoid inferior surface. Curved surface 1520 may define a thinner central portion of button 1500, with thicker portions at ends 1505a, 1505b, the thickness extending from surface 1510 to surface 1520. Button 1500 may include at least two through holes 1540a, 1540b extending from surface 1510 to surface 1520. Holes 1540a, 1504b may be coincident with a longitudinal axis L-L of button 1500. Holes 1540a, 1504b may be oblong in shape and sized to receive at least one length of a flexible member of a repair construct therethrough. In some embodiments, similar to construct 1300, holes 1540a, 1504b are sized to slideable receive at least two lengths of a flexible member 1320 therethrough. An example boundary B of a target bone tunnel opening is illustrated in FIG. 15C and holes 1540a, 1504b are configured to lie within boundary B. Stated another way, holes 1540a, 1504b are spaced apart and sized to define a maximum dimension L1, that may be equal to or smaller than the target bone tunnel opening size. This may help maintain flexible members aligned with bone tunnel and inhibit pinching or interference between flexible members, anchor 1500 and target bone.

Figures 36A, 36B:
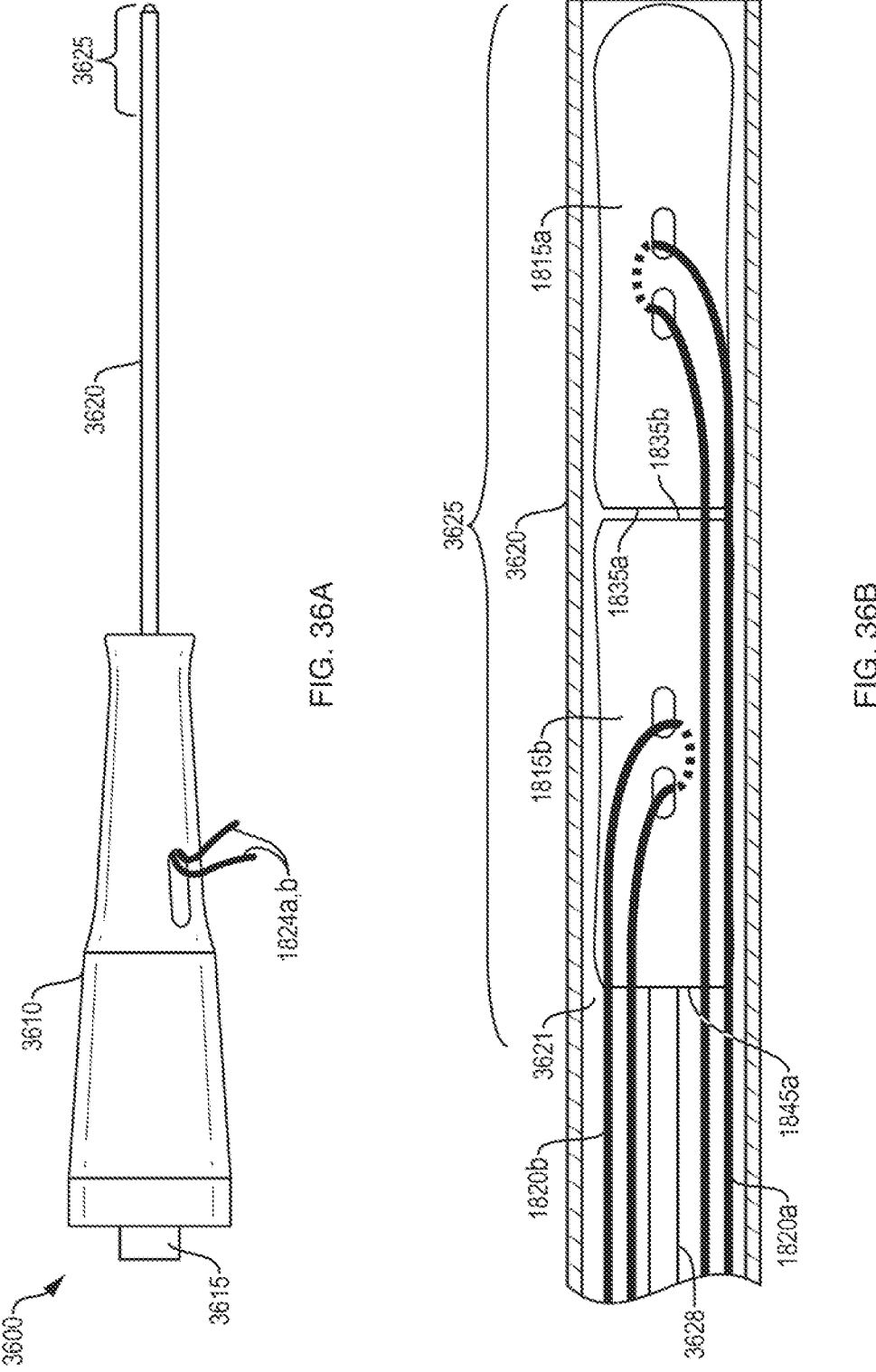
FIG. 36A illustrates a perspective view of an insertion instrument for placing at least one anchor at a passage exit of a bone, in accordance with this disclosure.
FIG. 36B illustrates a view of a distal end of the insertion instrument, with a portion of the distal end shaft removed to illustrate the anchors disposed therein, in accordance with this disclosure.
Figure 36C:
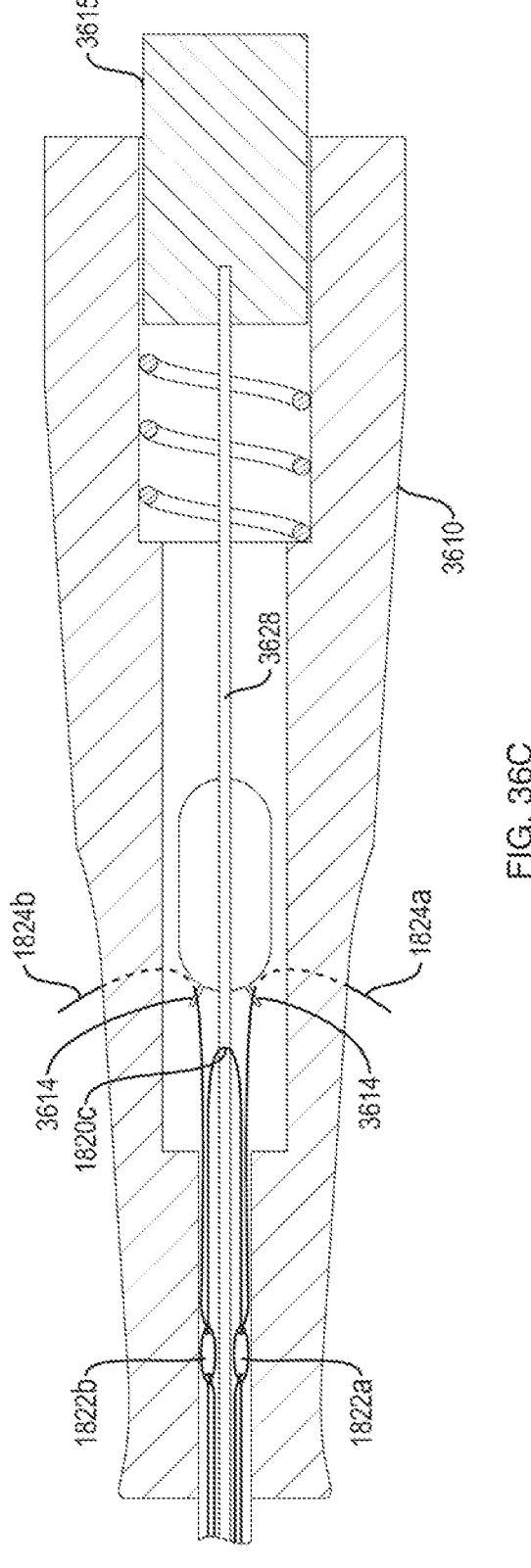
FIG. 36C illustrates a cross section of a handle end of the insertion instrument, in accordance with this disclosure.

Shown best in both FIGS. 15B and 15D, anchor 1500 may be provided within a shaft 1550 of an insertion instrument, similar to insertion instruments disclosed in FIGS. 36A-36C. Shaft 1550 may define a cannulation or bore 1551, and outer surface 1510 may be shaped to mate or match circumference of bore 1551. Anchor 1550 may be approximately semi-circular in cross section, thus filling about half of the bore 1551, leaving the remaining space (approximately half the bore) for housing the flexible members such as flexible members 1320. In some repair constructs, such as construct 1300, at least four limbs of flexible member 1320 may extend from anchor. End 1505b may also include a flat surface portion 1506, configured to interact with a push rod 1555, for advancing the anchor 1500 from insertion instrument. Some embodiments may include four through-holes to separately manage each length or strand of flexible member.

FIG. 16A-16D illustrates various views of another example cortical button 1600 that may be provided separated from repair construct, such as but not limited to construct 1200 or 1300 and assembled during the procedure. Button 1600 may have a circular outer profile. Button 1600 is defined as a "non-passing" button and therefore does not pass through a bone tunnel, as the outer diameter of the circular outer profile is generally too large for a reasonable tunnel size. However, the circular engagement with the bone provides similar structural properties to an elongate button with a lower profile (thickness) of button 1600. This means that anchor 1600 stands less proud of the target bone than an equivalent strength elongate/oblong button. Button 1600 may therefore be less palpable than an elongate button. Button 1600 is therefore preferable for locations easy to access and near a palpable surface. Button 1600 may be used as part of construct 1200, 1300 for example to engage the superior surface of the clavicle 18. Button 1600 may be similar to some embodiments disclosed in PCT patent application number PCT/US20/059175 filed Nov. 5, 2020; and PCT/US20/038401 filed Jun. 18, 2020, both commonly owned and herein incorporated by reference in its entirety.

Button 1600 defines a dome portion 1610 with a tapering outer periphery. Button 1600 may have improved stress distribution around the button, which allows it to be thinner relative to oblong buttons. Button 1600 also include a post 1620 concentric with the dome portion 1610 and extending from a lower surface 1612 of dome portion 1610. Lower surface 1612 may define a flat planar surface for engaging an external surface of the bone. In other embodiments, lower surface 1612 may be concave to mate with outer surface of target bone. Dome portion 1610 may also include a channel 1614 for receiving a flexible member loop and ends, such as saddle loop 1320a and ends 1324a, 1324b. Channel 1614 may be slightly recessed such that flexible member may at least partially lie within the channel 1614, and therefore reduce palpability. Channel 1614 extends from at least two openings 1615a, 1615b that extend through dome portion 1610. Openings 1615a, 1615b define slotted openings that receive a flexible member loop therethrough, such as loop 1320a, after construct 1300 has been at least partly assembled within the patient.

Post 1620 is configured to extend along bone tunnel and may help to center the anchor 1600 within the bone tunnel. Post 1620 may include bilateral channels 1622a, 1622b, for receiving lengths of the flexible member 1320 therein. Post 1620 may be tapered and may be a length and diameter sized to fit within the target bone tunnel. For example, post may be 0.120 inches long, and have maximum diameter near the done 1610, about 0.122 inches. Dome 1610 may have an outer peripheral diameter of 0.375 inches. Dome portion 1610 may include two apertures 1618, that may receive another flexible member therethrough (not shown). This other flexible member may couple to another portion of the tissue within or adjacent or the joint. Apertures 1618 may also operatively couple to an anchor management handle, similar to handle 3610 to store anchor 1600 during the procedure. Since the anchor is fairly small, a handle 3610 may also store the anchor 1600 in an orientation that helps couple the anchor with the flexible member of the repair construct.

Figure 17:
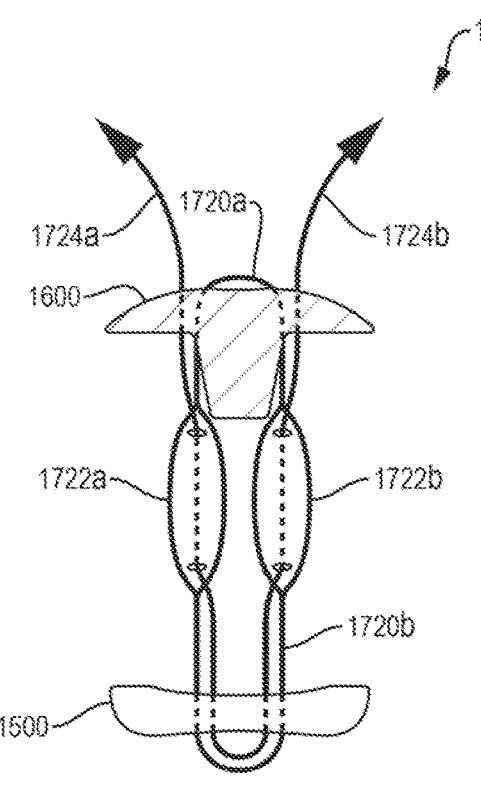
FIG. 17 illustrates an adjustable repair construct in accordance with this disclosure.

FIG. 17 illustrates an example embodiment of repair construct similar to construct 1300. Repair construct 1700 includes a flexible member 1720 with two locking passages 1722a, 1722b. As provided flexible member 1720 may be pre-assembled to cortical anchor 1500, via apertures 1540a, 1540b. Flexible member 1720 may define a double adjustable looped end 1720b, where each loop extends through both apertures 1540a, 1540b. Each of the two adjustable loops extend from both suture locking passages 1722a, 1722b and towards looped end 1720b. A saddle loop end 1720a extends directly from both suture locking passages 1722a, 1722b and defines a fixed loop length. A first reduction limb 1724a of the flexible member 1720 extends from the first suture locking passage 1722a and a second reduction length or limb 1722b extends directly from the suture locking passage 1722b, both extending towards the saddle end 1720a.

The plurality of apertures through cortical anchor 1500 may each receive the two strands of flexible member 1720 therethrough. The cortical anchor 1500 may include a concave bone engaging surface 1520. The cortical anchor 1500 may define a semicircular cross section. The cortical anchor cross section may be configured to matchingly mate with an inner circumference of an inner bore surface of an insertion instrument shaft. The cortical anchor 1500 may define a cross section that fills approximately half of a bore cross section of an insertion instrument shaft, leaving a remaining side free for housing the adjustable loop construct 1720. The saddle end 1720a may assemble to another cortical anchor 1600. Tension on the first and second reduction lengths 1724a, 1724b may reduce the two adjustable loops of the double adjustable looped end 1720b.

Insertion instrument may be configured to place button 1500 and flexible member 1720 through at least one bone and onto an external surface of a second bone. For example, insertion instrument may be configured to place button 1500 and flexible member 1720 through a tunnel through the clavicle 18 and then through a tunnel through the coracoid 22 and onto an external inferior surface of the coracoid. Button 1500 may then be pushed out of the bore 1551 and onto the coracoid external surface, button 1500 having a concave surface 1520 configured to mate with the inferior surface of coracoid 22. Insertion instrument (3600) may then be removed, leaving button 1500 adjacent external inferior surface of coracoid 22, while a saddle loop end 1720a is drawn or placed at superior surface of clavicle 18. Insertion instrument may include a means to maintain hold of saddle loop end 1720a to ensure it remains adjacent the clavicle superior surface (shown in FIG. 36C). Loop end 1720a may then be slide over dome portion 1610 of anchor 1600 to place loop end 1720a through openings 1615a, 1615b and along channel 1614. Tension on ends 1724a, 1724b may reduce the construct 1700 and draw the two anchors (1500, 1600) towards each other. During this step, saddle loop length 1720a remains unchanged. Loop length 1720a is preferably less than 10 mm long.

Construct 1700 may reduce to a reduced configuration that defined a reduced axial length. The reduced axial length is defined by an axial length of the fixed saddle (loop) length 1720a, an axial length of one of the locking passages 1722a, 1722b and an axial length of the adjustable loop end 1720b. Axial length of fixed loop length 1720a is therefore limited in length sufficient to couple to anchor 1600 and yet place the locking passages 1722a, 1722b directly adjacent anchor 1600. This may place locking passages 1722a, 1722b within the bone that the anchor 1600 directly engages, for example, this may place locking passages 1722a, 1722b within clavicle passage of the AC joint. Of note, the axial length of the locking passages 1722a, 1722b may elongate slightly during locking (as part of the locking mechanism), therefore the minimum is defined by the suture locking passages in their locked configuration. This reduced axial length defines the shortest distance between both anchors (1500, 1600), which may be approximately the thicknesses of the two bones for repair, plus any required spacing between these two bones, if appropriate. For example, the minimum axial length between the two anchors 1500, 1600 may be approximately 25 mm.

Figure 18A:
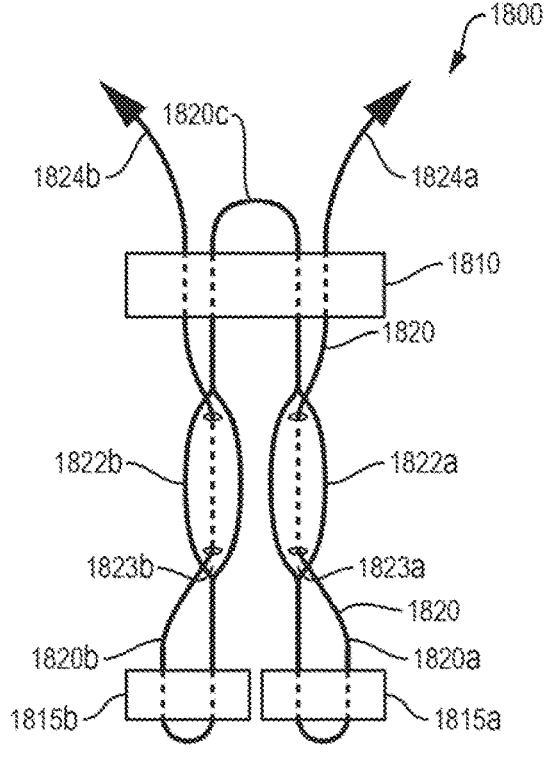
FIG. 18A illustrates an adjustable repair construct, in accordance with this disclosure.
Figure 18B:
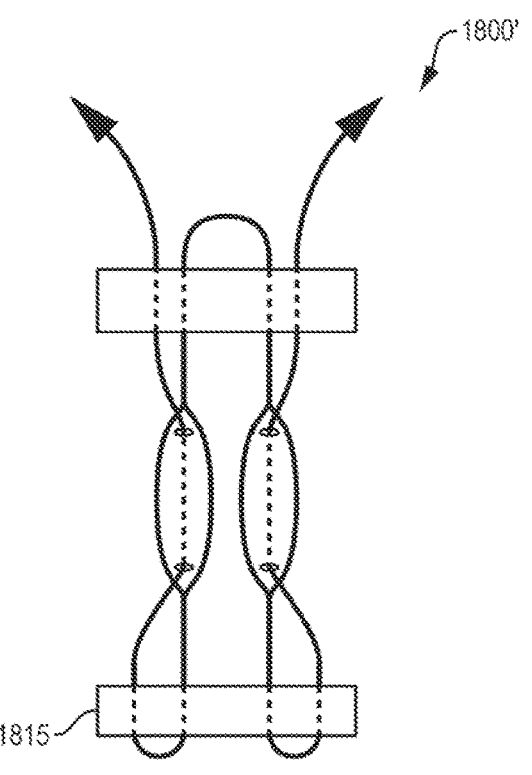
FIG. 18B illustrates an adjustable repair construct, in accordance with this disclosure.
Figure 18C:
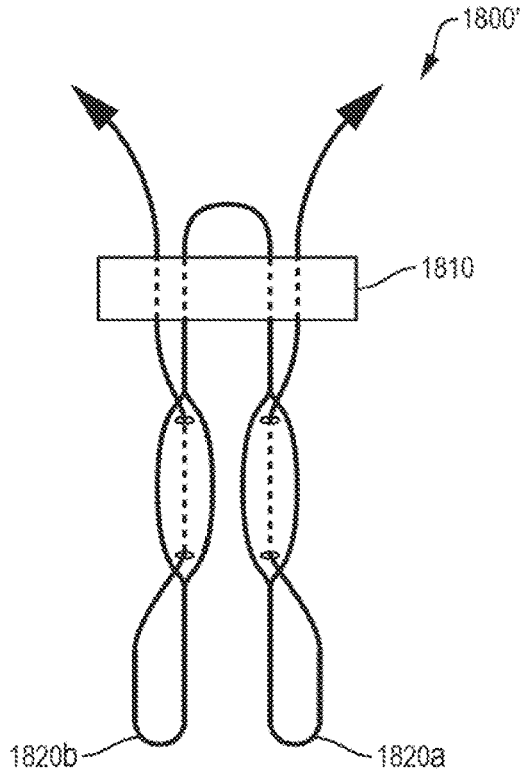
FIG. 18C illustrates an adjustable repair construct, in accordance with this disclosure.

Another example of a repair construct 1200 is shown in a family of embodiments illustrated in FIGS. 18A-18C. Construct 1800, 1800' and 1800" may include at least two anchors, that may be cortical buttons, all-suture anchors, rigid cylindrical anchors or a combination thereof. Construct 1800, 1800' and 1800" may include an adjustable knotlessly locking repair construct with a flexible member 1820 forming two separately adjustable loops, 1820a, 1820b, that are each independent adjustable and knotlessly locking loops. Illustrated in FIG. 18A is an adjustable construct 1800 including a first, second and third anchor 1810, 1815a and 1815b that may be cortical buttons. Flexible member 1820 may be provided operatively coupled or assembled to the buttons 1810 and 1815a, 1815b, via apertures or slots, as described herein. Flexible member 1820 may define at least two discrete suture-locking passages 1822a, 1822b that may extend between the buttons 1810, 1815a, and 1815b. More specifically, flexible member 1820 may define at least two discrete suture-locking passages 1822a, 1822b, a first suture locking passage 1822a extending between and directly from the buttons 1810 and 1815a, and a second suture locking passage 1822b extending between and directly from the buttons 1810 and 1815b. Each locking passages 1822a, 1822b may extend directly from a separate button 1815a, 1815b. Limb 1824a may extend from end 1823a of locking passage 1822a through anchor 1815a, back to end 1823a and through locking passage 1822a, then through anchor 1810. Limb 1824b may extend from end 1823b of locking passage 1822b through anchor 1815b, then back to end 1823b and through locking passage 1822b, then through anchor 1810. Construct 1800 may include a short, fixed length saddle portion 1820c, similar to saddle loop portion 1320a sufficiently long to couple to anchor 1810, while being fixed in length that is appropriate for the repair tissues. For example, in AC joint repair, loop length 1820c is limited in length to place the locking passages 1822a. 1822b as superiorly as possible for better control of the locking passages 1822a. 1822b. Construct 1800 may extend through or around the two bones. Construct 1800 may extend and form a repair construct between three bones, each anchor 1810 and 1815a, 1815b engaging a different bone. Construct 1800 provides for independent reduction. Withdrawing or tensioning limb 1824*a* independently reduces the loop 1820*a* while withdrawing or tensioning limb 1824*b* reduces loop 1820*b*.

A variation of this construct is shown in FIG. 18B, wherein construct 1800' includes only two buttons, similar to construct 1300. Each loop 1820*a*, 1820*b* is coupled to the same anchor. However, the loops 1820*a*, 1820*b* are both independently reduceable and lockable. Construct 1800" may be provided with loops 1820*a*, 1820*b* that are free of any anchor, as provided, giving the surgeon a choice of which and how many anchors to be coupled to the construct.

An example method of joint repair with the constructs 1800, 1800' or 1800" may include forming a single passage through a coracoid 22 and two passages through a clavicle 18. Anchor 1810, assembled to a flexible member 1820 may engage the coracoid 22, with the flexible member 1820 extending through the single passage through the coracoid 22 and then separating. A looped end 1820*a* may then extend along a first of the two passages through the clavicle 18 and a second looped end 1820*b* along a second of the two passages through the clavicle 18. The looped ends (1820*a*, 1820*b*) may be free of an anchor 1815*a* or 1815*b* or may be provided preassembled to them. The two passages through the clavicle 18 may correspond with the trapezoid ligament and conoid ligament attachment locations and/or the ligament vectors relative to the clavicle, for example. As explained previously, two links between the coracoid 22 and clavicle 18 may better simulate or mimic the stiffness vectors of the original trapezoidal and conoid ligaments (CC ligaments). Multiple links between the two bones may improve surgical outcomes. Each looped end (1820*a*, 1820*b*) may then be coupled to their respective locations along the clavicle, via an anchor (1815*a*, 1815*b*). The two passages may be formed using a guide, such as guide 1100.

Another example method of joint repair with the construct 1800 may include forming a single passage through a first bone, and a single passage through a second bone. Both passages may be axially aligned. Passages may be formed with a drill. Two anchors 1815*a*, 1815*b* may then be passed through both passages. Both anchors 1815*a*, 1815 may be passed sequentially, such that the passage opening size (diameter) may be kept small. For example, an inserter similar to inserter 3600 may house each anchor (1815*a*, 1815*b*) axially aligned with each other and axially spaced from each other. Both anchors 1815*a*, 1815*b* may be pre-assembled to a flexible member 1820. Both anchors 1815*a*, 1815*b* may be deployed at a single exit of the passage through the second bone, with the flexible member 1820 extending through both passages. Anchor 1810 may be provided assembled to a saddle end 1820*c* of flexible member 1820 and may engage the entrance to the first bone passage. Tension on ends 1824*a*, 1824*b* may shorten each loop 1820*a*, 1820*b* and reduce the distance between the two bones or two bone portions and hold the bones in the repaired arrangement. Anchor 1810 may be provided separately and may be assembled to the saddle end 1820*c* during the repair. Passing each anchor 1815*a*, 1815*b* sequentially may keep the passage sizes smaller through the two bones, which may reduce fracture of these small bones. However, placing two anchors 1815*a*, 1815*b* side by side at a single bone passage exit forms a combination anchor, within an increased footprint, therefore increasing the anchoring strength of the repair.

Another method of AC joint repair with the construct 1800 may include forming a single passage through a coracoid 22 and a single passage through a clavicle 18, both passages being preferably axially aligned. Both anchors

1815*a*, 1815*b* may then be passed through the two passages. Both anchors 1815*a*, 1815 may be passed sequentially, to keep the passage opening size (diameter) minimal. Given that the coracoid 22 is a small fragile bone, it is advantageous to keep the passage therethrough minimal. Both anchors 1815*a*, 1815*b* may be deployed at the coracoid inferior passage exit with the flexible member construct 1820 extending through both passages. Anchor 1810 may be provided assembled to flexible construct 1820 and may then engage the clavicle superior surface. Tension on ends 1824*a*, 1824*b* may shorten each loop 1820*a*, 1820*b* and reduce the distance between the two bones. Anchor 1810 may be provided separately and may be assembled to the saddle end 1820*c* during the repair. Passing each anchor 1815*a*, 1815*b* sequentially may keep the passages sizes smaller through the two bones, which may reduce fracture of these small bones. However, placing two anchors 1815*a*, 1815*b* side by side increases the surface area of the combination anchor, therefore increasing the anchoring strength.

Another example of a repair construct 1200 is illustrated in FIG. 19. Like elements are allocated like reference numerals, relative to FIG. 12. Illustrated is an adjustable construct 1900 including at least two anchors 1210, 1220 that may be cortical buttons. Adjustable construct 1900 also includes at least one flexible member 1920 that may operatively couple to the buttons 1210 and 1220 via apertures or slots, similar to other flexible repair constructs described herein. Flexible member(s) 1920 may define at least two discrete suture-locking passages 1922*a*, 1922*b* that may extend between the buttons 1210, 1220. Construct 1900 may include a plurality of adjustable loops that extend both through and/or around the buttons 1210, 1220 and also through the suture-locking passages 1922*a*, 1922*b*. Suture locking passages 1922*a*, 1922*b* may have multiple lengths of flexible member 1920 traversing therethrough. Construct 1900 may be similar to construct 1300, except where construct 1300 forms a single adjustable loop, and therefore the suture locking constructs 1322*a*, 1322*b* locks around a single length of the flexible member 1320, construct 1900 forms two adjustable loops and each suture locking construct 1922*a*, 1922*b* locks around two lengths of the flexible member 1920. This construct 1900 may provide benefits in overall device stiffness while providing varying attachment options.

Another example of a repair construct 1200 is illustrated in FIG. 20. Like elements are allocated like reference numerals, relative to FIG. 12. Adjustable construct 2000 may be assembled to all anchors 1210, 1220 during the procedure, and therefore may be provided free of anchors pre-assembled. Flexible member 2020 may define at least two discrete suture-locking passages 2022*a*, 2022*b* and a plurality of adjustable loops 2020*b*, 2020*c* that are reduceable. Adjustable loops 2020*b*, 2020*c* may couple to at least one anchor. Suture locking passages 2022*a*, 2022*b* may have multiple lengths of flexible member 2020 traversing therethrough. Construct 2000 may be similar to construct 1900, as both suture locking constructs 2022*b*, 2022*b* locks around two lengths of the flexible member 2020. This construct 2000 forms two independently reduceable spliced loops 2020*b*, 2020*c*. Saddle 2020*a* is fixed in length, similar to saddles looped ends 1320*a*, 1820*c*.

Turning now for FIGS. 21A-21F, in some examples of repair construct 1300, at least one of the anchors 1310, 1315 may be an all-suture anchor, similar to anchor 310. Anchor 310 may be inserted within a bone or placed on an external surface of a bone to anchor therewith. Repair construct 1300 may therefore be provided at least partially assembled to an anchor inserter 2160, configured to insert and deploy anchor 310, the inserter 2160 similar to inserter 560. Inserter 2160 may also be operatively coupled to the flexible member 1320 to actuate locking passages 1322a, 1322b. This may require additional staging or management means to first deploy anchor (310, 1315) and then actuate the suture-locking passages 1322a, 1322b. Since both may be actuated via tension on the same flexible member, the actions need to be staged. Without any staging means, tension on member ends 1324a and 1324b may simultaneously deploy the anchor and cinch the—locking passages 1322a, 1322b and potentially frustrate the construct. For example, the suture-locking passages 1322a, 1322b may lock the repair construct 1300 before the anchor 310 has fully deployed, risking anchor strength. Shown in FIG. 21A, inserter 2160 is shown with a repair construct 1300 (not shown) housed therein. Inserter 2160 includes a shaft 2165 that has a length configured to extend through a first and second bone (30, 32). Tunnels or passages may be drilled, punched or tapped before extending the inserter shaft 2165 therethough. In some example methods, a partial tunnel may be formed in the second structure 32, such that tunnel is a blind hole. This may be similar to the method disclosed in FIGS. 7A-7D. Inserter 2160 may form part of system 500. The inserter handle 2170 may be operatively coupled to flexible member 1320 to deploy the soft anchor 310 to a laterally or radially expanded state, as disclosed in at least at least U.S. Pat. No. 9,962,149, herein incorporated by reference in its entirety.

Flexible member 1320 may form two passes through the anchor 310, defining four lengths of the flexible member 1320 extending from anchor 310. Flexible member 1320 may be threaded between braids of the soft anchor 310. In FIG. 4A flexible member 315 makes a single pass through anchor 310, defining two lengths of the flexible member 315 extending proximally therefrom. In construct 1300 four lengths may extend from anchor 310 and along the entire length of shaft 2165 such that both locking passages 1322a, 1322b are housed within the handle 2170. A length of the flexible member 1320 between the locking passages 1322a, 1322b and anchor 310 is preferably engaged by the inserter deploying mechanism to deploy the anchor 315. This avoids inadvertent knotless locking of the construct 1300 before complete anchor deployment.

Figures 21A, 21B, 21C, 21D, 21E:
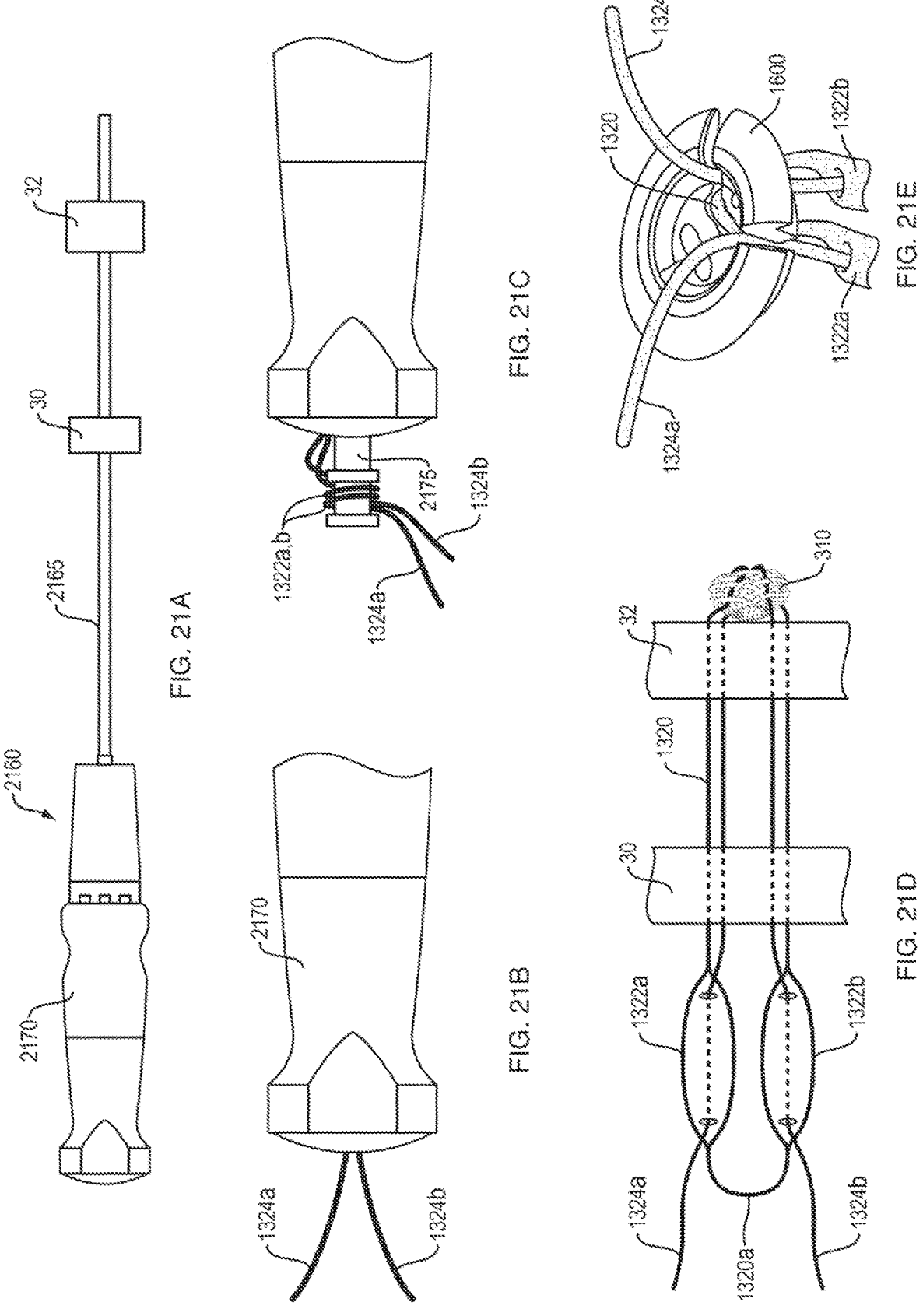
FIGS. 21A-21F illustrate an instrument and associated method for staging deployment and locking of an adjustable knotless locking construct for repair of two bones, in accordance with this disclosure.
Figure 21F:
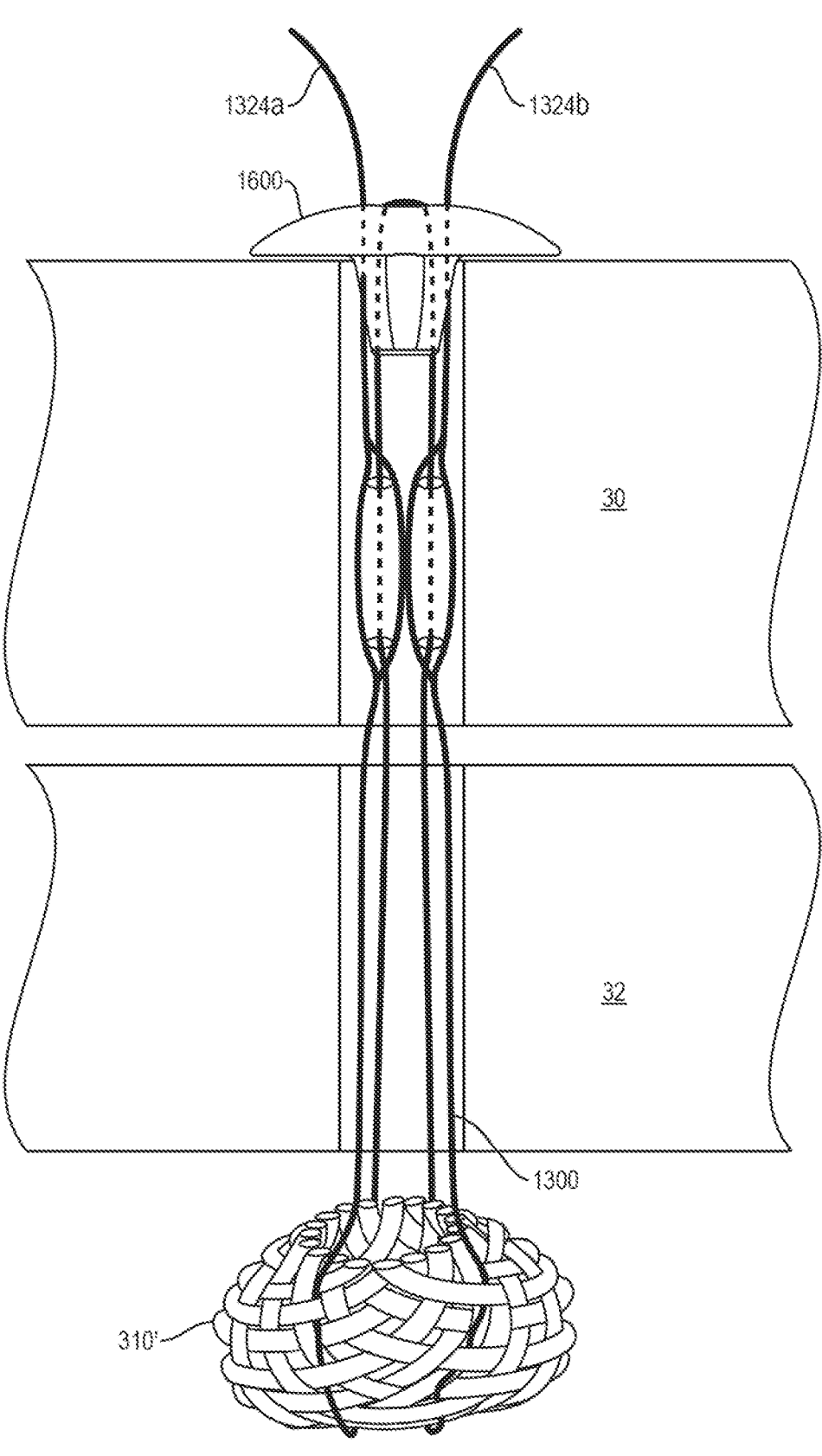

FIG. 21B illustrates handle 2170 with flexible member ends 1324a, 1324b extending proximally therefrom. During anchor deployment, flexible member ends 1324a, 1324b and locking passages 1322a, 1322b are stored in a manner that prevents tension thereon, avoiding inadvertent actuation thereof. Ends 1324a, 1324b and locking passages 1322a, 1322b may be wrapped around a post 2175 proximal to the handle mechanism (not shown) that deploys anchor. FIG. 21C illustrates handle 2170 having deployed the anchor 310. In this configuration post 2175 of handle 2170 may translate proximally, providing access to the ends 1324a, 1324b and locking passages 1322a, 1322b. Of note, this embodiment does not include a pre-assembled anchor 1220, 1310. Once deployed, locking passages 1322a, 1322b may be unwrapped or removed from handle 2170. Inserter 2160 may then slide over flexible member 1320 to remove inserter 2160 from the construct 1300. Removing the inserter 2160 leaves a deployed all-suture anchor 310 engaged with bone 32 and flexible member 1320 extending through both structures 30, 32. Passages 1322a, 1322b may extend proximally from bone 30, as illustrated in FIG. 21D. Bones 30, 32 may include two bones, such as the coracoid and clavicle bones. Anchor deployment means may operatively couple to a portion of the flexible member 1320 that extends directly between the suture locking passages 1322a, 1322b and the anchor 310. This will allow tension on the four lengths of flexible member 1320 to deploy the anchor 310 while shielding the suture locking passages 1322a 1322b from tension, thereby avoiding inadvertently locking the repair construct 1300. An anchor, such as anchor 1600 may then be assembled to saddle 1320a, as illustrated in FIG. 21E. Tension on ends 1324a, 1324b may reduce the distance between deployed anchor 310' and anchor 1600, and thereby hold joint in the reduced configuration. Further tension on ends 1324a, 1324b may knotless lock the repair, illustrated in FIG. 21F.

Another example repair construct 2200, that may include an all-suture anchor 310 is shown in FIG. 22. Construct 2200 may include a deployment member 315, separate from flexible member 1320. This separates the anchor deployment means (315) from the reducing and locking loop, which may simplify the system. Anchor 310 may therefore be deployed first by tension on ends of member 315, as disclosed herein. Tension on deployment strand 315 may deploy anchor 310 while adjustable loop 1320 remains static or inert. Once the anchor 310 is deployed, deployment member 315 may be removed from anchor 310. In this construct flexible member 1320 may be operatively coupled to anchor 310 by interweaving, similar to that shown in FIG. 4A. Flexible member 1320 may only partially interweave along a proximal portion of the anchor 310, sufficient to couple the flexible member 1320 to anchor 310 but limiting adding bulk associated with flexible members 1320 extending through anchor 310. Additional flexible members through the anchor 310 may cause a binding and tangling of the flexible members (315, 1320), which may frustrate the flexible members from sliding, potentially frustrating anchor deployment or reduction of the construct 1300. An example inserter instrument that manages construct 2200 may be similar to instrument 560 and 2160. The example method may be similar to the method disclosed herein in FIGS. 21A-21F, except where noted. For example, the method may include inserting the anchor 310 of construct 2200 through at least a first bone 30 and at least partially through a second bone 32. Anchor 310 may be placed on an external surface of bone 32 or be embedded within bone 32. During insertion, flexible member 1320 including locking passage(s) 1322a, 1322b and anchor 1310 (1410, 1500, 1600) may be at least partially housed within a portion of the shaft and/or inserter handle of instrument. For example, inserter instrument may house the flexible member 1320 including locking passage(s) 1322a, 1322b and anchor 1310 (1410, 1500, 1600) in a handle housing with a releasable cover upon deployment, similar to the systems disclosed in commonly owned PCT publication No. WO2021/243062, titled "Tissue Repair System", herein incorporated by reference in its entirety.

Deployment member 315 may be actuated to deploy the anchor 310. Once deployed, member 315 may be removed from anchor 310. Once deployed, flexible member 1320 including locking passage(s) 1322a, 1322b and anchor 1310 (1410, 1500, 1600) may be retrieved from a housing of inserter. Since deployment is independent of the construct 1300, flexible member 1320 and locking passage(s) 1322a, 1322b and anchor 1310 (1410, 1500, 1600) may be housed along the inserter and may be distal to the deployment actuation location. This construct 2200 avoids the need for a tension managing means, similar to post 2175. After deployment of anchor 1310, tension on suture ends 1324a, 1324b may draw the anchor 1310 towards deployed anchor 310' and thereby first and second bones 30, 32 may be held in the reduced, repaired arrangement, similar to the methods disclosed previously.

Another example of a repair construct 1200 is illustrated in FIG. 23. Construct may include an all-suture anchor 310 and a second anchor 2310 that may be a cortical button anchor, similar to anchor 1410, 1500 or 1600. Flexible member 2320 may be provided operatively coupled to both anchors 310, 2310. Flexible member 2320 may include a single locking passage 2332. Construct 2200 may be configured to reduce and knotlessly lock two tissues relative to each other. For example, construct 2300 may reduce and fix two bones of the AC joint relative to each other after an AC joint dislocation. This construct 2300 may form a single adjustable loop 2320a between the suture locking passage 2332 and anchor 310. This may reduce the complexity of the construct 1200 and the number of suture limbs to manage. This may also lower the volume of the construct, leaving less implanted material. In addition, this may allow for a smaller profile delivery system and/or allow multiple repairs to be placed in a smaller region. Furthermore, a single loop 2320a through an anchor, such as a soft anchor 310 may reduce the complexity deploying the anchor. For example, some existing soft anchors are preassembled with a single length of a flexible strand such as member 315; the same flexible member 315 may form construct 2200. In addition, a single end 2330a may both deploy the anchor 310, reduce the loop 2320a perimeter and then lock the locking passage 2332, therefore allowing a one-handed actuation, which gives the user a free hand to conduct other activities.

Illustrated in FIG. 23 adjustable loop construct 2300 has a fixed end 2330b that may be fixedly coupled to anchor 2310. Fixed end 2330b may be fixed using crimps, adhesive, welds or knots. Fixed end 2330b may extend through at least one aperture of the anchor 2310. Fixed end 2330b is coupled using a knot 2336. Knot 2336 may abut a lower side of anchor 2310. Anchor 2310 may include a recess to receive and hold at least a portion of the knot 2336 therein. In other embodiments, anchor 2310 may be provided separately from loop construct 2330, and fixed end 2330b may be provided with a loop formed by knot 2336, which may be looped over and through slotted openings through the anchor 2310. This may allow a method that includes first, coupling anchor 310 to a first tissue such as with a coracoid 22, followed by detaching an insertion instrument from the deployed anchor 310' before coupling a fixed end 2330b to a second anchor 2310, such as anchor 1600.

Some repair constructs 1200 may repair more than two bones. In some repair constructs 1200 a single locking passage on one side may be sufficient, or multiple splices on a single side. The locking passages may be of differing lengths. Construct 1200 is configured to increase procedural speed. Construct 1200 may reduce the use of metallic or rigid elements, when an all-suture anchor is incorporated.

FIG. 24A illustrates an alternative soft anchor 2410, before deployment. FIG. 24B illustrates the soft anchor 2410 in a deployed configuration 2410'. Soft anchors similar to anchor 2410 are disclosed in commonly assigned U.S. Pat. Nos. 8,795,334 and 10,010,314 commonly owned and herein incorporated in its entirety. Anchor 2410 may be formed of suture, suture tape or ribbon, and may be folded over itself to form a laterally expanded and deployed configuration. Anchor 2410 may deploy to have a profile or thickness that stands less proud of the bone than other soft anchors, such as anchor 310. Anchor 2410 may include treated portions to add rigidity to target portions of the soft anchor 2410. This may increase anchoring strength. For example, portions of the soft anchor may be heat treated, or adhesive may be added, or tubular sleeves or rings of material may be selectively added along the length of anchor 2410.

Figure 25:
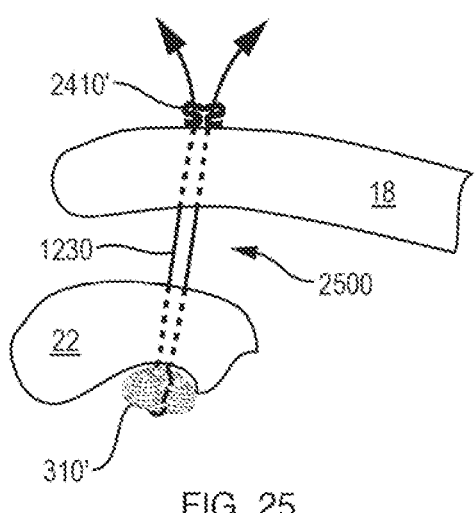
FIG. 25 illustrates an AC joint, in a repaired arrangement assembled to a tissue repair construct including two all-suture anchors in accordance with this disclosure.

Another example repair construct with two all-suture anchors is illustrated in FIG. 25. Like elements are allocated like reference numerals, relative to construct 1200. Illustrated is an adjustable repair construct 2500 including a first all-suture anchor 310 and a second all-suture anchor 2410. Construct 2500 may include a flexible coupling member 1230. Coupling member 1230 may be preassembled to at least one of the first or second all-suture anchors (310, 2410). Coupling member 1230 may form at least one adjustable loop and may include at least one locking passage similar to locking passage 1322a for example. Tension on the coupling means 1230 may deploy at least one of the soft/all-suture anchors (310, 2410). The first and second anchors may be different configurations from each other. One of the first and second soft anchors may be a lower profile all-suture anchor in its deployed state than the other of the first and second all-suture anchors. The first anchor 310 may be embedded within a bone, and the second anchor 2410 may engage a bone external surface, and therefore operate in a similar manner to a cortical button.

While it is preferable to have some flexibility in the repair construct to account for movement in the joint, the inventors have found that flexible members, such as sutures or suture tapes may stretch or relax during physiological loading. In some anatomy, such as the anatomy of the shoulder, a repair undergoes significant loads with use. For example, the weight of the patient's arm alone adds a load on the repair, with normal use of the arm lifting or carrying items adding to that load. As another example during an ankle syndesmosis repair, stress on the repair may come while bearing weight on the leg associated with the repaired ankle. When a repair construct includes a flexible member to reduce and hold two or more bones relative to one another, the positioning of the two bones may shift over time due, at least in part, to elongation or relaxing of the flexible member. Therefore, there is a need for a construct that balances repair flexibility while compensating or limiting strain along the repair construct. This may be achieved by limiting an axial length of the flexible member so that it provides sufficient flexibility or movement between the two bones, while limiting the length of material available to stretch or elongate. Therefore, the axial length of the flexible member along the repair defines a lower or first axial length limit that provides sufficient flexibility to the repair/joint and an upper or second axial length limit to curb elongation. In general, this may be achieved by linking the flexible member between the two bones for only a short axial length of the repair construct. These may include repair constructs that preferably include anchors configured to couple to the flexible linking member ends at locations that place the flexible members ends close to each other. For example, for an AC joint, the anchors may be configured to place one end of the flexible member adjacent to or at a passage opening that is at the clavicle inferior surface and the other end of the flexible member adjacent to or at a passage opening at a coracoid superior surface.

Figure 26A:
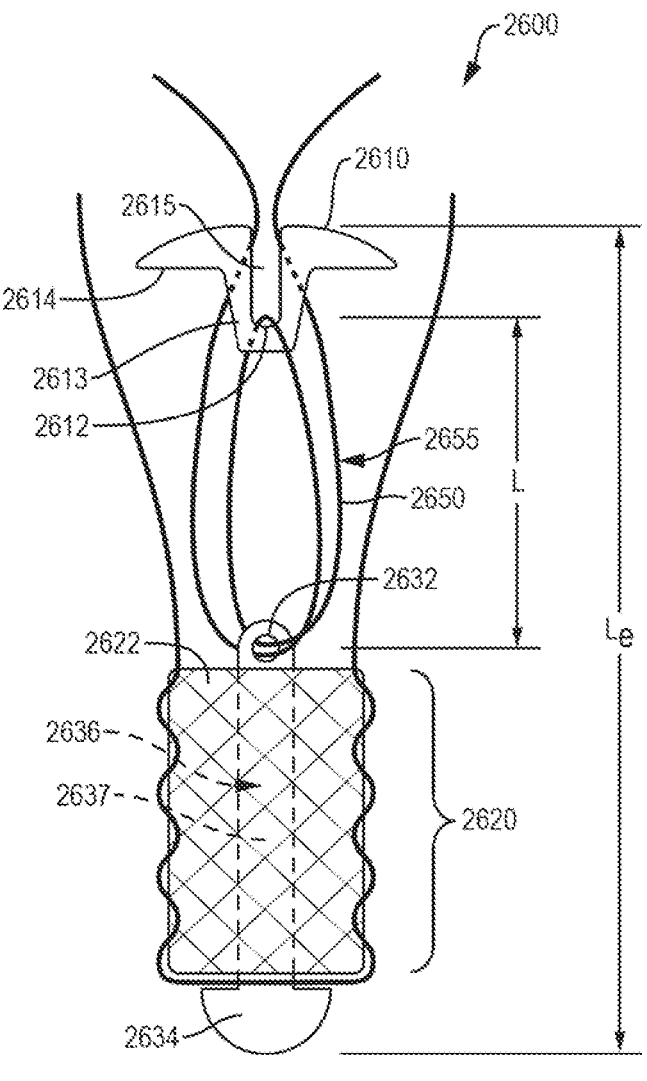
FIG. 26A illustrates a repair construct that limits a length of the flexible link between the two anchors in accordance with this disclosure.
Figures 26B, 26C, 27:
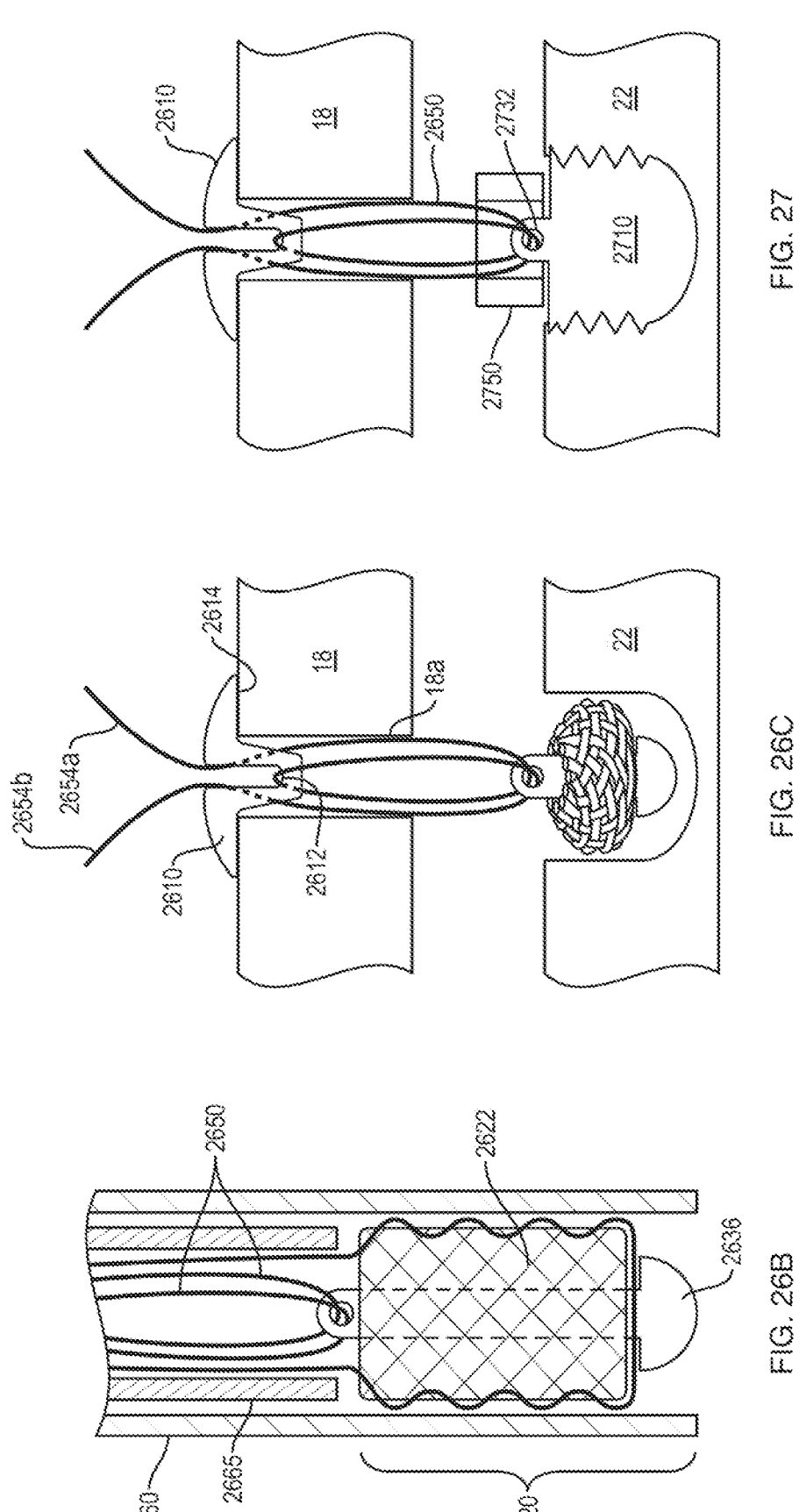
FIG. 26B illustrates the repair construct illustrated in FIG. 26A, housed within an insertion instrument in accordance with this disclosure.
FIG. 26C illustrates the repair construct illustrated in FIG. 26A, assembled with two bones to hold the two bones in a repaired arrangement, in accordance with this disclosure.
FIG. 27 illustrate another repair construct that limits a length of the flexible link between the two anchors in accordance with this disclosure.

An example repair construct that may be configured to limit elongation thereof is illustrated in FIGS. 26A-26C. This repair construct 2600 may engage the bones at a first location and couple to the flexible linking member at a location configured to limit an axial length of the flexible linking member along the repair construct. In general anchors are considered rigid or at least more resistant to elongation relative to the flexible member. This construct 2600 is configured to place ends of a flexible member loop 2655, that links the two anchors 2610, 2620 as close to each other within the limits of the anatomy, and thereby limit the axial length (L) of flexible member loop 2655 relative to the whole construct axial length (Le). Length L and Le are measured axially and in the final repaired (reduced) configuration. Similar to construct 1200, construct 2600 includes a first anchor 2610, a second anchor 2620, and a flexible member 2650 operatively coupled to both anchors (2610, 2620). First anchor 2610 may engage a first bone, while the second anchor 2620 may engage a second bone. Flexible member 2650 may form an adjustable loop construct, with locking passage (not shown) similar to constructs 1300, 1700 or 1800. Anchors 2610, 2620 may be cortical button anchors, all-suture anchors, rigid cylindrical anchors, or a combination thereof. However, anchors 2610 2620 preferably have suture pulley portions defining axial limits of the flexible coupling member between the two anchors (2610, 2620). Suture pulley portions are configured to limit the axial length (L) of the flexible member loop 2655.

In this example, first anchor 2610 may be a cortical button style anchor that engages an external surface of one of the bones of the joint with flanged surface 2614. Anchor 2610 may also include a post 2613 extending from flanged surface 2614, in a similar manner to anchor 1600. Post 2613 may be configured to extend along a passage through the first bone. Anchor 2610/Post 2613 is configured to resist elongation of the repair construct under physiological loading. Post 2613 may include a first suture receiving slotted aperture 2612, that may extend transversely through post 2613 and may define a first end of the flexible connection between the two anchors. In this embodiments, slotted aperture 2612 defines a first pulley end of flexible loop 2655. Preferably post 2613 extends along a passage through the bone and to disposes slotted aperture 2612 close to the other bone of the repair, and thereby closer to the second anchor 2620. Slotted aperture 2612 is configured to receive at least one length of the flexible member 2650 therethrough. Post 2613 is preferably equal to or slightly shorter than a thickness of the bone with which it is to be anchored, such that post 2613 remains recessed therewithin. This is illustrated in FIG. 26C. For example, anchor 2610 may be anchored with the clavicle 18, and surface 2614 may engage an exterior superior surface of the clavicle 18, and slotted aperture 2612 may be recessed within a tunnel 18a through the clavicle 18 such that is it directly adjacent but slightly recessed from an inferior surface of the clavicle 18, as shown in FIG. 26C. First anchor 2610 may also include a recess 2615 for recessing a knot (not shown), for repairs where tying a knot is required to secure or lock the repair construct. Ends 2654a, 2654b may be tied to form the knot.

The second anchor 2620 may engage a coracoid 22. Second anchor 2620 may be an all-suture anchor, similar to anchor 310. Second anchor 2620 may be a cortical button style anchor, with a post similar to first anchor 2610. Second anchor 2620 may be inserted through at least one passage through bone, and therefore may preferably be a small profile anchor. Second anchor 2620 may be elongate or oblong in shape, similar to anchor 1410, 1420, but with the addition of a post or hook (not shown) that positions the suture pulley portion axially closer to the first anchor 2610. Shown in FIG. 26A, second anchor 2620 may include a soft anchor (310) operatively engaged to a rigid pin 2636. Rigid pin 2636 is configured to have a resistance to elongate greater than flexible member linking loop 2655. Pin 2636 may be formed from PEEK. Rigid pin 2636 includes an aperture 2632 that defines the second pulley end of the adjustable flexible loop 2655. Pin aperture 2632 is configured to receive at least one length of the flexible member 2650 therethrough. Aperture 2632 may be at a proximal end of anchor 2620 and may be proximally spaced from all soft anchor 310. In some embodiments aperture 2632 may be at the proximal most end of anchor 2620. Pin 2636 may define head 2634 configured to abut a distal end of all-suture anchor 310. Pin 2636 may define a shaft 2637 configured to extend along soft anchor 310, aperture 2632 disposed through the shaft 2637. Continuing with the example above, second anchor 2620 may be configured to couple to the coracoid 22 and couple to flexible member 2650 at a location adjacent a superior surface of coracoid 22. While it may be preferable to keep the distance between the first and second flexible loop ends as close as possible, in some anatomical locations rigid components may preferably not extend into the space between the two bones. In some embodiments, ends of the flexible loop 2655 may be coincident with facing external surfaces of the two bones. Stated another way, first and second loop ends of flexible member may be directly adjacent the tissue external surfaces, and no portions of either anchor, including pin 2636 or post 2613 lies proud of the corresponding bone the anchor is inserted into. Aperture 2632 may be coincident with a superior surface of the coracoid.

In FIGS. 26A-26C, rigid pin 2636 may extend through a lumen of anchor 310 and may define a transverse hole/pulley for coupling to the flexible strand. Flexible strand 2650 may be a tape that tends to be more resistance to strain or elongation and therefore reduce potential displacement between the two bones over time. Seen in FIG. 26B, anchor 2620 may be inserted with insertion instrument 2660 similar to system 305. Instrument 2660 may house anchor 2620 within an outer tube, and push anchor 2620 into the target bone via push rod 2665. Using system 500, anchor 2620 may be inserted through a passage through first bone such as the clavicle 18, and into or through second bone, such as the coracoid 22.

FIG. 26B illustrates a joint held in a repaired arrangement with repair construct 2600. An associated method may include fixing a first end of a flexible member of a repair construct with a first bone and a second end of the flexible member with a second bone, the fixing at locations configured to limit an axial length of the flexible member and thereby limit elongatino along the flexible member. Fixing may include anchoring a first anchor with the first bone and a second anchor with the second bone, the first and second anchor configured to place ends of the flexible member at locations to limit the axial length of the flexible member coupling the two bones. Fixing the first anchor may include inserting the first anchor through a passage through the second bone and then into the first bone, with the flexible member end coupled thereto. Fixing the second anchor may include inserting a portion of the second anchor operatively coupled to the flexible member into the second bone and towards the first anchor followed by anchoring the second anchor to the second bone. Fixing the first and second end may place the ends of flexible member at or adjacent to facing entrances of passages through first and second bones.

FIG. 27 illustrates a repair construct 2700, similar to repair construct 2600. Like components are given the same numerical identifiers. Shown in FIG. 27 the second anchor 2720 may be a rigid anchor with an aperture 2732 integral with anchor 2720. Second anchor may be formed of PEEK. Second anchor 2720 may include external ridges, threads, barbs or wings 2722 that are configured to anchor within the second tissue and inhibit withdrawal of the second anchor therefrom. Second anchor 2720 may be configured to partially anchor within second tissue such that a portion of the second anchor 2720 remains external to the second tissue, placing the aperture 2732 closer to aperture 2612. Alternatively, anchor 2720 may be inserted into the second tissue to place aperture 2720 at external surface of the second tissue. This may depend on the anatomy being repaired and the target spacing for the tissue reduction. In addition, a bumper 2750 may space the two anchors (2610, 2720), to maintain a minimum distance between the two bones (18, 22). Bumper 2750 may be a soft tubular or annular component that protects the two bones from the more rigid components of anchor 2720.

Further repair constructs and components thereof that may resist elongation are illustrated in FIGS. 28A-29B. Tissue repair constructs 2800 and 2800' may be similar to construct 1200 and include two anchors and a flexible member linking construct therebetween. In this embodiment, repair constructs 2800 and 2800' may include a continuous fixed loop (CL) suspensory system, such as the one offered by Smith and Nephew. Repair Construct 2800, 2800' may include a continuous loop 2855, 2855', 2855" that may offer a non-adjustable flexible member loop and are free of knots or locking passages (such as those described herein). This may resist elongation due to any slipping of the knots or finger traps. Continuous loops 2855 2855', 2855" may also be thicker in strand diameter than traditional sutures, that may inherently improve resistance to strain. Continuous loops 2855, 2855', 2855" may have a solid cross section packed with strands and therefore free of voids or lumens along the flexible member core that may improve its resistance to elongation. Continuous loops 2855, 2855', 2855" are provided in a variety of lengths (2855, 2855', 2855"), to approximate typical repair distances for the target procedure. However, these finite number of lengths, illustrated in FIG. 28A may be slightly too short or long for the preferred reduction distance between the two bones. Disclosed herein are a plurality of anchor embodiments that, when assembled to the continuous fixed length loop, interact with the continuous loop to incrementally adjust the effective spacing distance between the two bones of the joint.

Figures 28A, 28B, 28C:
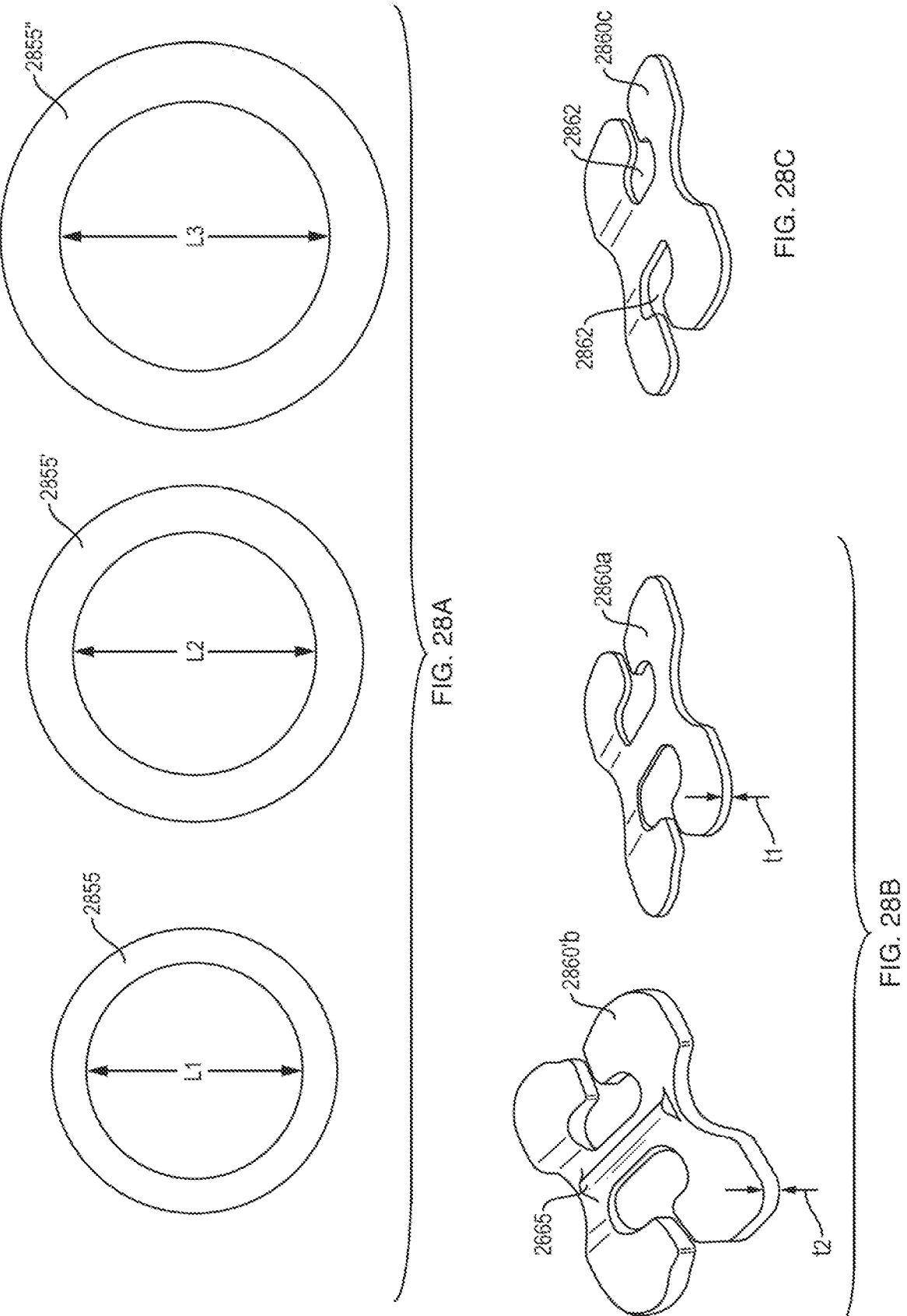
FIG. 28A illustrates a plurality of continuous loops with different lengths (or loop diameters), in accordance with this disclosure.
FIG. 28B illustrates a plurality of cortical anchors with continuous loop adjusting means, in accordance with this disclosure.
FIG. 28C illustrates another embodiment of a cortical anchor with continuous loop adjusting means, in accordance with this disclosure.

These repair constructs, such as construct 2800 and 2800' includes a continuous loop suspensory system in which the overall construct length is adjusted by the judicious selection and assembly of a second anchor that adjusts the repair construct length for the target tissue spacing. Second anchor may be a button with open slots to receive the selected flexible continuous loop 2855, 2855', 2855" therethrough. For example, second anchor may include one of a plurality of cortical button anchors 2860a, 2860b, 2860c each provided with a means of effectively reducing the axial length of the loop 2855 between the two bones. For example, this means of reducing may include thickness of anchor; for example, anchors 2860a has a greater thickness t2 than anchor 2860b with a thickness t1. A thicker anchor requires a longer portion of the loop 2855 to wrap over the anchor, and therefore reduces the distance between the two bones relative to a thinner anchor. Another means in addition to or instead of increased thickness, may include a rib 2865 extending along a portion of the anchor 2680a, instead of or in addition to an increase in thickness. This has the benefit of limiting the added volume of a foreign body within the patient. Other means may include axially offsetting the two open slots 2862 as shown in FIG. 28C to increase the path length of the continuous loop around the anchor 2860c.

In other procedures, the anchor may include a means of incrementally increasing the effective length of the repair construct. For example, this means of increasing may include an anchor with a loop pulley that is axially recessed along the repair axial length. An example button may include a recess, similar to anchor 1600 or 2610 and may extend into and along a tissue tunnel.

Therefore, the inventors envision a repair construct with a flexible link that is provided as a continuous loop and operatively couples to two anchors. At least one of these anchors may be preassembled to the continuous loop 2855, 2855' or 2855". At least one of these two anchors may be configured to adjust the effective axial length of the repair construct when assembled and thereby incrementally compensate for the fixed axial length of the continuous loop. Stated another way, at least one of these anchors includes a repair construct length adjustment means or fine-tuning means that is static and an integral part of the anchor.

Figure 29B:
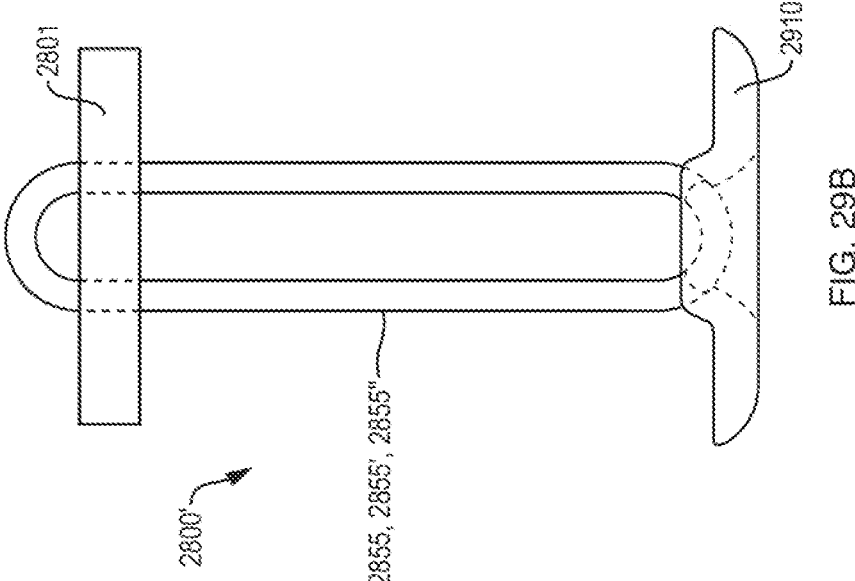
FIG. 29B illustrates a repair construct with a continuous loop and at least one anchor including loop adjusting means, in accordance with this disclosure.
Figure 29A:
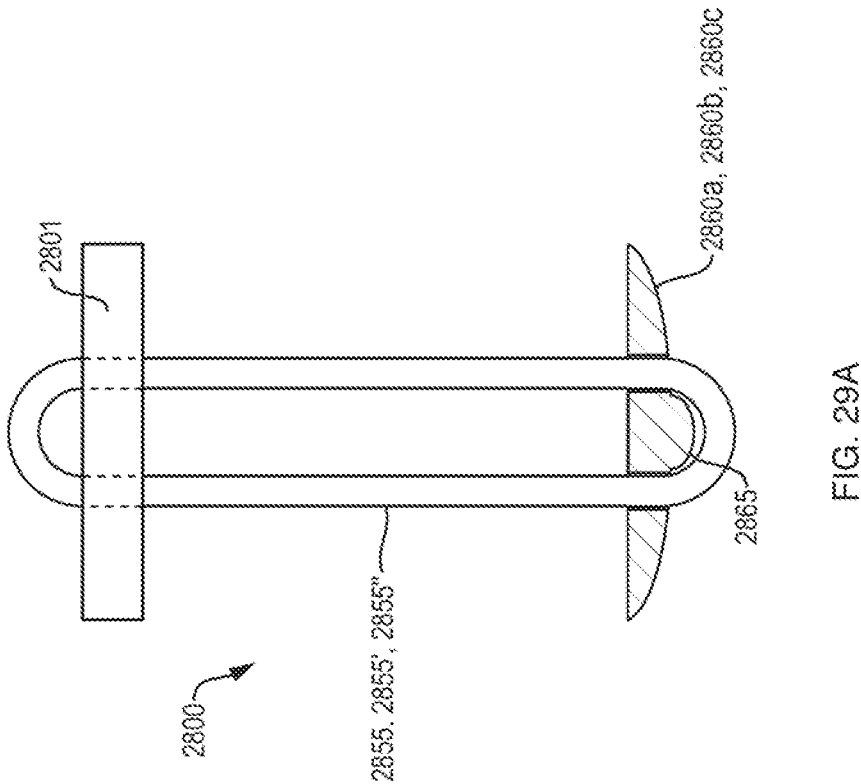
FIG. 29A illustrates a repair construct with a continuous loop and at least one anchor including loop adjusting means, in accordance with this disclosure.

For example, the final construct may be similar to that shown in FIG. 29A. Final construct 2800 may include a first anchor 2801, a continuous loop 2855, 2855' or 2855" and a second anchor configured to adjust the repair construct axial length and compensate for a continuous loop that, in the example, is slightly too long for the target repaired anatomy spacing. An example method of spacing a first bone relative to a second bone may include reducing the clavicle 18 towards the coracoid 22 in AC joint repair. Repair construct 2800 may include an integrated cortical button 2801 of fixed thickness, similar to button 1400 or 1500 for example, provided preassembled with the loop 2855, 2855' or 2855". A target repair distance may first be determined between the clavicle 18 and coracoid 22 in the reduced configuration. This determined distance may be measured from an inferior side of the coracoid 22 to a superior surface of the clavicle 18. A fixed continuous loop length correlating closest to this determined distance may then be selected. In this example shown in FIG. 29A, the continuous loop 2855, 2855', 2855" closest has an effective length that is slightly too long to arrange the two bones at the preferred spacing. The second button, such as button 2860a or 2860b or 2860c is then selected, that adjusts the effective repair construct length towards the determined distance. Second button 2860a or 2860b or 2860c may be an open button that is assembled to the continuous loop 2855, 2855' or 2855" during the procedure via open lateral slots. The open button 2860a or 2860b or 2860c is selected and integrated to the construct 2800 from a selection of buttons having variations in adjustment lengths. The selection of buttons may all vary in thickness from each other for example. This range of button thicknesses, in combination with available closed loops 2855, 2855' or 2855" available in varying lengths, allows for the fine-tuning of the overall effective length of the construct. Button 2801 may be placed on a superior surface of clavicle 18. It is preferable to have a thin button on the clavicle surface, reducing any prominence on the clavicle 18, which can be a source of irritation to the patient and adversely affect cosmesis. The second anchor including the adjustment means is formed as a single body.

In order to determine the length of the construct, a measurement of the distance between the inferior surface of the coracoid to the superior side of the re-approximated clavicle may be taken. This may be achieved using the drill and guide (and/or drill/bullet/guide), similar to guide 500 disclosed herein. The proposed measurement technique does not require direct visualization of the inferior surface of the coracoid while taking the measurement, and the incorporation of a ratchet bullet to the guide providing assistance in holding to clavicle in the reduced state while taking the measurement. With the clavicle reduced, a drill, similar to drill 550 may include incremental markers or numerical indicators indicative of length may be inserted through the clavicle and then through the coracoid. This may be done arthroscopically and may provide a target length from the inferior surface of the coracoid to the superior surface of the clavicle. Drill gradations could also be read through holes in a fenestrated bullet that interfaces with the guide and drill (fenestrated bullet not shown).

Repair construct 2800', shown in FIG. 29B, may include a first anchor 2801, a continuous loop 2855, 2855' or 2855" and a second anchor configured to adjust the repair construct length and compensate for a continuous loop that is slightly too short for the target repaired anatomy spacing. Second button 2910 may be an open button similar to button 1600, that is assembled during the procedure via open lateral slots. The open button 2910 is selected and integrated to the construct from a selection of buttons having variation in adjustment means. That is to say, the selection of buttons may all vary in recess depth from each other for example. This range of button recess depth, in combination with closed loops 2855, 2855', 2855", allows for the fine-tuning of the overall effective length of the construct. Repeating a similar example method previously disclosed, button 2801 might be placed on an exterior surface of a first bone. The second anchor 2910 with the length adjusting means may be placed on an exterior surface of the second bone.

Continuous loops 2855, 2855, 2855" may be available in 5 mm increments in loop diameter. Buttons (2860a, 2860a, 2860c, 2910) may be provided with adjustments in 1 mm increments, from approximately 1 mm to 5 mm in one of both directions (thickness or recesses). The combination of 1 mm incremented adjustment means, with continuous loops in 5 mm increments provides fine-tuning of the overall construct length to within 1 mm of the desired construct length. In some example constructs, both anchors may be selectable and assembled to the continuous loop during the procedure.

Figure 30:
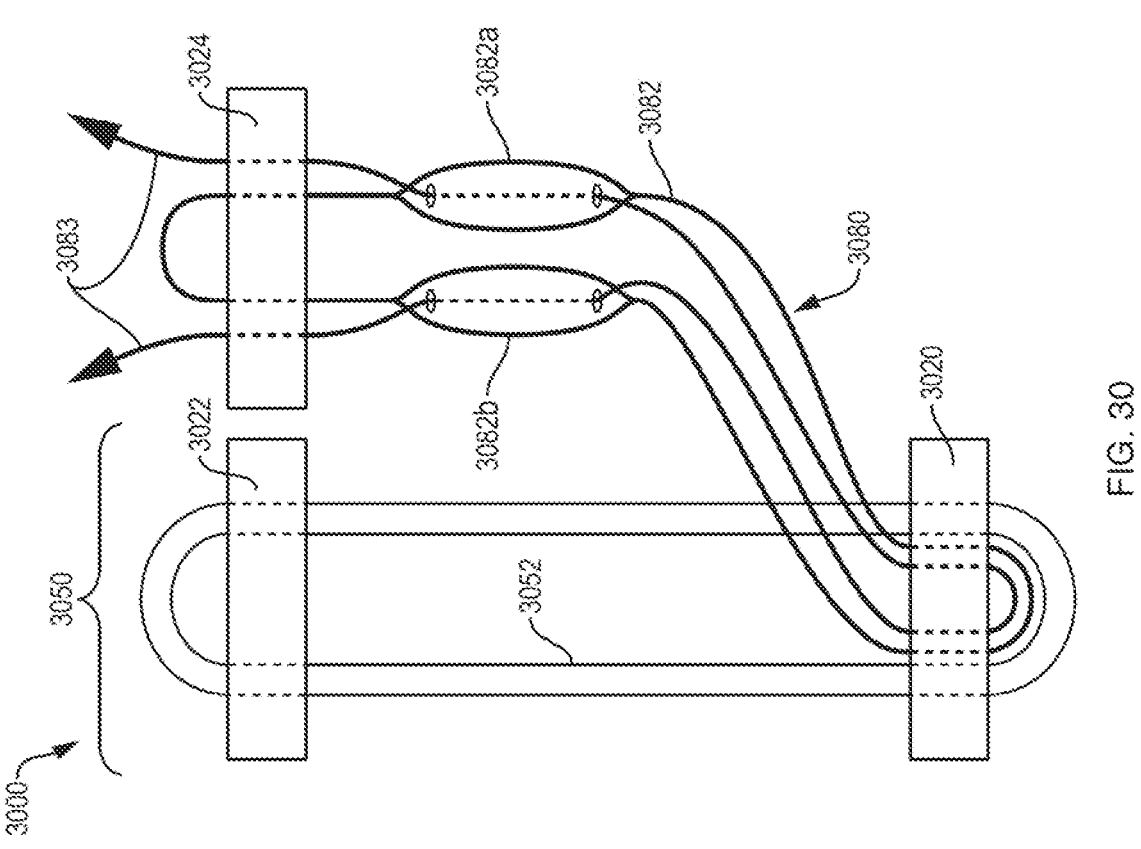
FIG. 30 schematically shows a repair construct that includes two flexible member links extending from a common bone anchor, in accordance with this disclosure.

Building on the concept shown in FIG. 28A-29B, another example repair construct 3000 is illustrated in FIG. 30. Construct 3000 may include two connections to a bone, including a continuous closed loop 3050 and an adjustable loop 3080. The loops 3050 and 3080 may share at least one anchor 3020. As disclosed earlier, the continuous closed loop (CL) construct 3050 may provide superior stiffness and creep properties; however, it does not facilitate adjustment. Construct 3000 may provide two links between any two anatomical structures requiring repair. Construct 3000 may provide two links between the two bones such as the coracoid 22 and clavicle 18, which may simulate or mimic the stiffness vectors of the original trapezoidal and conoid ligaments (CC ligaments). Multiple links between the two bones may improve surgical outcomes. A first link may include a non—adjustable construct 3050 and may simulate a more superior-inferior oriented link, such as the trapezoidal ligament. A second link may include an adjustable loop construct 3080 and may include an anterior-posterior component to the link. This may simulate the conoid ligament orientation for example. Both constructs 3050 and 3080 may couple to a single anchor 3020.

The repair construct 3000 may include three cortical buttons, 3020, 3022 and 3083. Button 3022 may be an open or closed button. Closed buttons may include apertures therethrough that are 360 degree bounded holes and are provided coupled to the continuous loop 2855, 2855', 2855". In contrast, an open button may have at least one open aperture such as a lateral slot and therefore may have a boundary that is not a 360 degree bounded hole, such that a flexible strand of the loop may be assembled to the button during the repair procedure. Button 3022 may be similar to closed button 1500 or open button 1600, 2860a, 2860b, 2860c for example. Loop 2855, 2855', 2855" may be selectable according to a predetermined anatomical repair length similar to construct 2800 and 2800'. Button 3022 may be flipping button, defined as a button anchor that has shape such that in a first orientation it fits along and through a bone tunnel or passage. Button 3022 may then be flipped to a second orientation that engages an outer surface of the bone and no longer fits within the bone tunnel. Flipping buttons may be oblong shaped. Button 3022 may include loop adjusting means, similar to buttons 2860a, 2860b, 2910. All buttons 3020, 3022, and 3024 may include a plurality of apertures or slots, for operatively coupling (either preassembled or assembled during the procedure) to flexible members.

Button 3020 may be an open and/or closed button, as defined herein. Button may partially be a closed button, in that it may be provided preassembled via 360 degree bounded holes to flexible member 3082 and may also include open slots that may assemble during the procedure to continuous loop 2855, 2855', 2855". Button 3020 may be selectable to compensate and fine tune length of loop 2855, 2855', 2855", and therefore may be an open button, configured to assemble during the procedure to both loop 2855, 2855', 2855" and flexible member 3082. Button 3020 may be flipping button as defined herein. Button 3020 may include a plurality of apertures or slots for receiving flexible members therethrough.

Button 3024 may be an open and/or closed button, as defined herein. Button may be similar to button 1600. Adjustable loop 3080 may be formed from at least one flexible member 3082 that extends between button 3020 and 3024. Two reduction limbs 3083 of member 3082 extend from button 3024. Adjustable loop 3080 may include at least one locking passage 3082a, 3082b that may selectively lock the adjustable loop as disclosed herein. Repair construct 3080 may be similar to construct 1300.

Figure 31:
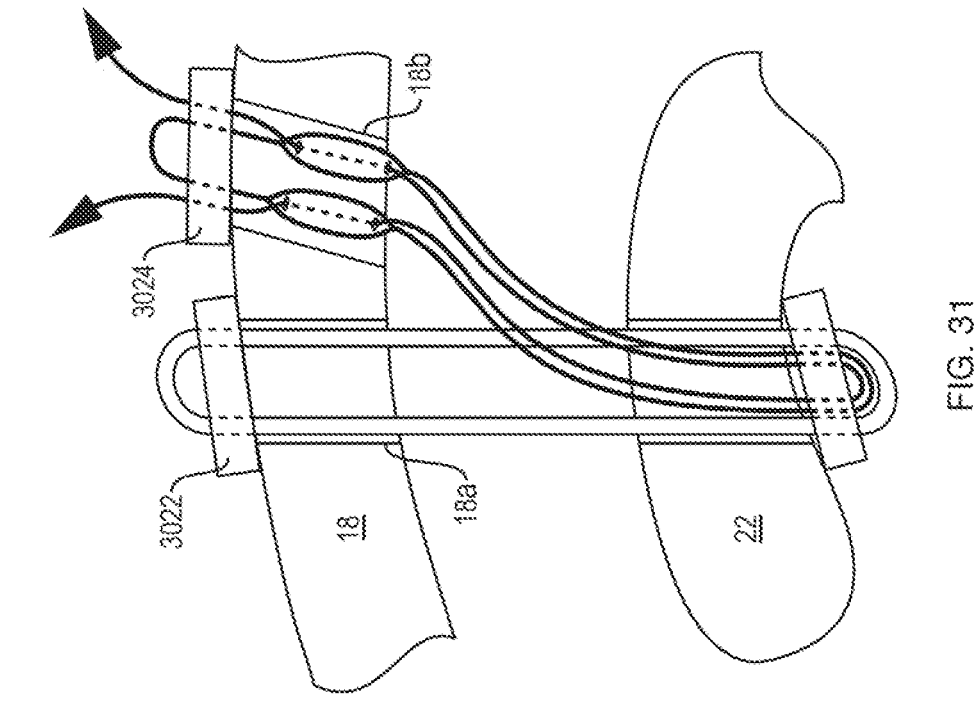
FIG. 31 illustrates the repair construct shown in FIG. 30 assembled to two bones of a joint, in accordance with this disclosure.

FIG. 31 illustrates repair construct 3000 assembled to an AC joint. A single bone tunnel may be formed through the coracoid 22 for receiving both constructs 3050 and 3080 and two bone tunnels 18a, 18b may be formed through the clavicle 18. A drill guide, similar to guide 1100 may orient the plurality of bone tunnels relative to each other. A first of the two bone tunnels 18a, through the clavicle 18 may vertically align with the single bone tunnel through the coracoid 22, when the clavicle 18 is in a reduced arrangement. A second of the two bone tunnels 18b may include a posterior-anterior component to its orientation. Stated in another day, the second of the two bone tunnels (18b) may not be vertical. (FIG. 31 illustrates a simplified representation of the AC joint, in 2D form, therefore any posterior-anterior component is not directly shown but represented as tunnel 18b in this figure). Construct 3050 may extend through the coracoid tunnel and first tunnel 18a. Construct 3080 may extend through the coracoid tunnel and second tunnel 18b.

In an example method, a distance between the clavicle 18 and coracoid 22 may be determined and a continuous loop construct 3080 selected that correlates with this determined distance, as disclosed herein. Button 3020 may be selected to fine tune the length of continuous loop 2855, 2855', 2855". Button 3020 may be operatively coupled to flexible member construct 3080. In some example methods, both buttons 3022 and 3024 may be passed superiorly, first through the single coracoid tunnel, from an inferior surface to the superior surface of the coracoid 22. This may be performed simultaneously or sequentially. Button 3024, associated with the adjustable loop construct 3080 may be passed first, from an inferior surface of the coracoid 22 through to the superior surface followed by through the second tunnel 18*b* through the clavicle 18 to place button 3024 on the superior surface of the clavicle 18, while the closed loop 3050 (including button 3022) remains inferior to the coracoid 22. In other example methods, both buttons 3022 and 3024 may be drawn through the coracoid 22 in a single motion and the closed loop construct 3050 including button 3022 may then be released and parked in between the coracoid 22 and clavicle 18, while the adjustable construct 3080 is drawn through one of the clavicle tunnels.

Both constructs 3050 and 3080 may be coupled to button 3020 that may be a static button. A static button 3020 may be defined as a non-flipping button or non-passing button and therefore is preferably configured to remain external to the target bone. Button 3020 may be provided assembled to both flexible members 2855, 2855', 2855" and 3082. In this example method, static button 3020 may be placed on the inferior external surface of the coracoid 22. In other embodiments, static button 3020 may include some closed apertures and some open apertures, such that at least one of the constructs (3050 or 3080) is provided preassembled, while one of the constructs may be assembled by the surgeon, during the procedure. For example, construct 3080 may be provided preassembled with the static button 3020 and the closed loop construct 3050 may be selectively coupled thereto. Having at least one of the loops (3050 or 3080) preassembled to a closed aperture of the button 3020 positively fixes the static button 3020 to at least a portion of the construct 3000 and thereby reduces the potential for the button 3020 to become a loose body.

With the closed loop construct 3050 parked and inferior to at least the clavicle 18, (and possibly also inferior to the coracoid 22), and the static button 3020 on an inferior surface of the coracoid 22 and the button 3024 on a superior surface of the clavicle 18, limbs 3083 may be withdrawn to reduce length of construct 3080. This may reduce the clavicle 18 towards the coracoid 22. The adjustable loop construct 3080 may then be locked via the locking passages 3082*a*, 3082*b* thereby locking the clavicle 18 relative to the coracoid 22. Once the AC joint has been reduced, the closed loop construct 3050 may be passed through the other of the two bone tunnels in the clavicle 18 to the clavicle superior surface. This may be the first or vertical of the two bone tunnels. Having the two bones reduced and fixed in place courtesy of the adjustable construct 3080 makes for easier passing of the CL construct 3050.

After completion of the repair, the CL Construct 3050 supports the majority of the load which is in the inferior/superior direction. This is advantageous because the CL Construct may possess superior strength, stiffness and elongation properties compared with adjustable constructs as explained herein. After providing initial reduction for the repair, if auspiciously placed, the adjustable construct 3080 can subsequently be used to provide anterior to posterior support to the joint. The anterior to posterior support of the clavicle 18 is helpful for enhancing the overall stability of the repair. The anterior to posterior load is significantly lower than the inferior superior load being supported by the CL Construct. The adjustable construct 3080 is able to support this lighter anterior to posterior load without undergoing appreciable construct relaxation.

In alternative embodiments, flipping button 3022, 3024 may be open buttons and placed superiorly without extending through any bone tunnels. These buttons may be similar to button 1800. Construct 3000 may include additional closed or adjustable loop constructs. Buttons may be contoured to better match the intended surface.

Further example repair constructs and associated methods of repair may including placing two anchors through the same tunnel to be placed, side by side at a single exit to the bone tunnel. As explained herein, during some joint repairs, at least one of the bones of the joint may be smaller and more fragile and therefore more vulnerable to any bone tissue being removed, further weakening the bone. Therefore, opening sizes or diameters of any passages or tunnel therethrough are preferably minimized through these bones. However smaller tunnels may limit anchor sizes that may be passed through them, and smaller anchor sizes may not be preferable under higher load joints, such as loads on the AC joint for example. Smaller anchors tend to have a smaller footprint engagement on the cortical bone, which may induce high stress concentrations on the engaged cortical bone, and potential points of bone (or anchor) failure. Therefore, techniques that include forming smaller bone tunnel sizes while using larger anchors may add complexity to the procedure, as this may require accessing the tissue from more complex directions or increased dissection for example.

Figure 32A:
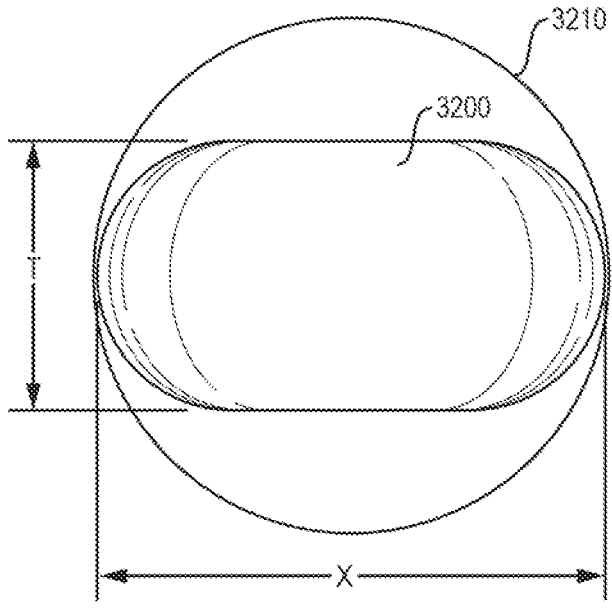
FIGS. 32A and 32B illustrate various views of a cortical button.
Figure 32B:
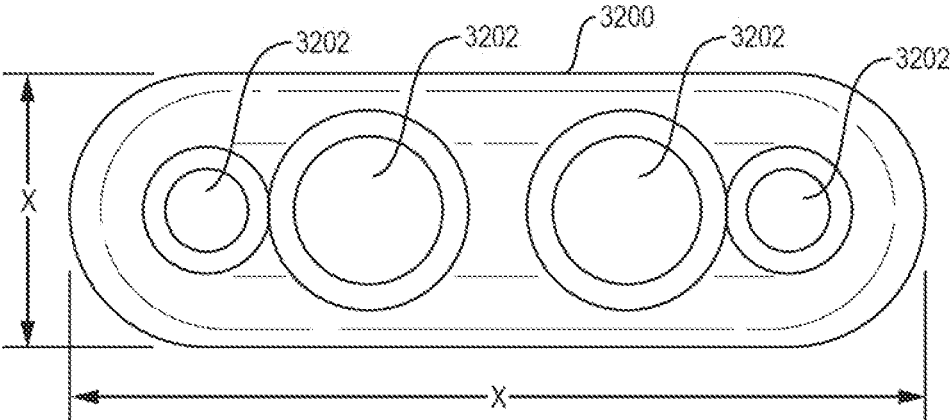

To exemplify the point, an example cortical button 3200 is illustrated in FIGS. 32A and 32B. Button 3200 may have a plurality of apertures 3202 therethrough for coupling to a flexible member (not shown). Cortical button 3200 may be any flipping style cortical button, as defined herein, similar to cortical button 1410, 1420 or 1500, flipping between an elongate orientation (FIG. 32B) and an anchoring orientation (FIG. 32A). Cortical button 3200 defines a length "Y" and a width "X", and a thickness "T". Length "Y" and a width "X" at least partially defines a footprint or surface area of engagement of the button 3200 (or button 1410, 1420 or 1500) with the cortical bone, the larger the footprint the lower (better) the load distribution between the bone and button 3200. The larger this footprint, the lower stress concentration on the bone. Shown in FIG. 32B is the button 3200 in the elongate orientation and a representative bone tunnel 3210. Width "W" is limited by an opening size of the bone tunnel, which therefore defines a first limit on the maximum footprint of the anchor in the anchoring orientation. Length "L" is limited not by the bone tunnel opening size, but by the bone width and shape; the anchor footprint must engage bone to take some of the load. Smaller (narrower) bones only provide a limited cross section for the length "L" to engage. Therefore, for a given bone cross section, which will define a maximum length "L", the footprint and therefore loading on the bone is controlled by "X". However, the larger the width "X", the larger the passage required through the smaller bone.

Figure 33:
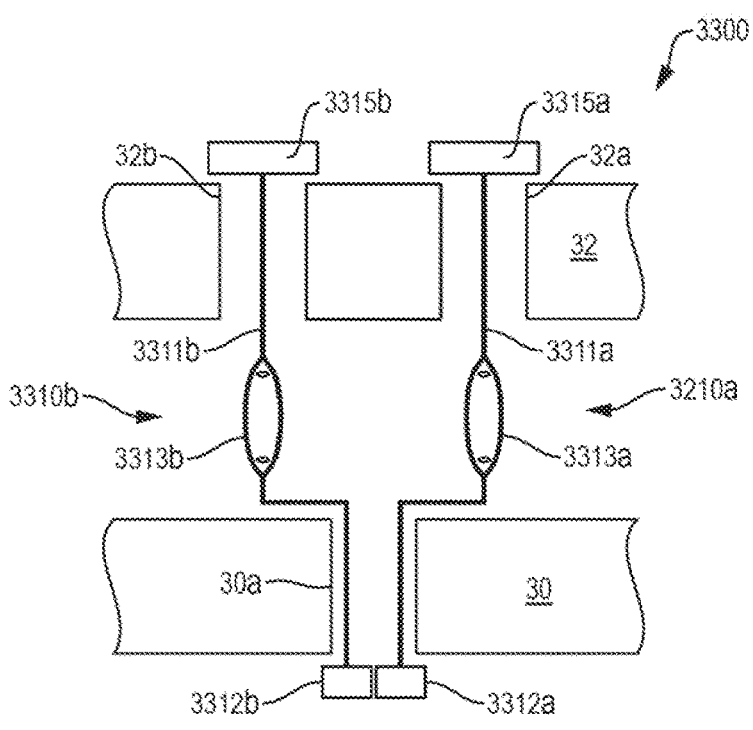
FIG. 33 illustrates a repair construct assembled to two bones of a joint, the repair construct including two independent repair constructs, with anchors at a single exit to a tunnel through one of the two bone, in accordance with this disclosure.

A solution may include placing two smaller anchors adjacent each other at an exit of a single bone tunnel, illustrated in FIGS. 33, 34 and 35A-35B. FIG. 33 illustrates a first example repair construct 3300 for holding two bones of a joint in a repaired arrangement that may include two anchors adjacent each other at an exit of a single bone tunnel. Construct 3300 may include two separate repair constructs. This example repair construct 3300 may include inserting two tissue repair constructs 3310*a*, 3310*b* into a common tunnel through one of the bones, and may include extending the repair constructs 3310*a*, 3310*b* through their own individual tunnel in the other of the two bones. Each repair construct 3310a, 3310b in this example embodiment is formed separately and is its own discrete construct. Each repair construct 3310a, 3310b may be similar to constructs disclosed herein, such as but not limited to construct 1300, 1700, 2200 or 2800. Each construct may be different, in that one may include different anchors that each other, and one may include a knotless locking construct while the other construct may not.

Remaining with FIG. 33, in an example method or repair, each repair construct 3310a, 3310b may be independently inserted and deployed relative to each other. Each construct 3310a, 3310b may include, in its final assembled form, two bone anchors with a flexible member therebetween. Therefore, for two repair constructs there is at least four discrete tissue anchors and at least two flexible members. At least one of the repair constructs (3310a or 3310b) may be similar to tissue repair construct 1300.

In the case of AC joint repair, this double repair construct 3300 may provide two links between the coracoid 22 and clavicle 18, which may simulate or mimic the stiffness vectors of the original trapezoidal and conoid ligaments (CC ligaments). In other anatomies, this construct 3300 may provide two links between any two bones. Advantageously both links couple to a single tunnel through a smaller or more fragile bone, such as, for example the coracoid 22. Multiple links between the two bones may improve surgical outcomes. Multiple links that are formed of separate constructs, each individually coupling to both bones may be easier to manipulate. Multiple independent links may provide some safety factor or redundancy, providing fixation via one of the links, should the other of the two links loosen or fail.

Schematically represented in FIG. 33, a first link between the two structures, that may be first and second bones (30, 32) may include a first repair construct 3310a with a flexible member 3311a that extends through a first tunnel 30a of a first bone 30 and couples via a first anchor 3312a to the first bone 30. Flexible member 3311a may be formed of suture, cable, suture tape or wire for example and form a plurality of adjustable loops that extend along the bone tunnels, similar to at least embodiment 1300 or 1700 for example. Flexible member 3311a may include at least one locking passage 3313a, as disclosed herein. First anchor 3312a may be a cortical button, cylindrical rigid anchor or soft anchor as disclosed herein. The first anchor 3312a may couple to an outer cortical surface of the first bone 30. A second link may include a second repair construct 3310b with a flexible member 3311b that also extends through the first tunnel 30a of the first bone 30 and couples via a first anchor 3312b of the second repair construct 3310b to the first bone 30. Flexible member 3311b may include at least one locking passage 3313b. (FIG. 33 shows repair construct in a simplified form to simplify the figure, but repair constructs may include adjustable loops and locking passages and may be construct 1300, 1700, 1900, 2200, 2800 for example) Flexible member 3311b may form at least one loop that extends between the two bones (30, 32), and couples the two anchors. First anchor 3312b may be a cortical button, or soft anchor as disclosed herein. First anchors 3312a, 3312b may be similar to each other, or different from each other. For example, anchor 3312a may be a cortical rigid button, while anchor 3312b may be a soft anchor. First anchors 3312a, 3312b may lie side by side at the exit to tunnel 30a through first bone 30. First anchors 3312a, 3312b may include keys to lock together, once placed side by side. First anchors 3312a, 3312b may be the two portions of anchor 3700 for example. First anchors 3312a, 3312b may combine to increase the anchoring footprint at the cortical surface, to improve the load distribution between the anchor and bone 3332. If both of the first anchors 3312a, 3312b are soft anchors, they may deform and meld together to sit, side by side, in engagement.

With the two first anchors 3312a, 3312b placed and deployed, the first repair construct 3310a may then couple to the second bone 32 via a first tunnel 32a in the second bone 32. The second tissue repair construct 3310b may then couple to the second bone 32 via a second tunnel 32b. One of the tunnels 32a, 32 may axially align with tunnel 30a, while the other tunnel (3318a, 3318b) may be axially offset and/or angularly offset from the tunnel 30a. One of the links may primarily support the load of the fixation, while the second link may provide anterior to posterior support to the repair. The anterior to posterior support may help the overall stability of the repair. A guide, similar to guide 1100 may be used to orient formation of the two tunnels through the second bone 32 relative to the tunnel 30a through the first bone 30. Each tissue repair construct 3310a, 3310b may couple to the second bone 32 with a second anchor 3315a, 3315b that may be a cortical button, cylindrical rigid anchor or soft anchor as disclosed herein. Each second anchor 3315a, 3315b may be provided preassembled to its respective repair construct 3310a, 3310b, or may be assembled during the procedure, and may be similar to anchor 1600. Similar to the first anchors, the second anchors 3315a, 3315b may couple to an outer cortical surface of the second bone 32. In other embodiments, at least one of the second anchors 3315a or 3315b may engage the walls along the corresponding tunnel and therefore be at least partially recessed. In some example methods, there may be a third tissue repair construct 3310c (not shown), separately formed from the other constructs 3310a, 3310b and also inserted along the first tunnel 30a. The third tissue repair construct 3310c may extend through a third tunnel 3318c (also not shown) through the second bone 32. In further example methods the at least one of the repair constructs 3310a, 3310b, 3310c may form a link between the first bone 30 via the first tunnel 30a to a third bone, different from the first and second bones. For example, during AC joint repair, at least one of the repair constructs 3310a, 3310b, 3310c may link the coracoid 22 to the acromion. In some methods and tissue repair embodiments, the first anchor 3312a may engage the walls along first tunnel 30a and therefore be at least partially recessed within the first tunnel 30a. In alternative methods the first repair construct 3310a may be fully assembled to both bones before assembling the second repair construct 3310b.

Figure 34:
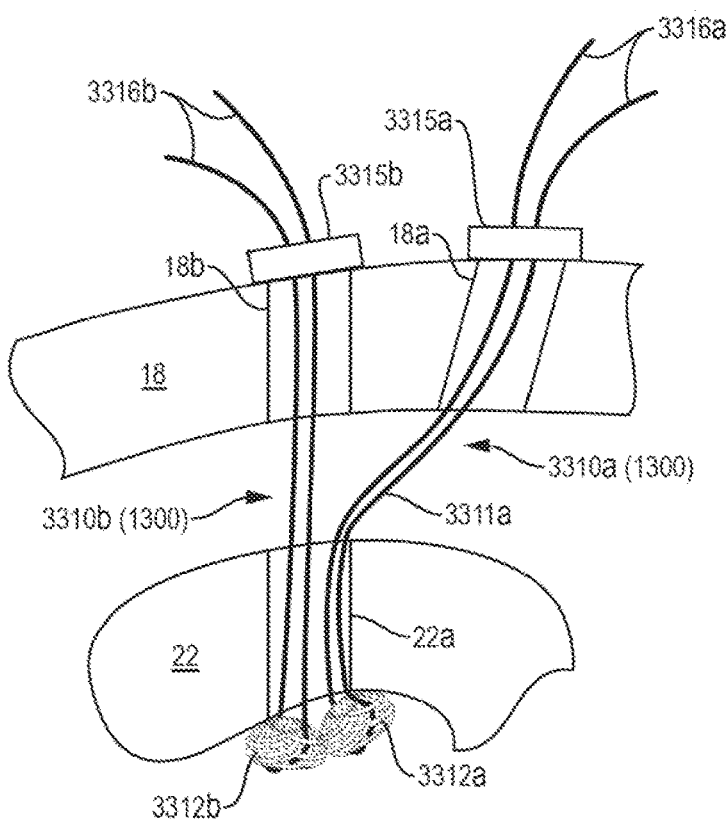
FIG. 34 illustrates an example repair construct illustrated in FIG. 33, with double all-suture anchor fixation at the exit of a single hole through a bone, in accordance with this disclosure.

Turning now to a specific example, illustrated in FIG. 34, and referencing FIG. 33, where like elements are given the same label, the repair construct 3300 may include two separate independent constructs 3310a, 3310b similar to construct 1300, 1700 or 2200. Constructs 3310a, 3310b may be the same or different from each other. Construct 3300, including constructs 3310a, 3310b may hold the clavicle 18 and coracoid 22 (and thereby scapula) of an AC joint in a repaired configuration. Construct anchors 3312a, 3312b may include soft anchors, similar to anchors 310 or 2410. Flexible members 3311a, 3311b may be configured to deploy the soft anchor (310, 2410) upon the application of tension, in a similar manner to flexible member 315. Flexible members 3311a, 3311b may form the link between the two bones (18, 22). Each flexible member 3311a, 3311b may form at least one loop, similar to loops shown in construct 1300 such that at least four limbs extend from each anchor 3312a 3312b (loops not shown for simplicity of the figure).

Constructs 3310a and 3310b are separately formed from each other, such that the constructs 3310a, 3310b may be sequentially coupled to both bones (18, 22). Each construct may include suture locking passages (not shown in FIG. 34 for simplicity of the figure).

An example method may therefore include inserting construct 3310a through a first or medial clavicle tunnel 18a and then through a coracoid tunnel. Inserting may be performed with inserter 2160. Anchor 3312a may then be deployed to operatively couple construct 3310a with the coracoid 22. Anchor 3312a may be an all-suture anchor 310. Proximal end of flexible member 3311a may extend from a superior aspect of clavicle 18. Proximal end of flexible member 3311a may then be assembled to a cortical button, such as button 1600.

The example method may continue to include inserting a second repair construct 3310b through a lateral clavicle tunnel (18b), spaced laterally from medial clavicle tunnel 18a and through the same coracoid hole or tunnel as the construct 3310a. A drill guide and bullet may aid in placing this construct 3310b. A single guide that generates converging holes through one of the bones may be used, similar to guide 1100 for example. Inserting anchor 3312b may include slightly displacing the deployed anchor 3312a to allow passage of the undeployed anchor 3312b through to the inferior exterior side of the coracoid 22. Anchor 3312b may be housed within an inserter distal end while being inserted, similar to inserter system 305 shown in FIG. 4A. Distal end of inserter 305 system may push on and deform and/or reposition the deployed anchor 3312a while placing anchor 3312b. Soft anchors may more readily deform or shift than rigid anchors and retain their ability to anchor with tissues. Anchor 3312b may then be deployed to operatively couple with the coracoid 22. During deployment the two soft anchors 3312a, 3312b may naturally conform around each other to both independently form two separate links between the two bones, while also cooperating with each other to form a larger footprint relative to the bone tunnel diameter and therefore a strong fixation with the coracoid 22. In the deployed configuration the two soft anchors 3312a, 3312b may engage each other, side by side as illustrated in FIG. 34. FIG. 34 schematically shows the repair construct 3300, with some elements such as the plurality of flexible member lengths, multiple loops and locking passages omitted, for simplification of the figure. At least four limbs of flexible member 3311b may extend between coracoid 22 and clavicle 18. Proximal end of flexible member 3311b preferably extends from a superior aspect of a lateral tunnel 18b of clavicle 18. This results in at least eight flexible member limbs in total extending through coracoid tunnel that may link the two bones with each other (four limbs for each construct 3310a, 3310b). Eight strands may improve the load carrying capability of the repair 3300.

Continuing with the specific example method of repair, each construct 3310a, 3310b may be provided (one each) preassembled with a second anchor (3315a, 3315b respectively) or a second anchor may be assembled during the repair. Therefore, the method may include assembling a button anchor 3315a to flexible member 3311a and then assembling a button anchor 3315b to flexible member 3311b. At least one reducing limb, 3316a or 3316b of the corresponding flexible member extends from the corresponding button 3315a, 3315b. The two constructs (3310a, 3310b) may now be reduced and tensioned (via tension on the at least one reducing limb 3316a, 3316) to reduce the spacing between the anchors. Tension on these limbs may lock any corresponding locking passage(s) (3313a, 3313b)

and fix the two bones relative to each other. In some example methods, tension may be incrementally applied to each construct (3310a, 3310b) back and forth, in a rocking type fashion, to reduce the anchor spacing more gradually and evenly between the two constructs 3310a, 3310b. A knot may be tied on the superior aspect of the second anchor (3315a, 3315b) to fix the two bones in position.

Figure 35A:
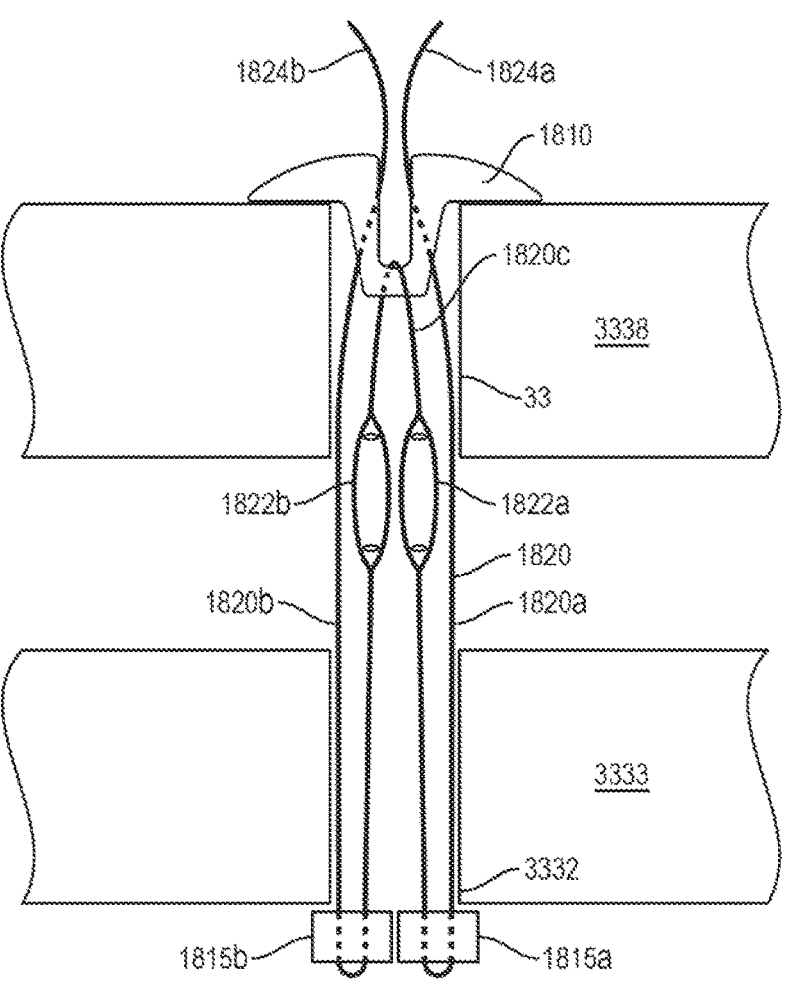
FIG. 35A illustrates a repair construct holding two bones in a repaired arrangement with two anchors disposed at a single exit to a bone, in accordance with this disclosure.
Figure 35B:
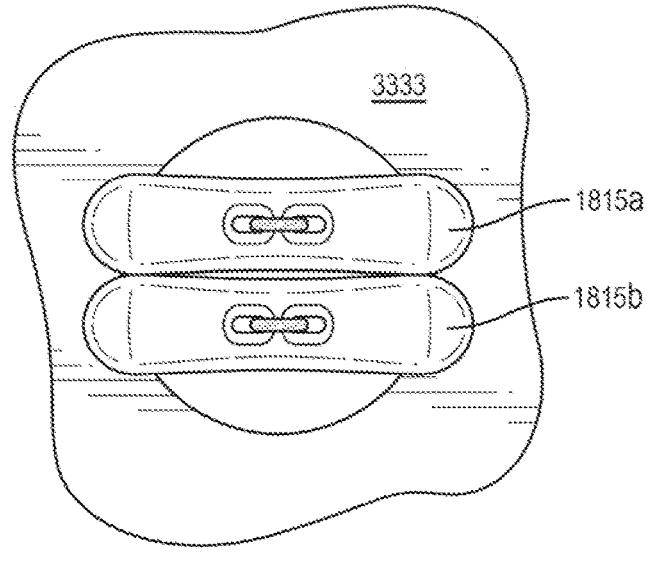
FIG. 35B illustrates a view of the two anchors at the single exit, in accordance with this disclosure.

FIG. 35A illustrates another method of fixing two bones in a repaired arrangement relative to each other, with two anchors placed beside each other at a single exit of a passage through one of the bones. Repair construct 1800 may be provided with the two anchors 1815a, 1815b preassembled to flexible member loops 1820a and 1820b respectively. Anchors 1815a, 1815b may be inserted, sequentially. Construct 1800 may be provided with or without a third anchor 1810 pre-assembled. For example, anchor 1810 may be pre-assembled and similar to anchor 1410 or 1500. In other embodiments, anchor 1810 may include slots, similar to anchor 1600, and be assembled to the flexible member 1820 after anchors 1815a, 1815b has been placed on the external surface of bone 3333.

The method may include inserting anchor 1815a through a tunnel 30a of a first bone 30 and flipping anchor 1815a via tension on loop 1820a. Second anchor 1815b may be inserted through the same bone 30 and same tunnel 30a and then deployed or flipped via tension on loop 1820b. Second anchor 1815b may be inserted before flipping anchor 1815a or afterwards. Anchors 1815a, 1815b individually define a width configured to slide through a small opening size of a tunnel 30a, the opening size of the tunnel 30a limited to reduce volume of bone removed from the bone 30. The anchor width however may be insufficient to withstand expected functional loading between the two bones (30, 32). Anchors 1815a, 1815b in combination when placed beside each other may combine or cooperate to withstand the functional loading between the two bones (30, 32). Anchors 1815a, 1815b may lie directly adjacent each other after deployment, illustrated in FIG. 35B. This may spread the load distribution across a larger surface area. Anchors 1815a, 1815b may have concave surfaces, similar to anchor 1500 to match the target bone contour. This may locate anchor across the target bone longitudinal axis. In some example methods both anchors 1815a, 1815b may be inserted through the bone tunnel 30a and deployed before attaching anchor 1810 at the other end of the construct. Attaching anchor 1810 may include passing saddle loop 1820c through two opposing lateral slots of button 1810. Ends or limbs 1824a, 1824b may then be tensioned to reduce loops 1820a and 1820b. Loop length 1820c (also called a saddle) is fixed in length. Further tension on limbs 1824a, 1824b may actuate locking passages 1822a, 1822b and knotlessly lock the construct 1800. FIG. 35A illustrates a repaired configuration, with both locking passages 1822a, 1822b disposed substantially along a tunnel 32a through bone 32.

Turning now to FIG. 36A, construct 1800 may be manipulated to form a repair as shown in FIG. 35A via insertion instrument 3600. Instrument 3600 generally includes a handle 3610, a shaft 3620 extending distally therefrom, and shaft distal end 3625 housing anchors 1815a, 1815b at least partially therein. Anchors 1815a, 1815b may lie, axially spaced along and within shaft distal end 3625. Flexible member loops 1820a, 1820b and saddle 1820c may all extend along shaft 3620 and may extend along a bore of shaft 3620. Handle 3610 may include at least one actuator 3615 operatively coupled to a means of removing the anchors 1815a, and 1815b from the shaft distal end 3625.

For example, actuator 3615 may retract the shaft 3620, revealing the anchors 1815*a*, 1815*b*. In another example, actuator my advance a push rod distally along the shaft 3620 to push the anchors 1815*a*, 1815*b* out of a stationary shaft distal end. Handle 3610 may also include a means of holding flexible member ends 1824*a*, 1824*b*, sufficient to retain anchors 1815*a*, 1815*b* within shaft distal end 3625. For example, handle 3610 may include cleats for cinching flexible member ends 1824*a*, 1824*b*.

FIG. 36B illustrates a simplified view of distal end 3625 with some of the shaft 3620 removed to view anchors 1815*a*, 1815*b*. Anchors 1815*a*, 1815*b* may be axially aligned and housed within bore 3621 of shaft 3620. Flexible member loops 1820*a*, 1820*b* extend along shaft bore. Locking passages 1822*a*, 1822*b* may be housed within handle (FIG. 36C). Push rod 3628 may extend along shaft bore 3621 and engage a proximal side of second anchor 1815*b*. Ends of anchors 1815*a*, 1815*b* may include a flat or contoured surface configured to improve engagement between the push rod 3628 and anchor 1815*b* and also between mating ends of each anchor (1815*a*, 1815*b*). Improved engagement via matching mating ends may aid during removal from instrument 3600. For example, surfaces 1835*a*, 1835*b* are shown as flat orthogonal surface, relative to a longitudinal axis of each anchor 1815*a*, 1815*b*. Other matching or mating surfaces, such as a concave surface mating with a convex surface, or jigsaw-style mating surfaces are other optional engagement surfaces. Actuating push rod 3628, via actuator 3615 may advance push rod a distance approximately equal to a single anchor axial length to advance a single anchor 1815*a* out of shaft 3620. Reactivating push rod 3628 may then advance the second anchor 1815*b*. In other methods, actuating push rod 3628 may advance push rod 3628 a distance sufficient to advance both anchors 1815*a*, 1815*b* out of shaft 3620 simultaneously, with one actuation of actuator 3615.

FIG. 36C illustrates a cross section of handle 3610. Push rod 3628 extends along handle 3610 and may operatively couple to actuator 3615. Actuator 3615 may be operatively coupled to a spring. Handle 3610 may also include at least one slot/cleat 3614 for holding flexible member limbs 1824*a*, 1824*b*. Locking passages 1822*a*, 1822*b* may be housed in handle. With reference to FIG. 158, anchors may define a semi-circular cross section and sit, similar to button 1500 in a first circumferential side of the shaft bore. This allows sufficient room in the remaining circumferential half portion to house the plurality of loops (1820*a*, 1820*b*) that extend through and proximally from the anchor.

Some embodiments of instrument 3600 may include a means of retaining anchor 1810 within or on the handle 3610. For example, cavities or apertures through anchor 1810 may slide over and engage mating posts on the handle 3610. For example, apertures 1618 through anchor 1600 may engage mating posts (not shown) that extend from a surface of handle 3610. Saddle loop 1820*c* may be provided preassembled to anchor 1810, and anchor 1810 may be retained on or within handle 3610. If preassembled, the flexible member 1820 may require removal via openings or slots (not shown) along the shaft 3620 so that flexible member 1820 may be removed without having the pull the anchor 1810 through the shaft bore 3611. In other embodiments, instrument 3600 may house two separate constructs, similar to construct 3300.

An example method of repairing a joint may therefore include placing an insertion instrument through a passage through a first bone 30. The insertion instrument houses at least two anchors 1815*a*, 1815*b*, each anchor 1815*a*, 1815*b* coupled to at least one flexible member (1820). The method may then include actuating the insertion instrument to place both anchors 1815*a*, 1815*b* at an exit of the first bone passage 30*a*. Both anchors 1815*a*, 1815*b* are then deployed, thereby prevent the anchors from retracting back through the passage exit. The method may then include retracting the insertion instrument 3600 leaving the anchors 1815*a*, 1815*b* at the passage exit with the at least one flexible member 1820 extending along the passage. The method may include placing the insertion instrument 3600 through a passage 32*a* of a second bone 32 before placing the insertion instrument 3600 through first bone passage 30*a*, both passages being axially aligned. The method may include placing the anchors 1815*a*, 1815*b* with flexible member 1820 housed within insertion instrument 3600, the insertion instrument also holding a third anchor 1600. After the anchors 1815*a*, 1815*b* are deployed, the insertion instrument 3600 may be withdrawn to place a saddle end 1820*c* at a proximal aspect of second bone 32. Saddle end 1820*c* may be operatively coupled to anchor 1600. Tensioning flexible member ends 1824*a*, 1824*b* may reduce repair construct. Reduction may include first tensioning end 1824*a* and thereby reducing first loop 1820*a* of construct 1800 and then tensioning end 1824*b* and thereby reducing second loop 1820*b* of construct 1800. Reduction may be a rocking, back and forth action. Once in the reduced configuration, tension on ends 1824*a*, 1824*b* may actuate locking passages 1822*a*, 1822*b*.

Figure 37A:
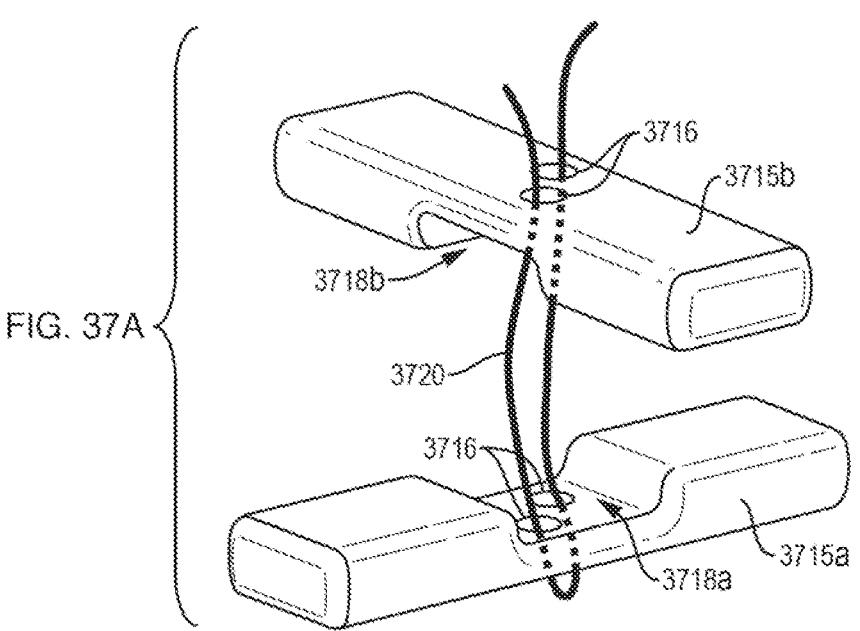
FIG. 37A illustrates a repair construct end with a combination anchor for placing at a single passage exit of a bone, in accordance with this disclosure.
Figure 37B:
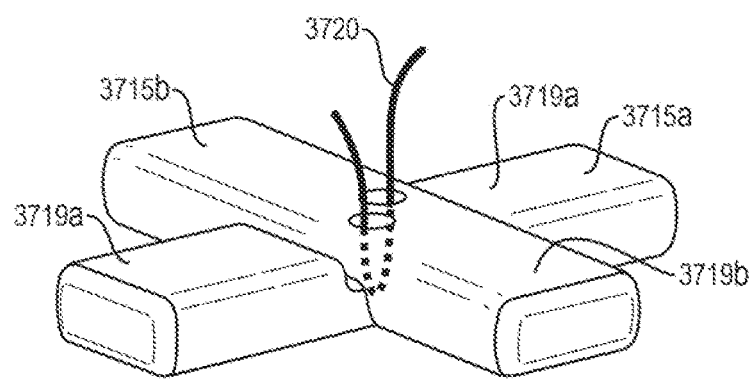
FIG. 37B illustrates the repair construct with the combination anchor in an assembled configuration, in accordance with this disclosure.
Figure 37C:
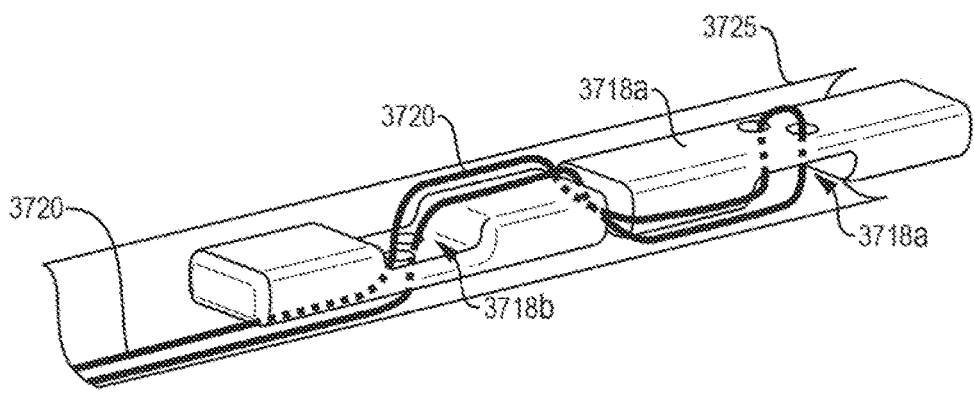
FIG. 37C illustrates the combination anchor and repair construct end housed within an insertion instrument, in accordance with this disclosure.

FIG. 37A-37C illustrates another double anchor embodiment, where the two anchors nest within each other. This would result in more radial loading distribution than the side by side arrangement illustrated in FIG. 35B. In this embodiment flexible member 3720 may extend directly from the first anchor 3715*a* to the second anchor 3715*b*. Each anchor 3715*a*, 3715*b* may include at least two apertures 3716, that when the two anchors are assembled, axially align. Each anchor 3715*a*, 3715*b* may include a central recess 3718*a*, 3718*b*, each recess 3718*a*, 3718*b* configured to receive the other recess 3718*a*, 3718*b* once assembled together, as illustrated in FIG. 37B. In the assembled configuration, elongate surface 3719*b* and split surfaces 3719*a* may engage the external bone surface. As such, these surfaces (3719*a*, 3719*b*) may be contoured to match and mate with the target bone external surface. FIG. 37C illustrates anchors 3715*a*, 3715*b* housed within a distal end of an inserter shaft, similar to inserter 3600. Anchors 3715*a*, 3715*b* may be housed with recesses 3718*a*, 3718*b* facing opposing directions. Anchors 3715*a*, 3715*b* may be housed with recesses 3718*a*, 3718*b* facing away from the shaft longitudinal axis of the inserter in opposite directions. Once anchors 3715*a*, 3715*b* have been ejected from inserter shaft distal end 3625, tension on flexible member 3720 may draw the two anchors together to form a cross shape (FIG. 37B).

FIGS. 38A and 38B illustrate an alternative anchor configuration that may inserted through a passage with a restricted opening size, while providing a larger footprint upon deployment. Anchor 3800 may unfold from a folded configuration 3800 to a deployed configuration 3800'. Anchor 3800 may include a plurality of arms 3810, oriented parallel to the anchor body longitudinal axis in the folded configuration 3800, and then may rotate to a radially extended configuration during deployment. Arms 3810 are orientated or contoured to engage an external surface of the target bone. Arms 3810 may be spring loaded, such that release from an inserter tube allows the arms 3810 to rotate to the deployed configuration. Anchor 3800 may also include a stem 3820 with a suture pulley aperture 3830 at an end of the stem 3820. Suture pulley aperture 3830 may help maintain a shorter axial length of flexible member along the repair, to reduce potential for elongation, as disclosed herein.

FIG. 39 illustrates another embodiment similar to embodiment 3800 including a single body that radially expands. Anchor embodiments 3800 may be formed of spring steel or nitinol that may relax to the expanded configuration. FIG. 39 illustrates anchor 3900 in a deployed/expanded configuration. Arms 3910 may be orientated in a stressed collapsed state, loaded within an insertion instrument tube (not shown) for example, and upon release from the tube, arms 3910 revert to the unstressed configuration, radially expanding to engage an external surface of bone around a single passage through the bone. Anchor 3900 is coupled to a flexible member and may be an anchor of repair constructs disclosed herein, including constructs 1300 or 2600 for example.

Another embodiment may include a two-piece anchor system 4000 that interlinks. A first anchor may be similar to anchor 1410 or anchor 1500 and may be provided preassembled to a flexible member construct 4020. First anchor (1410/1500) may be configured to pass through a limited size of passage through the bone(s). A second anchor may define a larger footprint and may include a cavity 4015 for engaging the first anchor (1410/1500). Second anchor may be positioned at a far side of the target bone by arm of a guide, similar to guide 510. First anchor (1410/1500) may then be passed through bone(s) and through an opening 4012 through second anchor 4010. Flipping first anchor and tensioning flexible member 4020 may draw first anchor into cavity 4015, illustrated in FIG. 40C. FIG. 40D illustrates a guide arm, similar to guide arm 520 placed on an exterior surface of a target bone, that may be releasably coupled to second anchor 4010.

Figure 41:
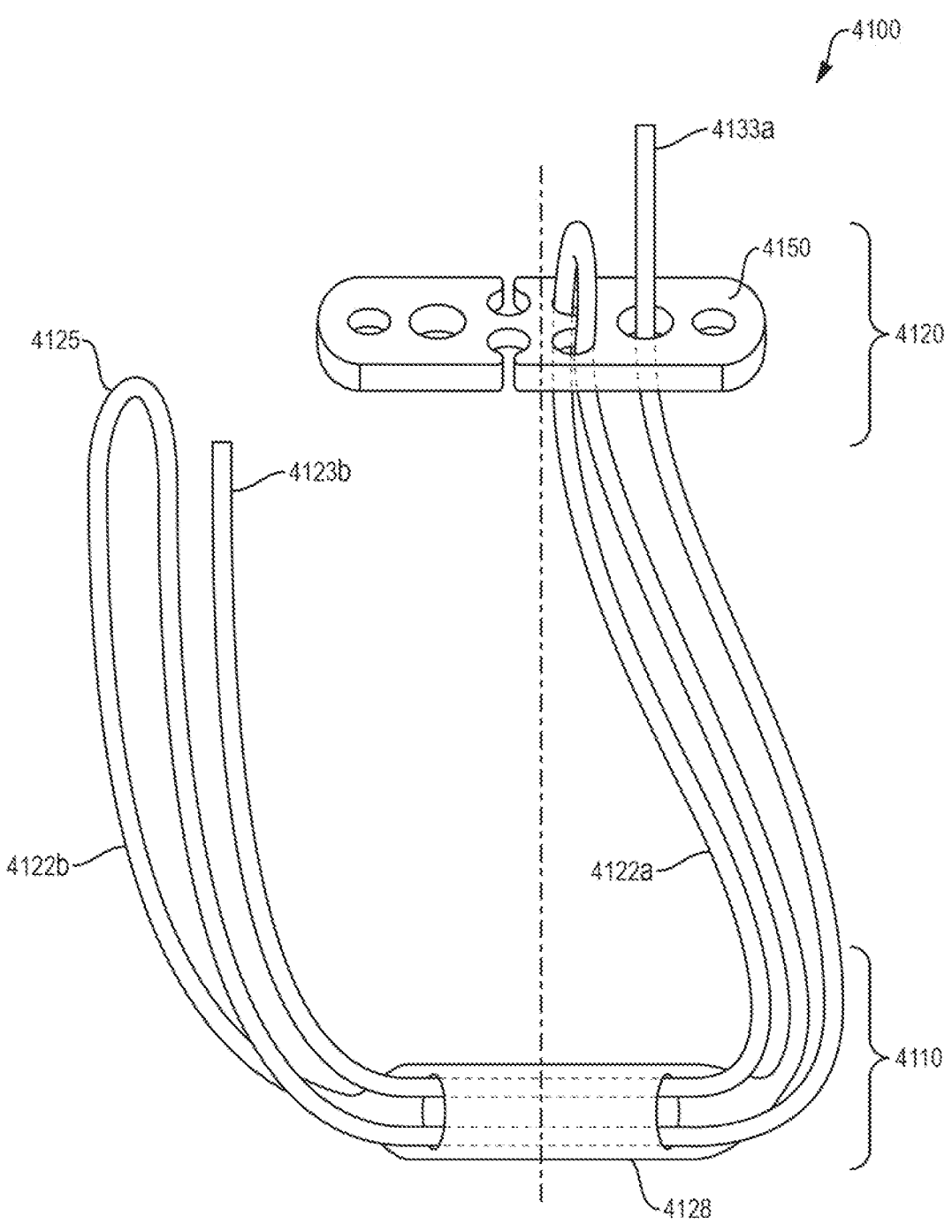
FIG. 41 illustrates an open loop repair construct, in accordance with this disclosure.

The disclosure now turns to construct embodiments that may avoid a passage through one of the bones of the joint altogether. These constructs may wrap around or cradle the bone. For example, in an AC joint repair, the flexible construct may wrap around the coracoid 22. Construct 4100, illustrated in FIG. 41 may include a cradling end 4110 for cradling or wrapping around the coracoid 22 and an anchoring end 4120 for anchoring with the clavicle 18. Construct 4100 may define an open loop construct in that it has a free end 4125 for wrapping under and around the coracoid 22. Free end 4125 may be assembled to an anchor 4150 after threading the free end 4125 around coracoid 22. Open loop construct 4100 may be provided with another end preassembled to an anchor 4150. Open loop construct 4100 may include two adjustable loops 4122a, 4122b extending from a suture locking passage 4128. A first of the adjustable loops 4122a may extend from a first side of the suture locking passage 4128 and the other of the adjustable loops 4122b may extend from an opposite side of the suture locking passage 4128. Suture locking passage 4128 may define the cradle portion, that cradles the coracoid 22. Open construct may include a first limb or end 4123a and a second limb or end 4123b. Withdrawing first end 4123a is configured to reduce adjustable loop 4122b. Withdrawing second end 4123b is configured to reduce adjustable loop 4122a. Anchor 4150 may be provided assembled to loop 4122a. Tension on at least one of the first or second ends (4123a, 4123b) may cinch suture locking cradle 4128 and knotlessly lock the construct 4100. Anchor 4150 may be similar to button 1410 or 1600. This and other example open loop constructs are disclosed in commonly owned PCT patent application US2020/038401, herein incorporated by reference in its entirety.

Figure 42B:
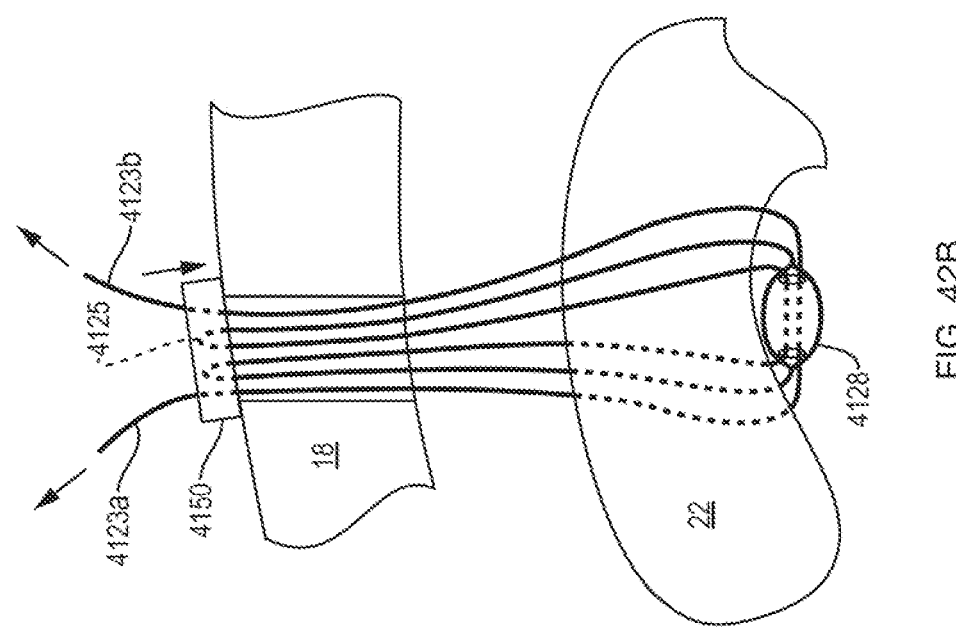
FIGS. 42A-42B illustrates a method of repairing an AC joint with an open loop construct, in accordance with this disclosure.
Figure 42A:
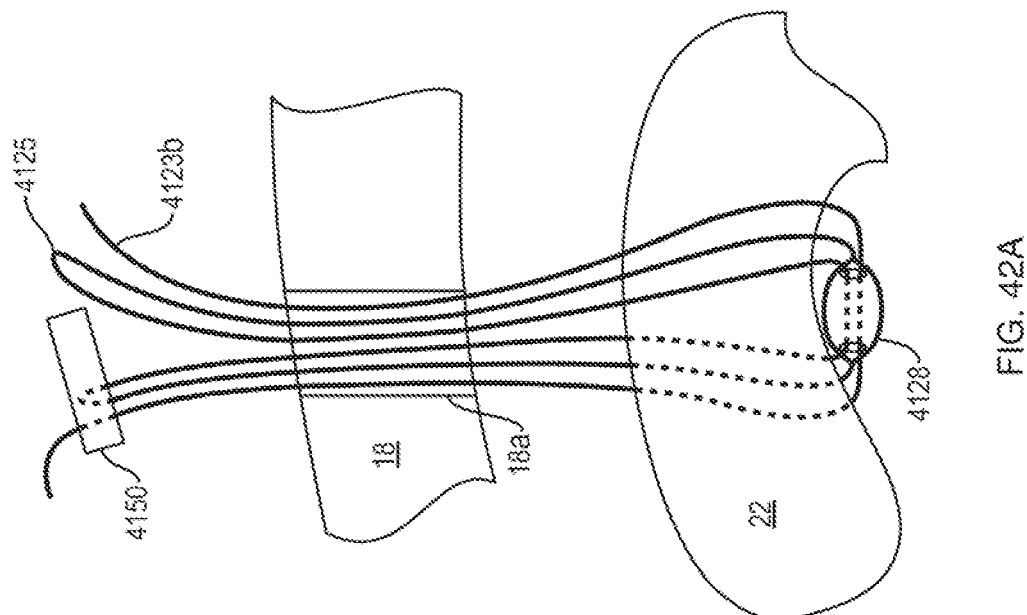

A method of AC joint repair is illustrated in FIGS. 42A-42B. A tunnel 18a may be formed through the clavicle 18 only. Tunnel 18a may be formed with a guide 510, bullet 540 and drill 550. Guide 510 may hold the two bones in a reduced arrangement while forming the tunnel 18a. Free end 4125 and end 4123b of construct 4100 may then be passed through the clavicle tunnel 18a and around inferior side of the coracoid 22, as shown in FIG. 42A. Locking passage 4128 may wrap around and cradle the inferior external surface of coracoid 22. Locking passage 4128 may define a dilated portion of the flexible member, which may increase the footprint on the coracoid 22 relative to a single length of the flexible member, and preferably reduce or mitigate stress concentration around the fragile coracoid 22. The free end 4125 may then be shuttled back through the clavicle tunnel 18a to extend from the clavicle superior surface. Insertion and shuttling instrumentation may extend along bullet similar to bullet 540 for example. The free end 4125 may then be assembled to the button 4150 and tension on ends 4123a, 4123b may reduce the adjustable loop construct 4100. This may hold the coracoid 22 and clavicle 18 in a reduced arrangement. This may reduce the construct to place the anchor 4150 on the superior surface of the clavicle 18. Ends 4123a, 4123b may be tensioned to cinch the suture locking passage 4128 and thereby lock the construct 4100 without the need for a knot on the superior surface of the clavicle. Since a knot on this surface may be palpable to the patient, avoiding a knot here is preferable. Ends 4123a, 4123b may then be trimmed.

Figure 43:
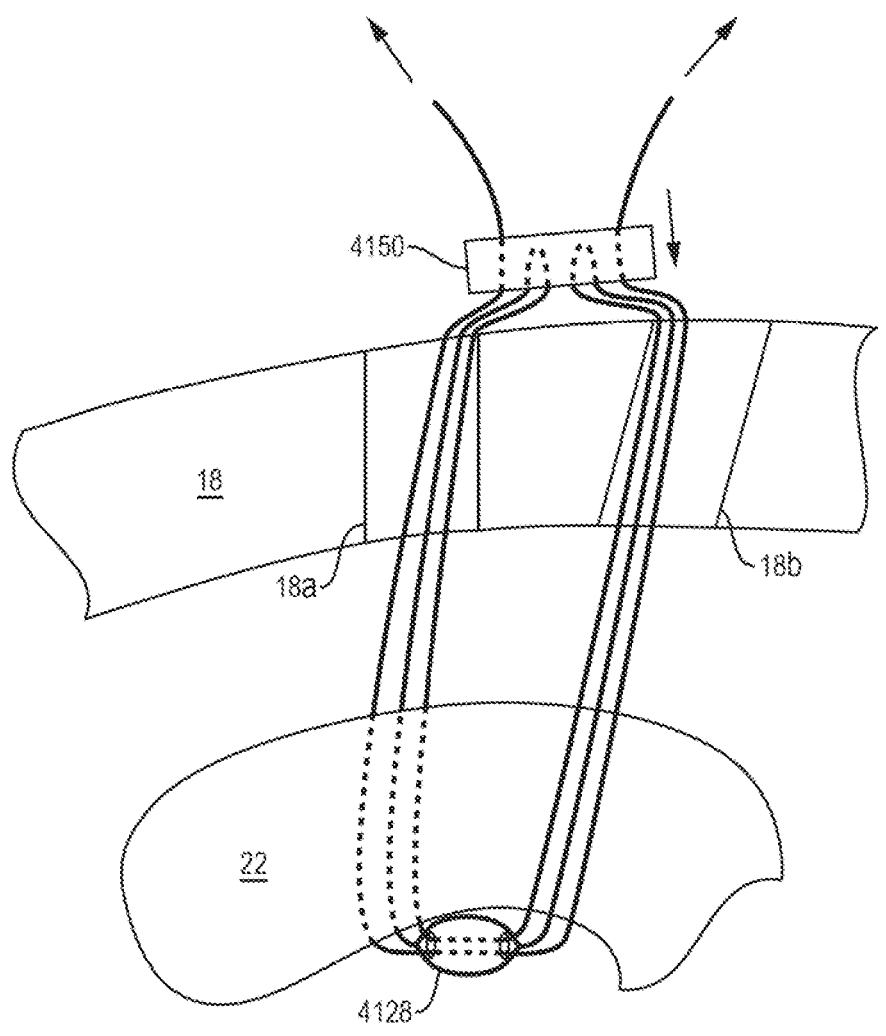
FIG. 43 illustrates another arrangement and associated method of repairing an AC joint with an open loop construct, in accordance with this disclosure.

Shown in FIG. 43 another method of repairing an AC joint with construct 4100 may include forming two tunnels 18a, 18b through the clavicle 18. The free end 4125 may be shuttled through both tunnels 18a, 18b in a loop. This would enable a bone bridge to support the button 4150. This may also replicate the insertion sites for the original CC ligaments, as discussed earlier. In other embodiments, the repair construct 4100 may include a graft component to address chronic injury. The graft may lie in parallel to the flexible members of the adjustable loop construct 4100.

Those skilled in the art will realize the disclosure may be embodied in other specific forms without departing from the spirit or essential characteristics thereof. The foregoing examples are therefore to be considered in all respects illustrative rather than limiting of the disclosure described herein. Scope of the disclosure is thus indicated by the appended claims, rather than by the foregoing description, and all changes that come within the meaning and range of equivalency of the claims are therefore intended to be embraced therein.

What is claimed is:

1. A tissue repair system including:

an adjustable loop construct formed of a flexible member, the adjustable loop construct including;

a first loop end and a second loop end opposite the first loop end;

a first locking passage and a second locking passage, each passage defining a first passage end and a second passage end, and wherein both first passage ends are closer to the first loop end than the second loop end;

two adjustable loops, each extending from both first passage ends and defining the first loop end; and a saddle length of the flexible member, extending directly from both second passage ends and defining the second loop end, the saddle length fixed in length;

a first reduction end of the flexible member extending from the second passage end of the first locking passage and a second reduction end of the flexible member extending from the second passage end of the second locking passage, wherein both first and second reduction ends extend towards the second loop end; and an all-suture anchor slidingly coupled to the first loop end; wherein the adjustable loop construct and the all-suture anchor are housed in an insertion instrument, the insertion instrument configured to apply tension to the adjustable loop construct to deploy the all-suture anchor, and wherein the locking passages are housed so as to prevent the locking passages from inadvertently locking while tensioning the adjustable loop construct.

2. The tissue repair system of claim 1 wherein the two adjustable loops interweave repeatedly through the all-suture anchor at spaced away locations through the all-suture anchor.

3. The tissue repair system of claim 1 wherein the saddle length is configured to operatively couple to a cortical anchor.

4. The tissue repair system of claim 1 wherein tension on the first and second reduction ends are configured to reduce the two adjustable loops.

5. The tissue repair construct of claim 1 wherein the locking passages are wrapped around a post of the insertion instrument while applying tension to the adjustable loop construct, the post disposed proximal to a handle of the insertion instrument.

6. The tissue repair system of claim 5 wherein the reduction ends are also wrapped around the post.

7. A tissue repair system, comprising:

an all-suture anchor having a plurality of apertures therethrough;

an adjustable loop construct formed with a flexible member, the adjustable loop construct including;

two adjustable loops coupled to the all-suture anchor via the plurality of apertures;

a first and a second locking passage separated from each other along the flexible member by a saddle length of the flexible member, the saddle length fixed in length;

wherein a first of the two adjustable loops are formed by threading a first end of the flexible member that extends from the first locking passage through two of the plurality of apertures and then through the second locking passage, a second of the two adjustable loops formed by threading a second end of the flexible member that extends from the second locking passage through two of the plurality of apertures and then through the first locking passage; wherein the adjustable loop construct and all-suture anchor are housed in an insertion instrument, the insertion instrument configured to apply tension to the adjustable loop construct to deploy the all-suture anchor, and wherein the locking passages are housed so as to prevent the locking passages from inadvertently locking while tensioning the adjustable loop construct; and a cortical button configured to couple to the saddle length.

8. The tissue repair system of claim 7 wherein the cortical button includes a concave bone engaging surface.

9. The tissue repair system of claim 7 wherein the saddle length defines a single length of the flexible member, free of suture locking passages.

10. The tissue repair system of claim 7 wherein the first end of the flexible member extends directly from the all-suture anchor through the second locking passage and emerges to define a first reducing end and wherein the second end of the flexible member extends through the first locking passage and emerges therefrom to define a second reducing end, the first and second reducing ends extending away from the all-suture anchor.

11. The tissue repair system of claim 7 wherein the second cortical button defines a non-passing button with a single slot configured to receive the saddle length therein.

12. The tissue repair system of claim 7 wherein the locking passages are wrapped around a post of the insertion instrument while applying tension to the adjustable loop construct, the post extending proximally from a handle of the insertion instrument.

13. A method of forming a tissue repair system with an all-suture anchor having a plurality of apertures therethrough and a length of flexible member having a first and second end, the method comprising drawing the first end through two of the plurality of apertures and then introducing the first end into a first lumen of the flexible member at a first location along the length of the flexible member and then out of the first lumen at a second location, defining a first adjustable loop coupled to the all-suture anchor with the first end extending away from the all-suture anchor;

drawing the second end through two of the plurality of apertures, and then introducing the second end into a second lumen of the flexible member at a third location along the length of the flexible member and then out of the second lumen at a fourth location, defining a second adjustable loop coupled to the all-suture anchor and the second end extending away from the all-suture anchor;

wherein the second and fourth locations are spaced away from each other a fixed distance, defining a saddle length; and assembling the adjustable loop construct and all-suture anchor to an insertion instrument, the insertion instrument configured to apply tension to the adjustable loop construct to deploy the all-suture anchor, and assembling the first and second lumen so as to prevent the first and second lumen from inadvertently cinching while applying tension to the adjustable loop construct.

14. The method of claim 13 further comprising looping the saddle length through a slot of a cortical button.

15. The method of claim 13 wherein the second and fourth location are spaced away from each other by less than 10 mm, measured along a longitudinal axis of the saddle length.

16. The method of claim 13 when assembling includes wrapping the first and second lumens around a post of the insertion instrument located at a proximal end of a handle of the insertion instrument.

* * * * *